(12) United States Patent
Che et al.

(10) Patent No.: US 10,243,154 B2
(45) Date of Patent: Mar. 26, 2019

(54) PLATINUM(II) COMPLEXES FOR OLED APPLICATIONS

(71) Applicant: Versitech Limited, Hong Kong (CN)

(72) Inventors: Chi Ming Che, Hong Kong (CN); Chi Fai Kui, Hong Kong (CN); Chi Chung Kwok, Hong Kong (CN)

(73) Assignee: Versitech Limited, Hong Kong (CN)

( * ) Notice: Subject to any disclaimer, the term of this patent is extended or adjusted under 35 U.S.C. 154(b) by 0 days.

(21) Appl. No.: 15/950,650

(22) Filed: Apr. 11, 2018

(65) Prior Publication Data

US 2018/0233680 A1   Aug. 16, 2018

Related U.S. Application Data

(62) Division of application No. 15/054,247, filed on Feb. 26, 2016, now Pat. No. 10,008,681, which is a division of application No. 13/861,119, filed on Apr. 11, 2013, now Pat. No. 9,306,178.

(60) Provisional application No. 61/623,339, filed on Apr. 12, 2012.

(51) Int. Cl.
| | | |
|---|---|---|
| *H01L 51/00* | (2006.01) | |
| *C09K 11/06* | (2006.01) | |
| *H05B 33/14* | (2006.01) | |
| *C07F 15/00* | (2006.01) | |
| *C07D 401/14* | (2006.01) | |
| *C07D 401/12* | (2006.01) | |
| *C07D 213/38* | (2006.01) | |
| *C07D 213/74* | (2006.01) | |
| *H01L 51/50* | (2006.01) | |

(52) U.S. Cl.
CPC ........ *H01L 51/0087* (2013.01); *C07D 213/38* (2013.01); *C07D 213/74* (2013.01); *C07D 401/12* (2013.01); *C07D 401/14* (2013.01); *C07F 15/0086* (2013.01); *C09K 11/06* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/185* (2013.01); *H01L 51/0072* (2013.01); *H01L 51/0094* (2013.01); *H01L 51/5016* (2013.01)

(58) Field of Classification Search
CPC ............ H01L 51/0087; H01L 51/0072; H01L 51/0094
See application file for complete search history.

(56) References Cited

U.S. PATENT DOCUMENTS

| 7,442,797 B2 | 10/2008 | Itoh et al. |
| 8,877,353 B2 | 11/2014 | Che et al. |
| 2010/0140602 A1* | 6/2010 | Sotoyama ........... H01L 51/0087 257/40 |
| 2013/0009118 A1 | 1/2013 | Stoessel et al. |
| 2014/0138632 A1 | 5/2014 | Kim et al. |

OTHER PUBLICATIONS

Office Action dated Jun. 30, 2015 in U.S. Appl. No. 13/861,119.
Restriction Requirement dated Oct. 8, 2014 in U.S. Appl. No. 13/861,119.

\* cited by examiner

*Primary Examiner* — Pancham Bakshi
(74) *Attorney, Agent, or Firm* — Saliwanchik, Lloyd & Eisenschenk

(57) ABSTRACT

The current invention relates to novel platinum(II) based organometallic materials. These materials show high emission quantum efficiencies and low self-quenching constant. Also provided are high efficiency, green to orange emitting organic light-emitting diode (OLED) that are fabricated using platinum(II) based organometallic materials as the light-emitting material. The organometallic materials of the invention are soluble in common solvents; therefore, solution process methods such as spin coating and printing can be used for device fabrication. The devices fabricated from these materials show low efficiency roll-off.

7 Claims, 4 Drawing Sheets

PLATINUM(II) COMPLEXES FOR OLED APPLICATIONS

CROSS-REFERENCE TO RELATED APPLICATIONS

The subject application is a divisional application of U.S. application Ser. No. 15/054,247, filed Feb. 26, 2016, which is a divisional application of U.S. application Ser. No. 13/861,119, filed Apr. 11, 2013, now U.S. Pat. No. 9,306,178, issued Apr. 5, 2016, which claims the benefit of U.S. Provisional Application Ser. No. 61/623,339, filed Apr. 12, 2012, which are incorporated herein by reference in their entirety.

TECHNICAL FIELD

The present invention relates to a class platinum(II) complexes, their preparation methods, and their applications in organic light-emitting diodes (OLED).

BACKGROUND

As organic light-emitting diodes (OLEDs) are recognized as the next-generation display and lighting technology, OLED related technologies are rapidly developing. Organic-based emitting material is one of the most important core technologies in OLED; therefore, much effort has been devoted to this area. Since triplet emitters could fully utilize all excitons generated in the device, they are the focus in the field of emissive material development.

The idea of using phosphorescent materials in OLED was independently introduced by Baldo et al., Ma, and Che et al. in 1998. The world's first phosphorescent OLED (P-OLED) was fabricated using phosphorescent platinum(II) complex [Pt(OEP)] (OEP=octaethylporphin) (Nature 1998, 395, 151-154) and osmium(II) complex [Os(CN)$_2$(PPh$_3$)(X)] (X=4,4'-diphenyl-2,2'-bipyridine) (Synth. Met. 1998, 94, 245-248) as emitting materials respectively. High efficiency P-OLEDs have continuously been fabricated from new phosphorescent materials and are useful in various mobile electronics devices such as cellphones.

Although the phosphorescent materials that are currently used in the OLED industry have high emissive quantum efficiency (more than 60%), improved phosphorescent materials are needed. As a result, continuous attempts have been made in the development of new materials, especially blue-emitting materials.

In addition, most P-OLEDs suffer from high roll-off. In the cases of platinum containing materials, more than 90% roll-off is observed in 1,000 cd/m$^2$ (Applied Physics Letter 92, 163305 (2008), Chemical Communications 2005, 1408-1410, Chemical Communications 2004, 1484-1485, Applied Physics Letter 91, 063508 (2007), Chemistry A European Journal 2010, 16, 233-247). This problem of high efficiency roll-off is due to triplet-triplet annihilation and/or excimer formation. To solve this problem, previous researchers added bulky groups such as tert-butyl groups in the emissive molecules; nevertheless, the P-OLEDs fabricated from these materials still have more than 50% roll-off (Applied Physics Letter 91, 063508 (2007), Advanced Material 2007, 19, 3599-3603).

BRIEF SUMMARY

This present invention relates to novel platinum(II)-based materials having the chemical structure of Structure I. Also provided are methods of preparing the platinum(II)-based materials, and their applications in organic light-emitting diode (OLED).

In one embodiment, the platinum(II)-based compounds of Structure I are shown as follows:

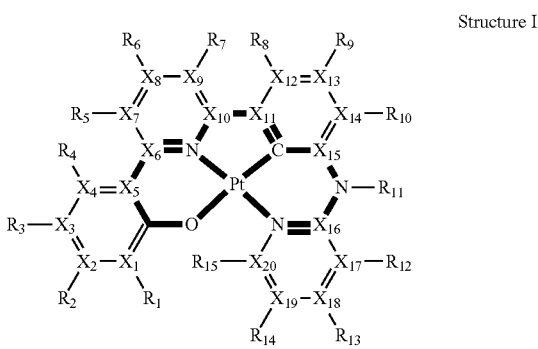

Structure I wherein $R_1$-$R_{15}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;

wherein each pair of adjacent R groups of $R_1$-$R_{15}$ can be independently two separated groups (or atoms) or one group (or atom), and form 5-8 member ring(s) with 2 or 4 X groups; and wherein $X_1$-$X_{20}$ are independently boron, carbon, nitrogen, oxygen, silicon, germanium, phosphorous, sulphur or selenium.

In one embodiment, the platinum(II) center is surrounded by the ligands featuring with a 6-5-6 fused membered ring system (the bolded line in structure I).

In one embodiment, $R_{11}$ is aryl or substituted aryl group, and $R_{10}$ can be one of the carbon atoms on $R_{11}$, thereby forming a 6-5-6 fused ring system with the adjacent aryl ring.

The present invention also provides devices fabricated from the platinum(II)-based compounds of Structure I. Advantageously, the devices of the invention exhibit high efficiency and low roll-off.

DETAILED DESCRIPTION

Definitions

Figure 1:
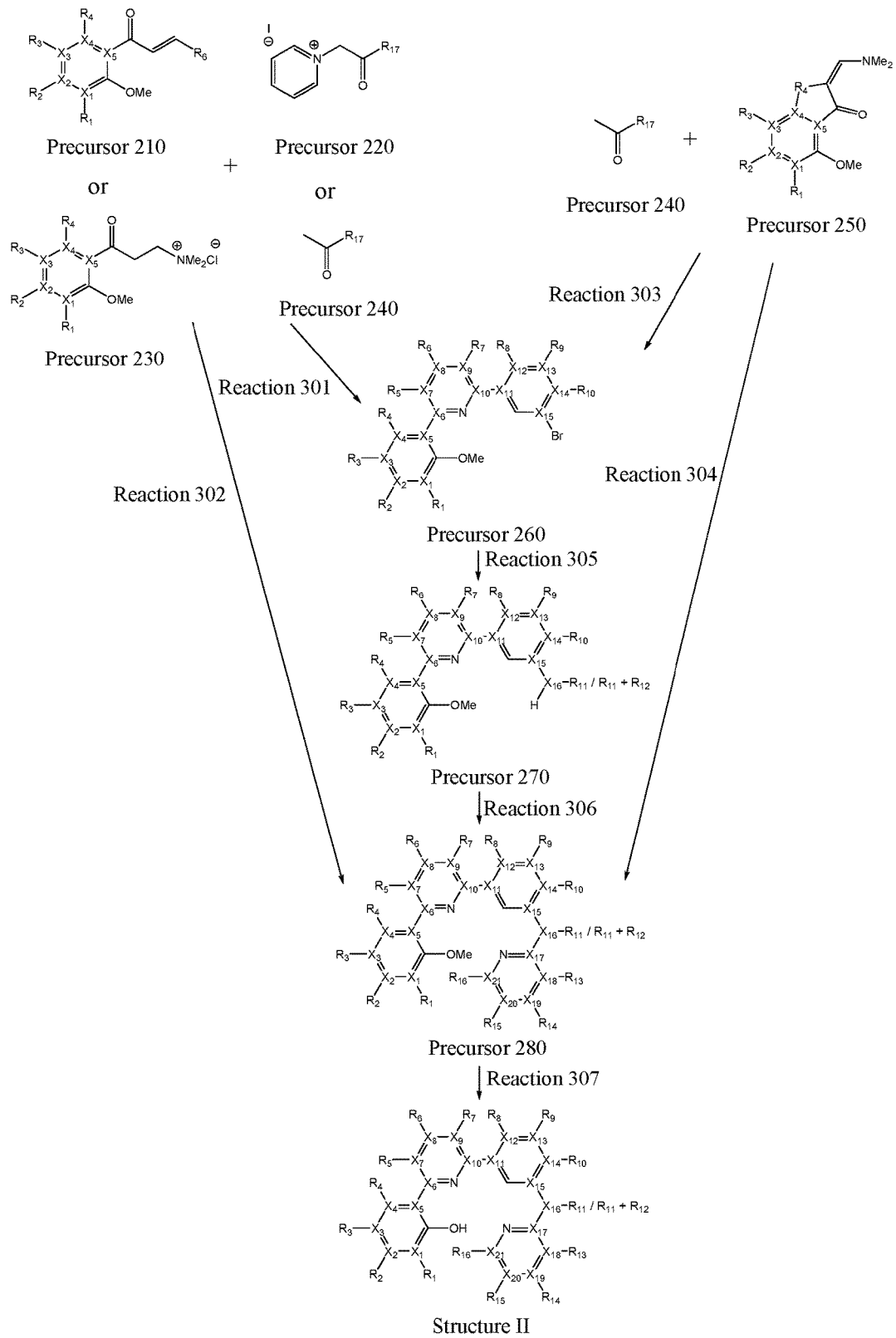
FIG. 1 shows one embodiment of the synthetic scheme of the platinum(II)-based organometallic compounds of Structure I. In an exemplified embodiment, the compound of Structure I is prepared using a ligand of Structure II. For the Precursors 210 to 280 and the compound of Structure II, $R_1$-$R_{16}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group; and $X_1$-$X_{21}$ are independently boron, carbon, nitrogen, oxygen, silicon, germanium, phosphorous, sulphur or selenium. In certain embodiments, each pair of adjacent R groups of $R_1$-$R_{16}$ can be independently two separated groups (or atoms) or one group (or atom), and form 5-8 member ring(s) with 2 to 4 X groups.
Figure 2:
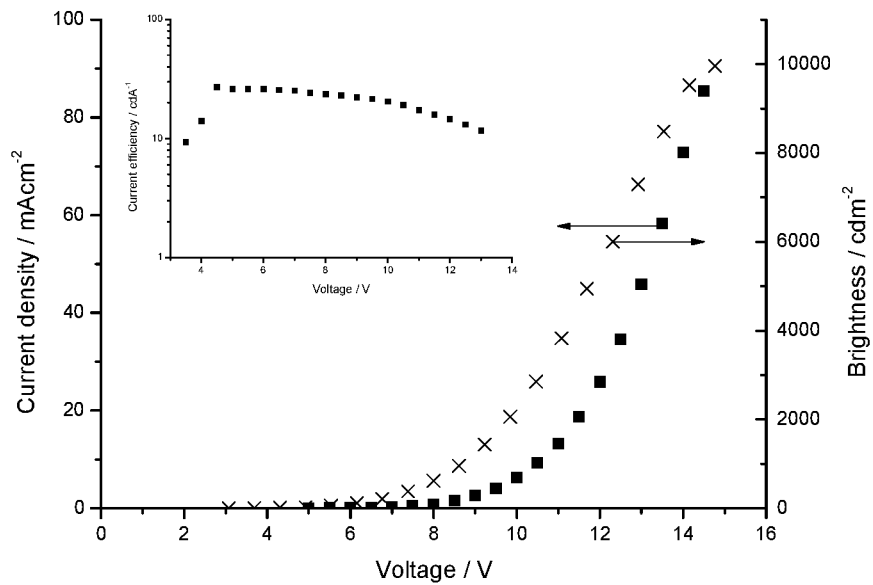
FIG. 2 shows the current density-voltage-brightness (J-B-V) relationship and efficiency-voltage curves of OLED 1.
Figure 3:
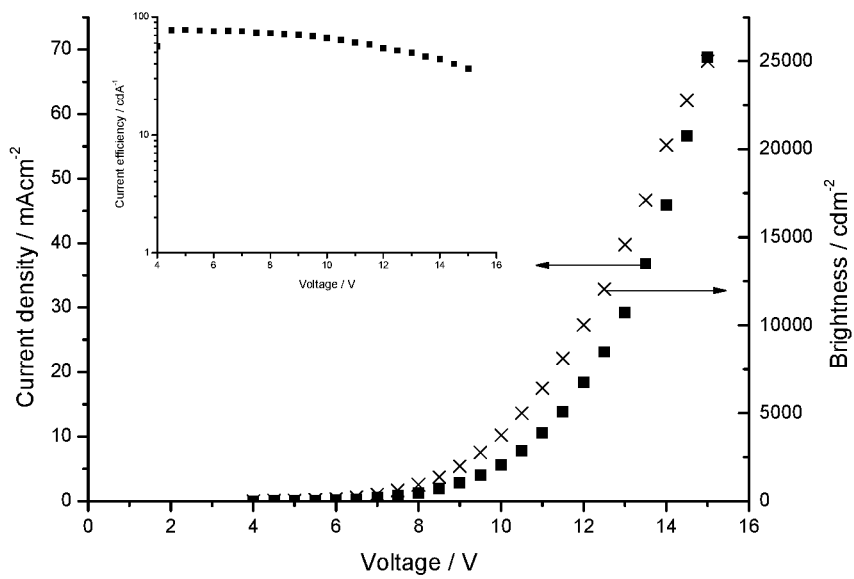
FIG. 3 shows the current density-voltage-brightness (J-B-V) relationship and efficiency-voltage curves of OLED 2.
Figure 4:
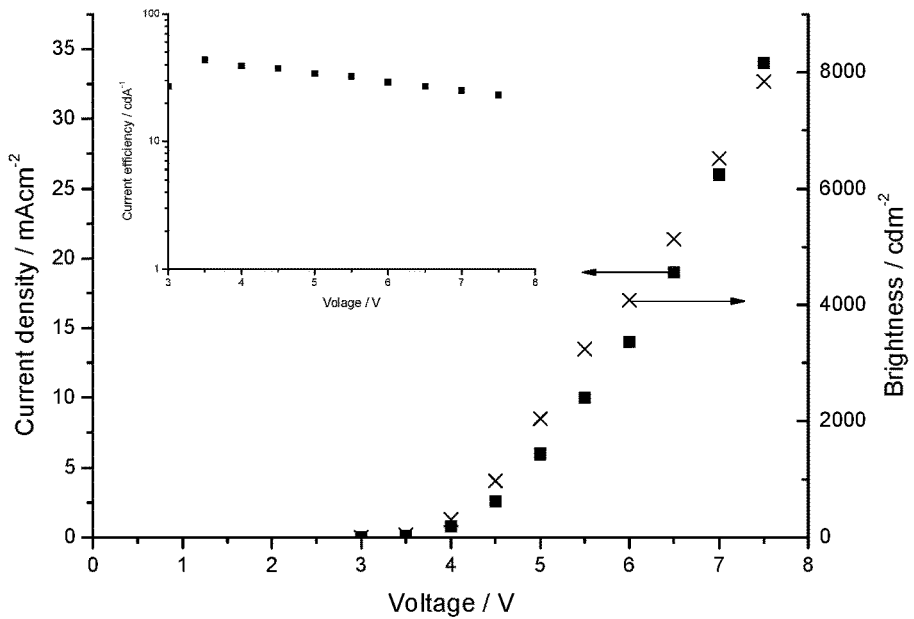
FIG. 4 shows the current density-voltage-brightness (J-B-V) relationship and efficiency-voltage curves of OLED 3.
Figure 5:
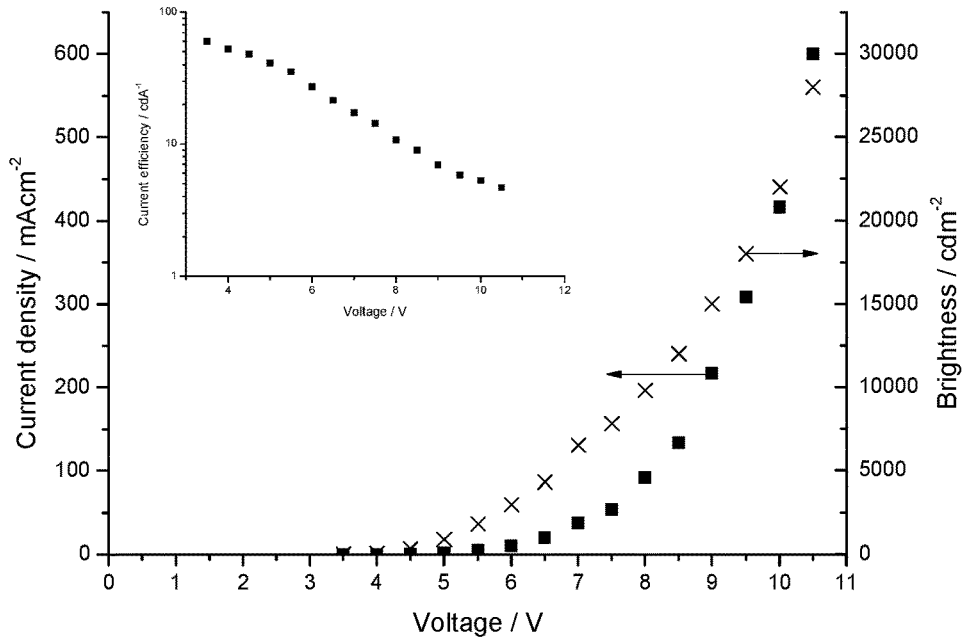
FIG. 5 shows the current density-voltage-brightness (J-B-V) relationship and efficiency-voltage curves of OLED 4.
Figure 6:
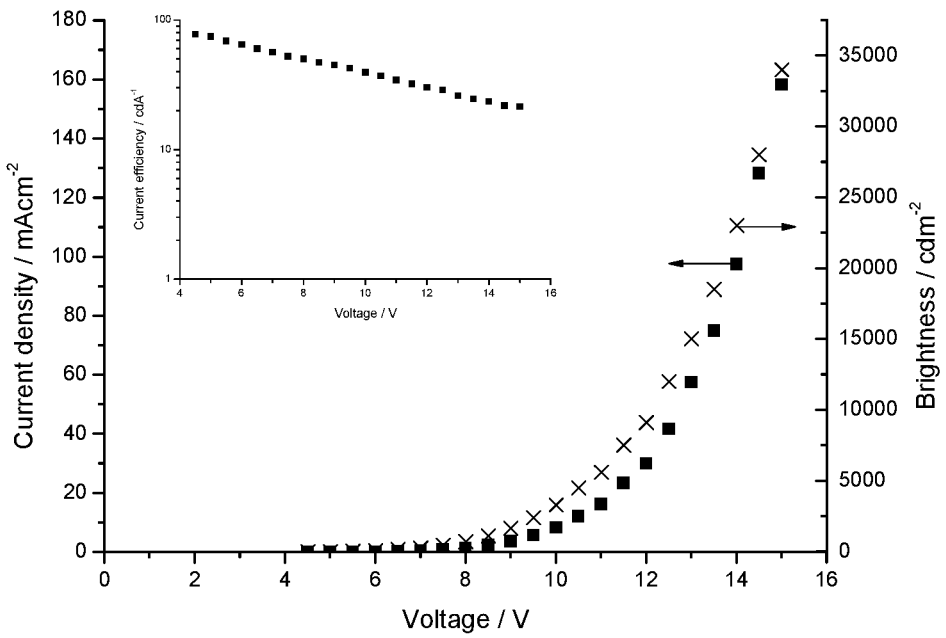
FIG. 6 shows the current density-voltage-brightness (J-B-V) relationship and efficiency-voltage curves of OLED 5.
Figure 7:
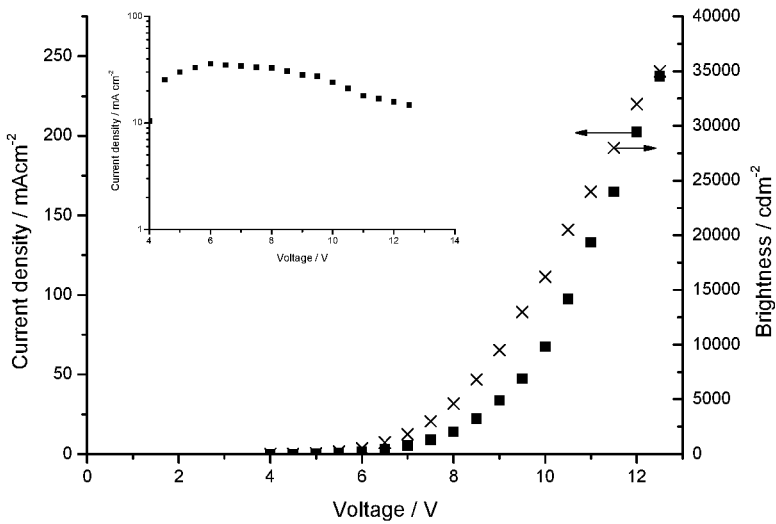
FIG. 7 shows the current density-voltage-brightness (J-B-V) relationship and efficiency-voltage curves of OLED 6.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of an amino group include —NR'R" wherein each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. Examples of alkyl groups include, but are not limited to, methyl, ethyl, n-propyl, isopropyl, n-butyl, t-butyl, n-heptyl, n-hexyl, n-octyl, and n-decyl.

"Alkylamino" means a radical —NHR or —NR$_2$ where each R is independently an alkyl group. Representative examples of alkylamino groups include, but are not limited to, methylamino, (1-methylethyl)amino, methylamino, dimethylamino, methylethylamino, and di(1-methyethyl)amino.

The term "hydroxyalkyl" means an alkyl radical as defined herein, substituted with one or more, preferably one, two or three hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl, and 1-(hydroxymethyl)2-hydroxyethyl.

The term "alkoxy," as used herein, refers the radical —OR$_x$. Exemplary alkoxy groups include, but are not limited to, methoxy, ethoxy, and propoxy.

"Aromatic" or "aromatic group" refers to aryl or heteroaryl.

"Aryl" refers to optionally substituted carbocyclic aromatic groups. In some embodiments, the aryl group includes phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Styryl" refers to a univalent radical C$_6$H$_5$—CH=CH— derived from styrene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl; heteroaryl; hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO$_2$CH$_3$; —CONH$_2$; —OCH$_2$CONH$_2$; —NH$_2$; SO$_2$NH$_2$; —OCHF$_2$; —CF$_3$; —OCF$_3$; —NH(alkyl); —N(alkyl)$_2$; —NH(aryl); —N(alkyl)(aryl); —N(aryl)$_2$; —CHO; —CO(alkyl); —CO(aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

Light-Emitting Platinum(II)-Based Organometallic Complex

In one aspect, the present invention provides platinum (II)-based organometallic compounds. In one embodiment, an organometallic complex represented by Structure I, also referred herein as cyclometallated complexes, is provided. The platinum center in Structure I is in +2 oxidation state and has a square planar geometry. The coordination sites of the platinum center are occupied by a tetradentate ligand. The tetradentate ligand featuring with 6-5-6 fused membered rings coordinates to the platinum center through a metal-oxygen bond, a nitrogen donor bond, a metal-carbon bond and a nitrogen donor bond in a sequence of O, N, C, N (O^N^C*N ligand; i.e., 4 connecting covalent bonds (either single or double) between O^N, 3 connecting covalent bonds (either single or double) between N^C, 4 connecting covalent bonds (either single or double) between C*N). The metal-oxygen bond is a bond between deprotonated phenol or substituted phenol and platinum, the nitrogen donors are from pyridine and/or isoquinoline groups, and the metal-carbon bond is formed by benzene or substituted benzene and platinum.

In one embodiment, the platinum(II)-based organometallic compounds have the chemical structure of Structure I

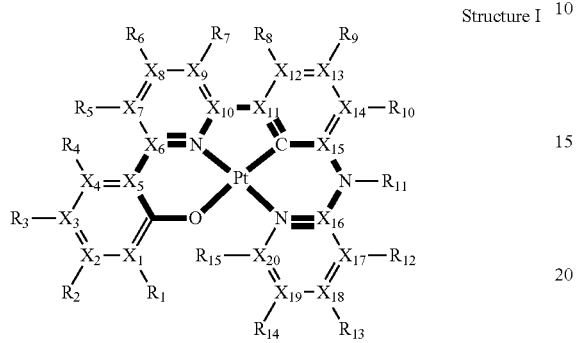

Structure I wherein $R_1$-$R_{15}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;

wherein each pair of adjacent R groups of $R_1$-$R_{15}$ can be independently two separated groups (or atoms) or one group (or atom), and form 5-8 member ring(s) with 2 or 4 X groups; and wherein $X_1$-$X_{20}$ are independently boron, carbon, nitrogen, oxygen, silicon, germanium, phosphorous, sulphur or selenium.

In one embodiment, the platinum(II) center is surrounded by the ligands featuring with a 6-5-6 fused membered ring system (the bolded line in structure I).

In one embodiment, $R_{11}$ is aryl or substituted aryl group, and $R_{10}$ can be one of the carbon atoms on $R_{11}$ thereby forming a 6-5-6 fused ring system with the adjacent aryl ring.

In one embodiment, each $R_1$-$R_{15}$ is independently hydrogen, halogen (such as fluorine, chlorine bromine, and iodine), hydroxyl, an unsubstituted alkyl containing from 1 to 10 carbon atoms, a substituted alkyl containing from 1 to 20 carbon atoms, cycloalkyl containing from 4 to 20 carbon atoms, an unsubstituted aryl containing from 6 to 20 carbon atoms, a substituted aryl containing from 6 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thiol, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

In another embodiment, the total number of carbon atoms provided by the $R_1$-$R_{15}$ groups is from 1 to 40.

In another embodiment, the total number of carbon atoms provided by the $R_1$-$R_{15}$ groups is from 2 to 30.

Certain specific, non-limiting examples of the organometallic complexes with Structure I are shown as follows:

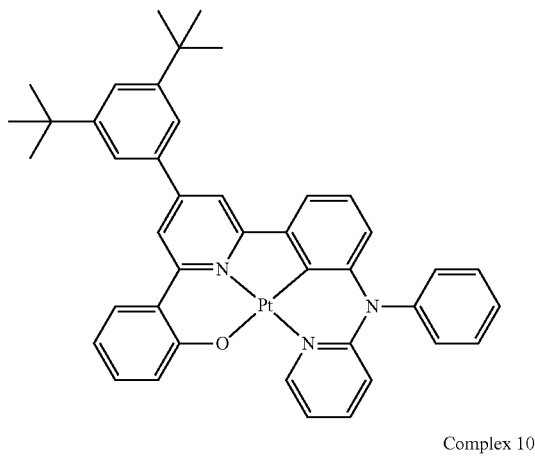

Complex 101

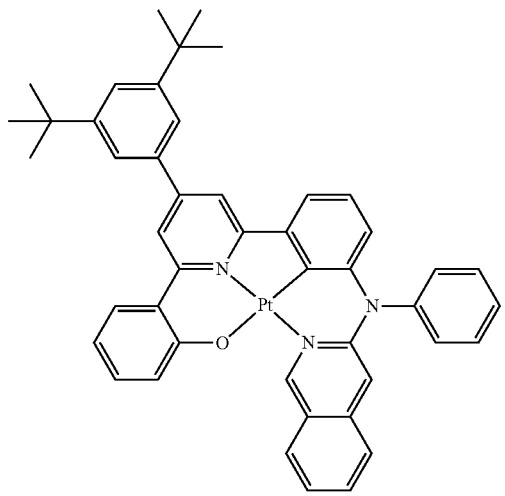

Complex 102

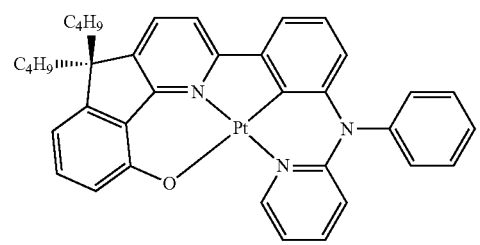

Complex 103

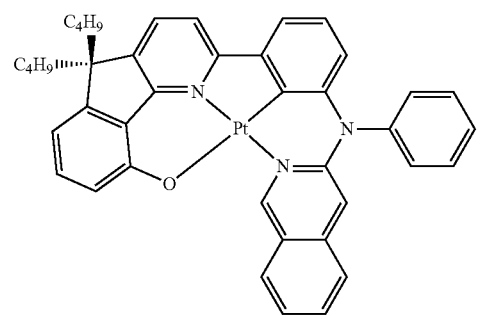

Complex 104

Complex 105
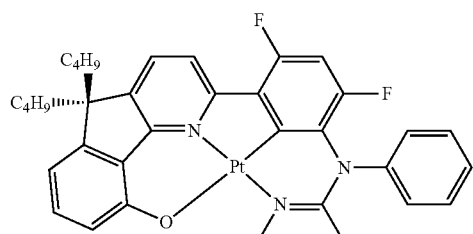
Complex 106
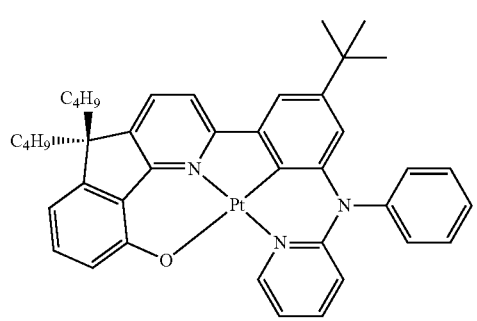
Complex 107
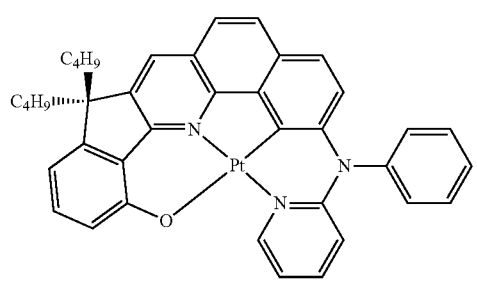
Complex 108
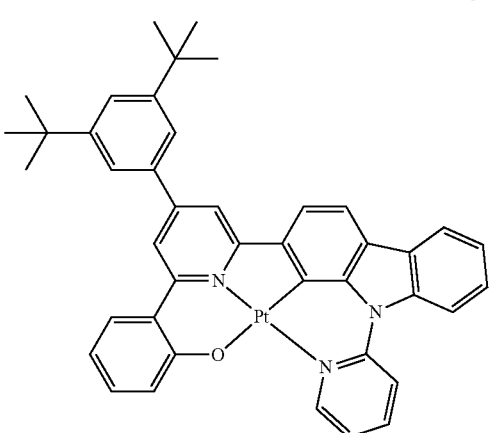
Complex 109
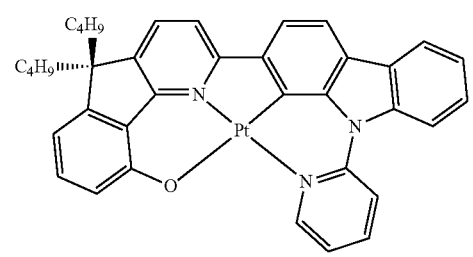
Complex 110
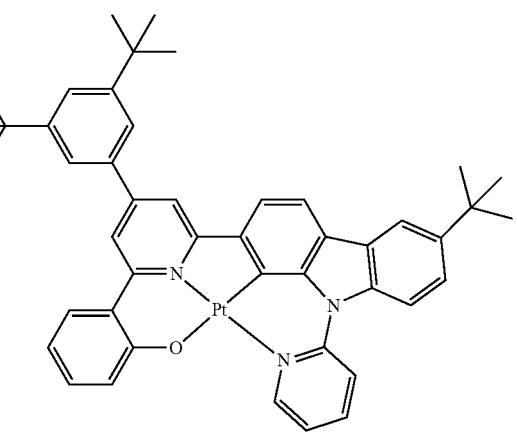
Complex 111
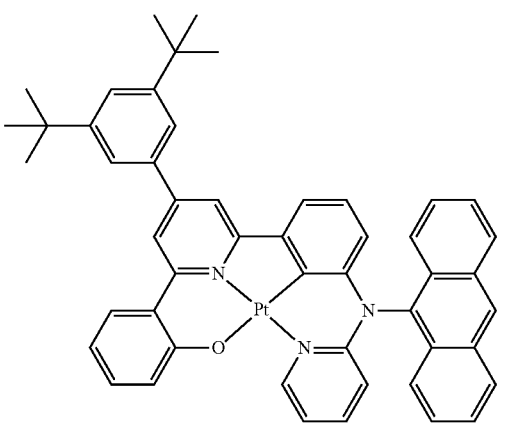
Complex 112
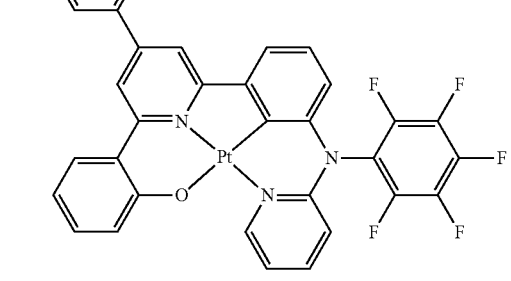

Complex 113
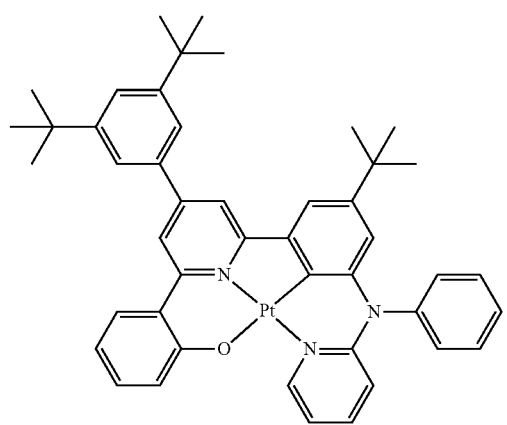
Complex 116
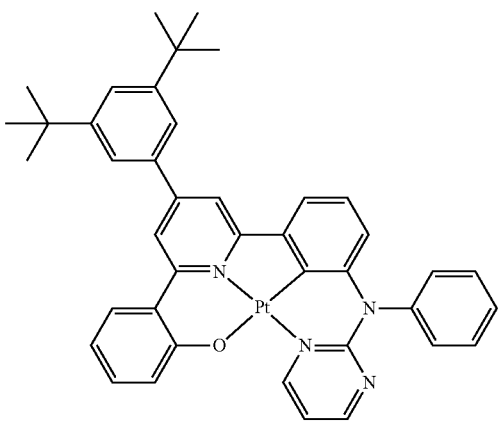
Complex 114
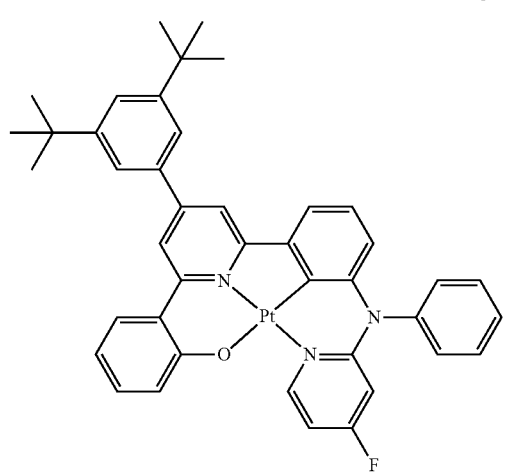
Complex 117
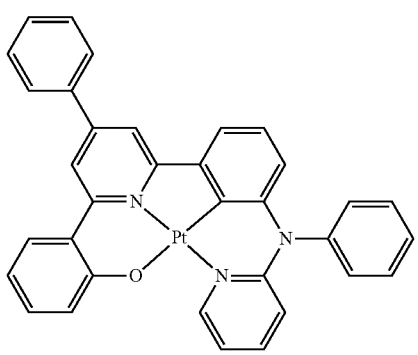
Complex 115
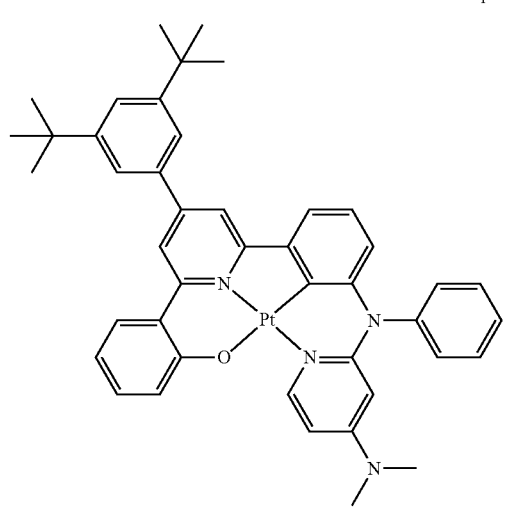
Complex 118
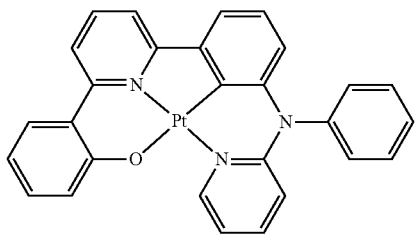
Complex 119
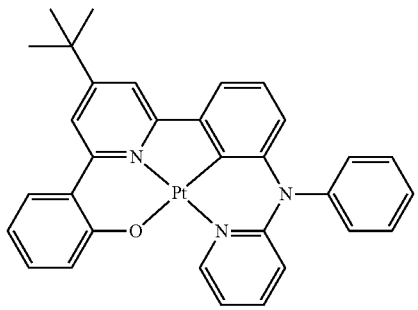

Complex 120
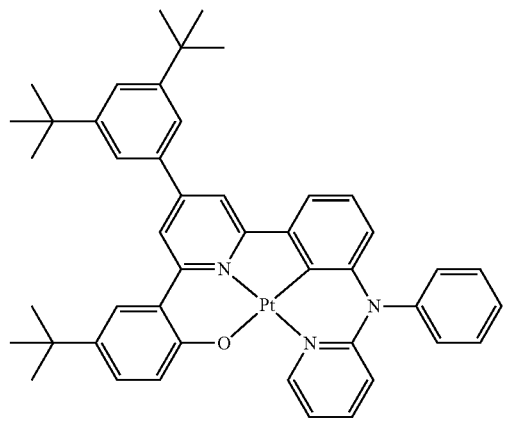
Complex 121
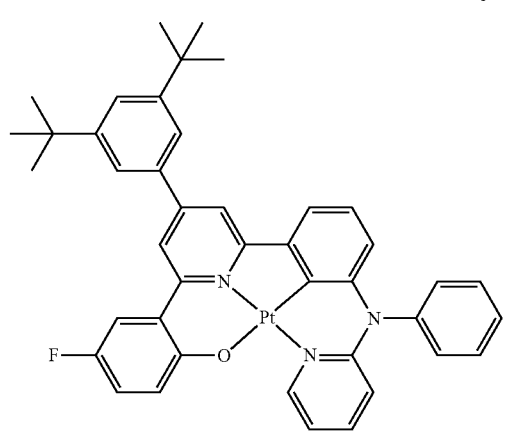
Complex 122
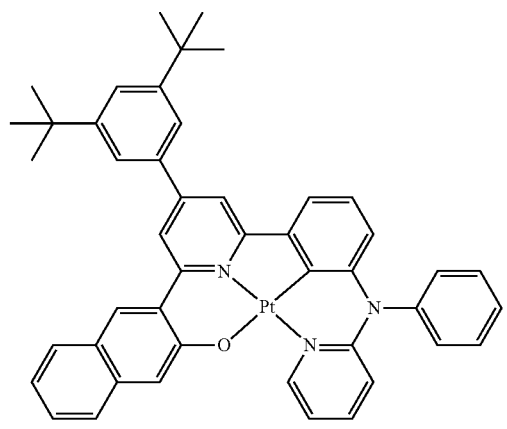
Complex 123
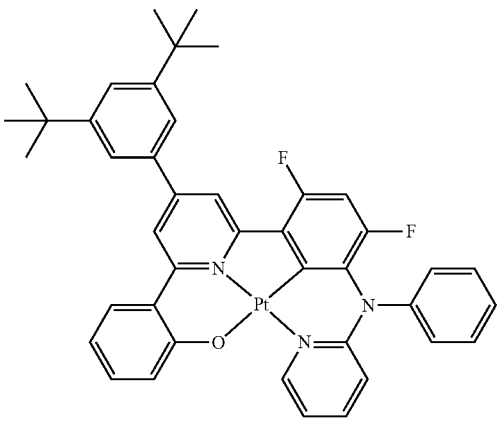
Complex 124
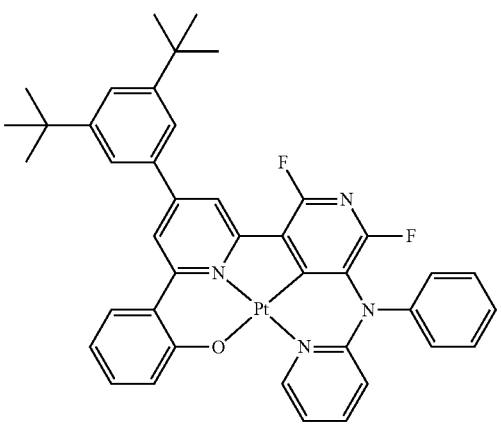
Complex 125
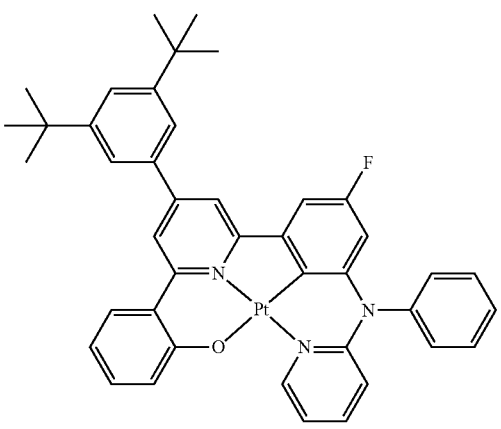

Complex 126
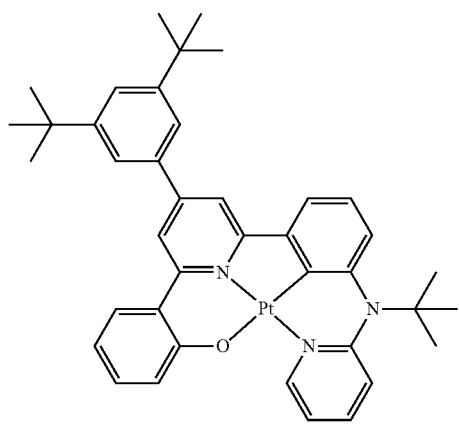
Complex 127
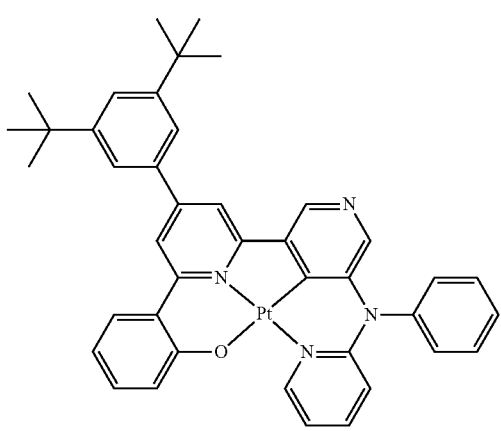
Complex 128
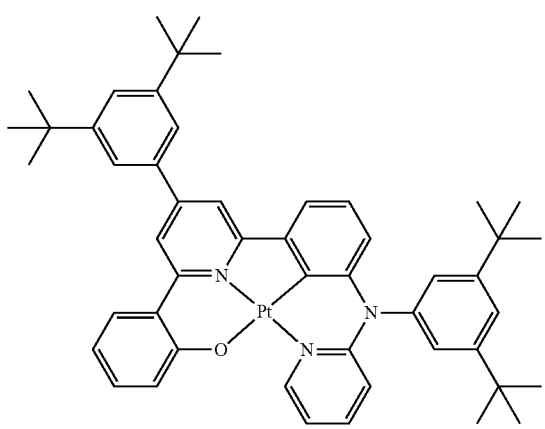
Complex 129
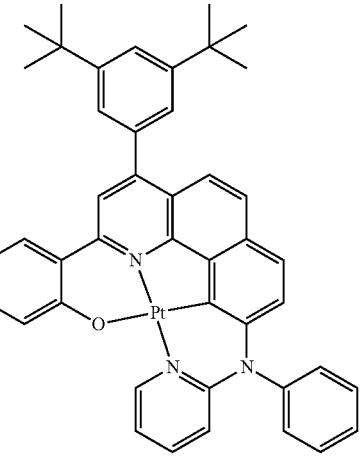
Complex 130
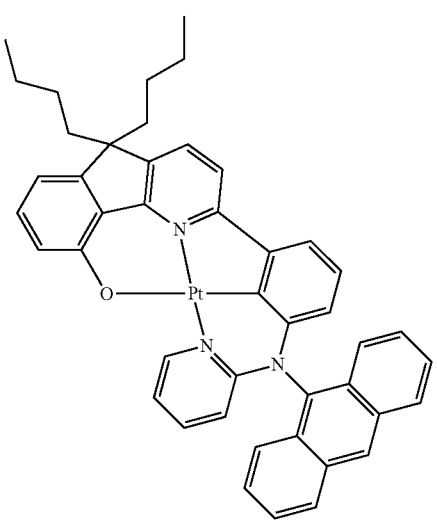
Complex 131
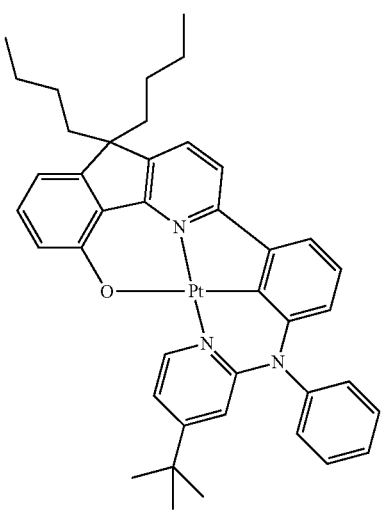
Preparation of Platinum(II)-Based Organometallic Complex
In one embodiment, the organometallic complex with the chemical structure of Structure I can be prepared from a tetradentate ligand with a chemical structure of Structure II:

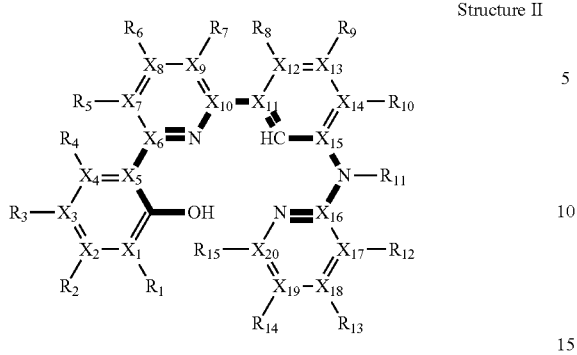

Structure II wherein $R_1$-$R_{15}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;

wherein each pair of adjacent R groups of $R_1$-$R_{15}$ can be independently two separated groups (or atoms) or one group (or atom), and form 5-8 member ring(s) with 2 or 4 X groups; and wherein $X_1$-$X_{20}$ are independently boron, carbon, nitrogen, oxygen, silicon, germanium, phosphorous, sulphur or selenium.

In one embodiment, $R_{11}$ is aryl or substituted aryl group, and $R_{10}$ can be one of the carbon atoms on $R_{11}$ thereby forming a 6-5-6 fused ring system with the adjacent aryl ring.

In one embodiment, each $R_1$-$R_{15}$ is independently hydrogen, halogen (such as fluorine, chlorine bromine, and iodine), hydroxyl, an unsubstituted alkyl containing from 1 to 10 carbon atoms, a substituted alkyl containing from 1 to 20 carbon atoms, cycloalkyl containing from 4 to 20 carbon atoms, an unsubstituted aryl containing from 6 to 20 carbon atoms, a substituted aryl containing from 6 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thio, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

In another embodiment, the total number of carbon atoms provided by the $R_1$-$R_{15}$ groups is from 1 to 40.

In another embodiment, the total number of carbon atoms provided by the $R_1$-$R_{15}$ groups is from 2 to 30.

Certain specific non-limiting examples of the tetradentate ligand with Structure II are shown below:

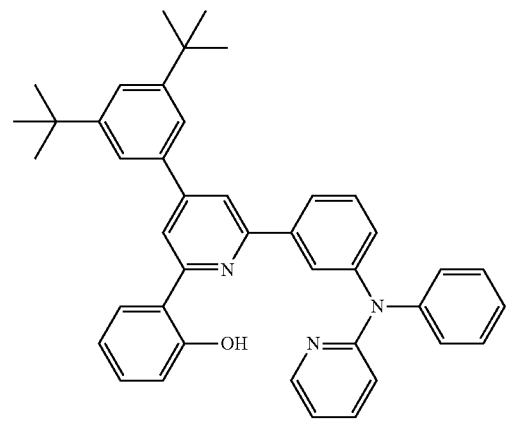

Ligand 401

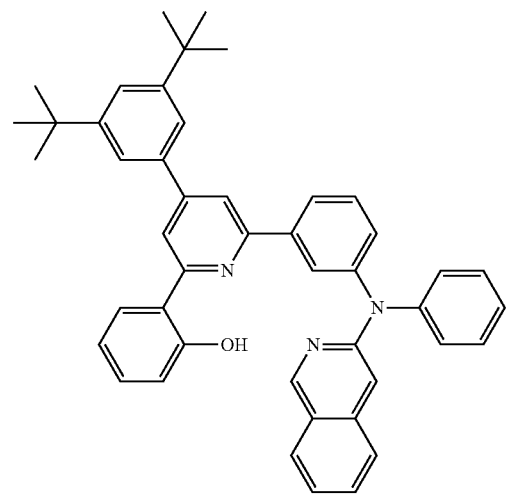

Ligand 402

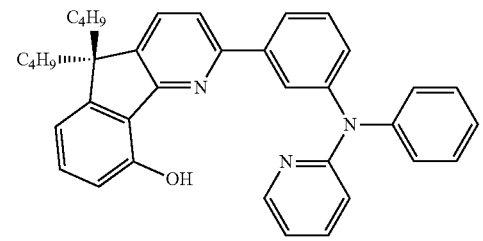

Ligand 403

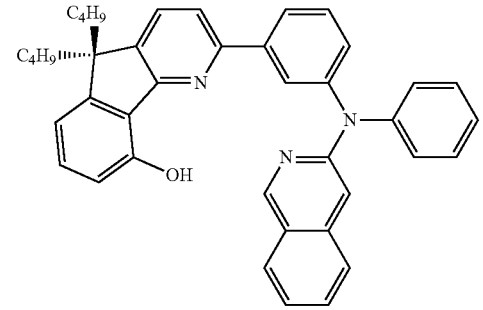

Ligand 404

-continued
Ligand 405
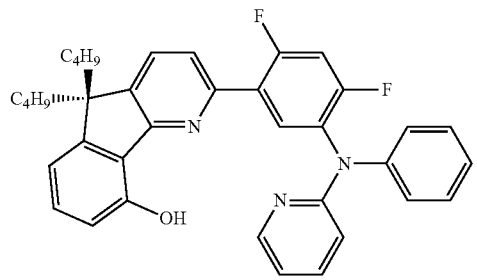
Ligand 406
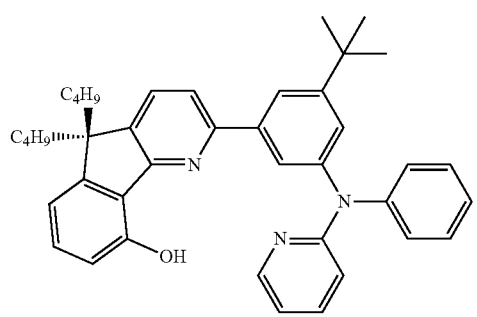
Ligand 407
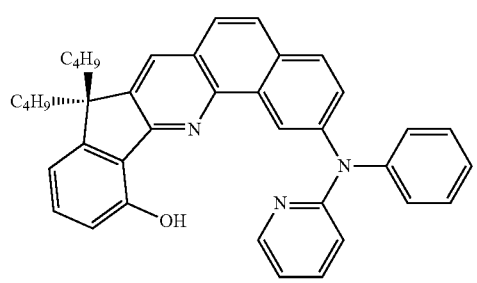
Ligand 408
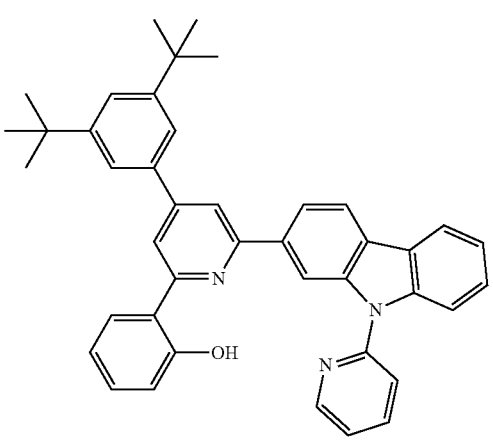
Ligand 409
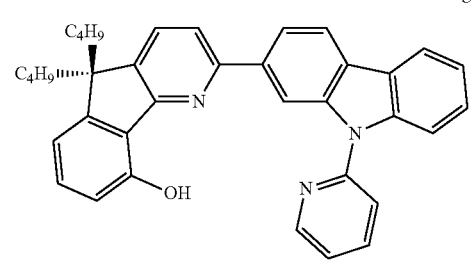
-continued
Ligand 410
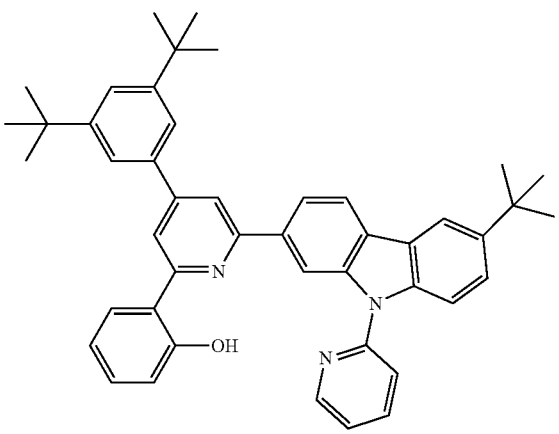
Ligand 411
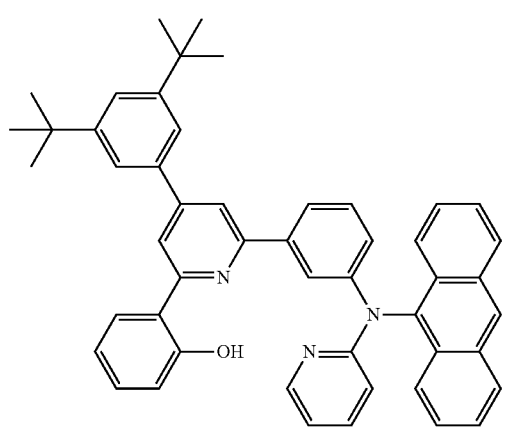
Ligand 412
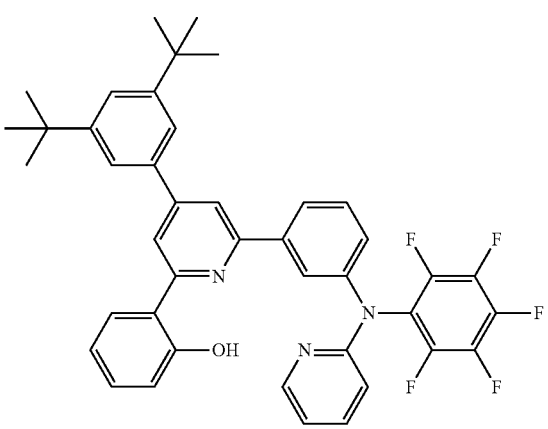

Ligand 413
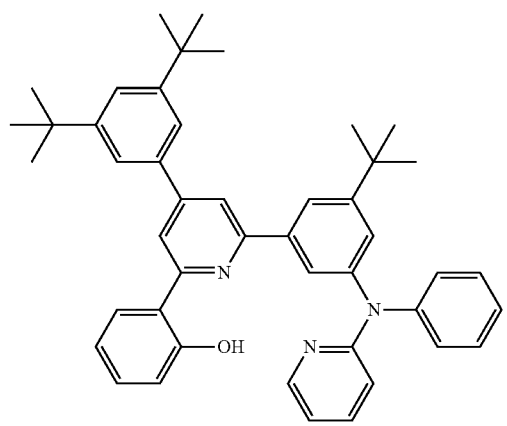
Ligand 414
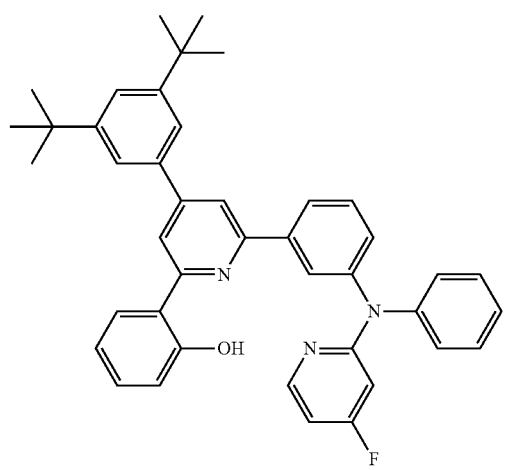
Ligand 415
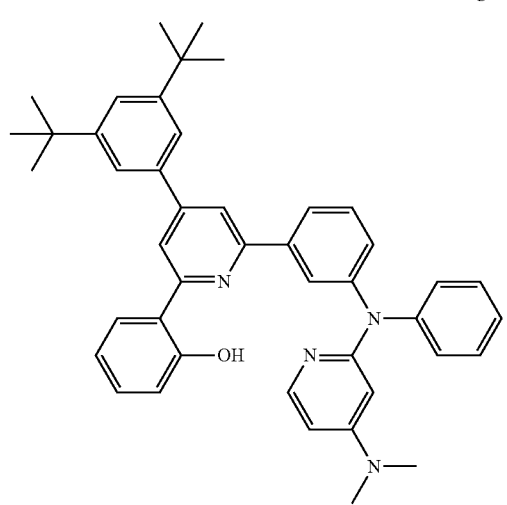
Ligand 416
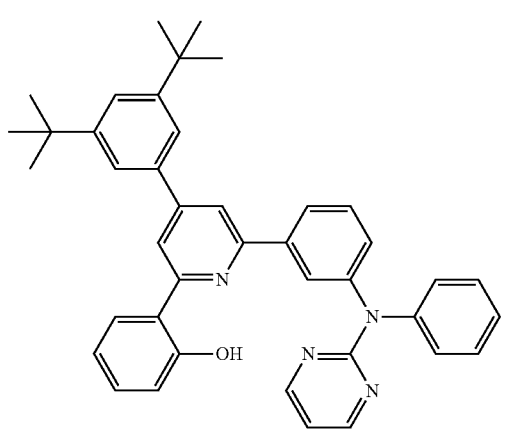
Ligand 417
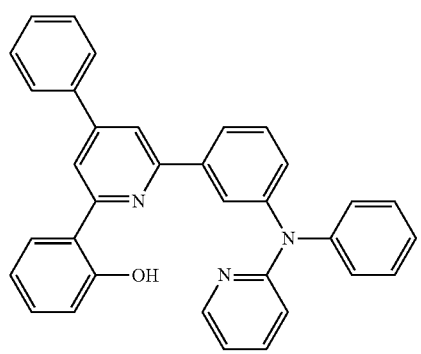
Ligand 418
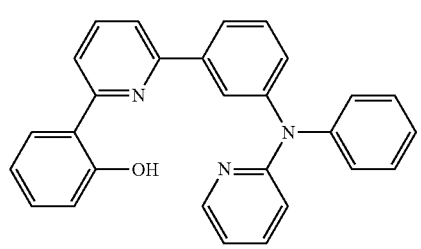
Ligand 419
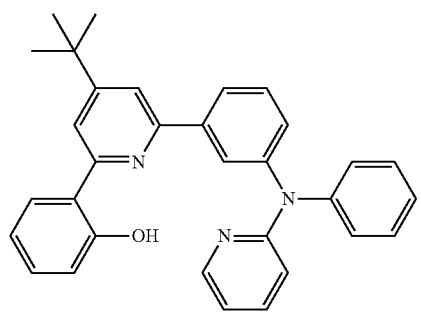

Ligand 420
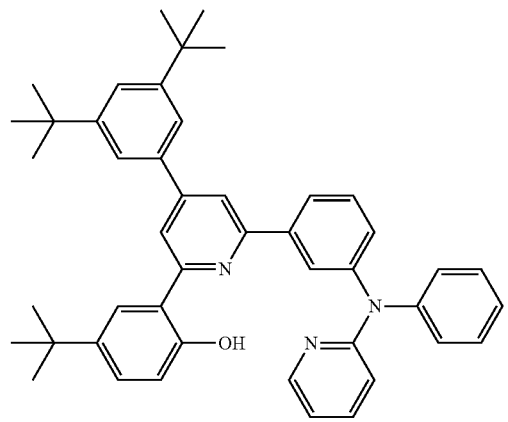
Ligand 421
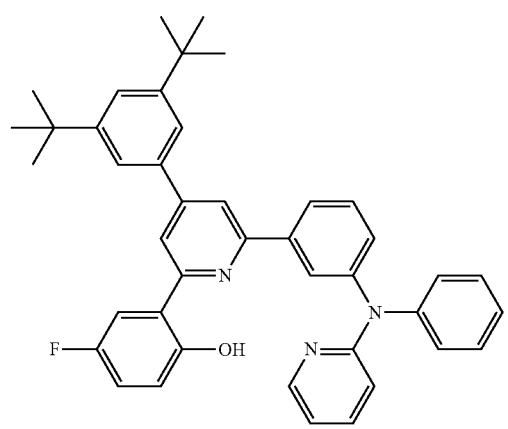
Ligand 422
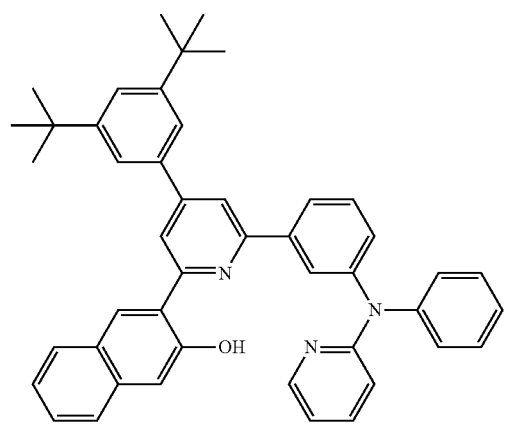
Ligand 423
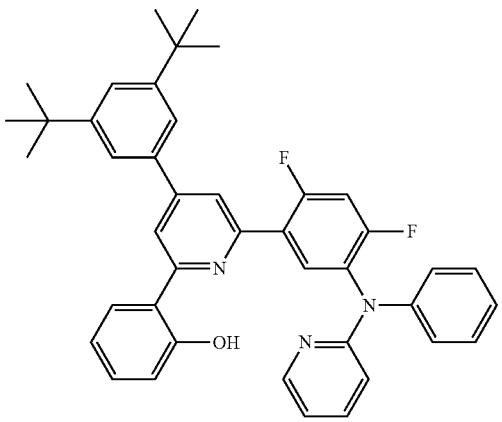
Ligand 424
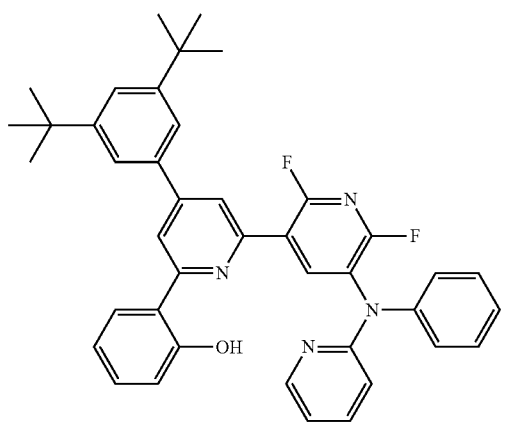
Ligand 425
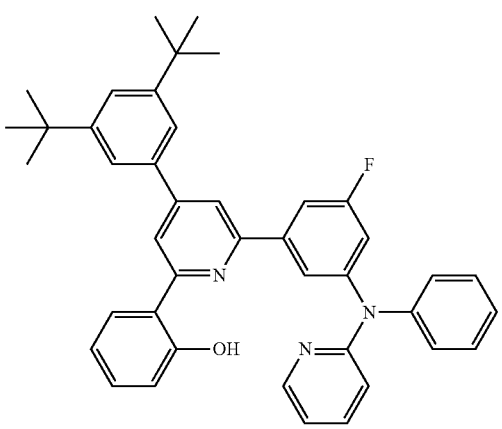

Ligand 426
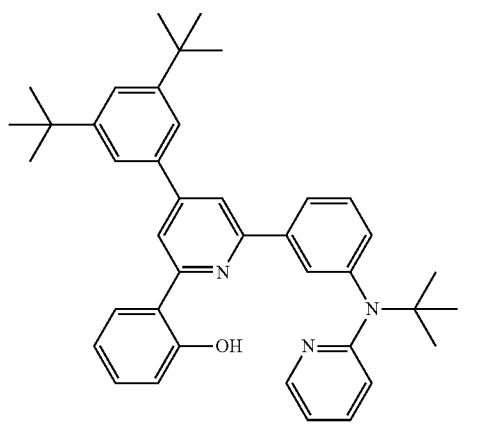

Ligand 427
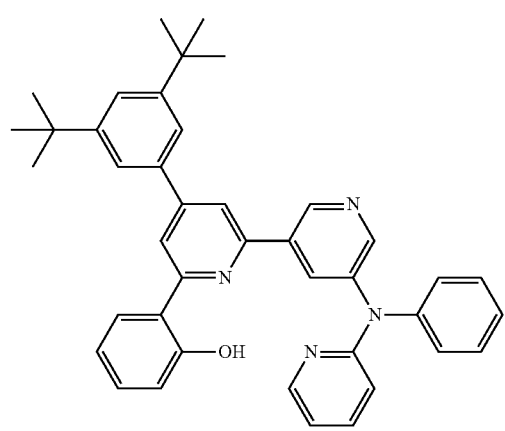

Ligand 428
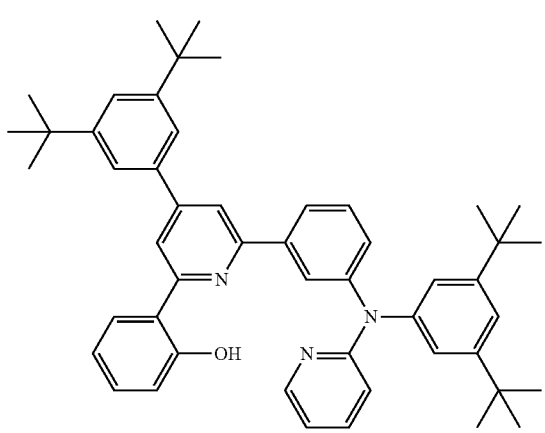

Ligand 429
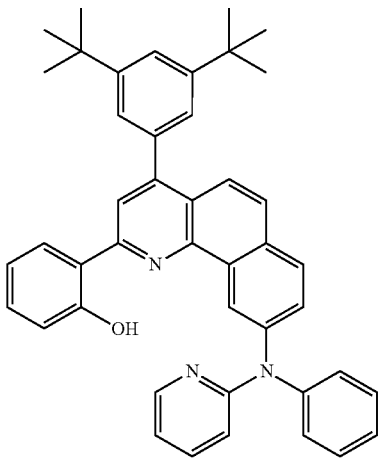

Ligand 430
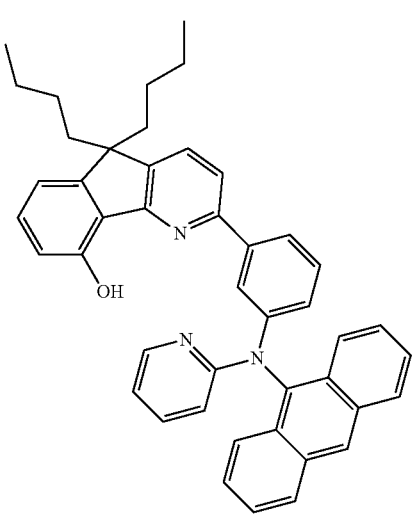

Ligand 431
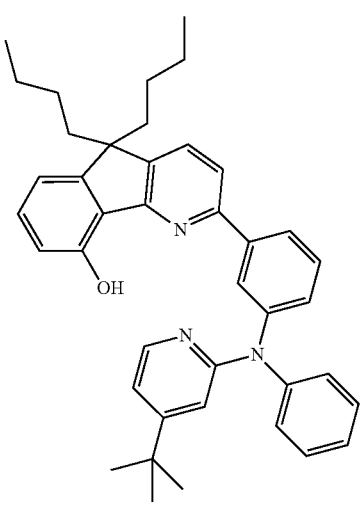

In one embodiment, the tetradentate ligands with Structure II can be prepared by a series of reactions depicted in FIG. 1.

According to FIG. 1, Precursor 210 reacts with Precursor 220 or Precursor 230 reacts with Precursor 240, through Reaction 301 to form Precursor 260 or through Reaction 302 to form Precursor 280, depending on the chemical structure of the Precursor 210-Precursor 240. If Precursor 260 is produced, it is transformed to Precursor 270 through Reaction 305 and then transformed to Precursor 280 through Reaction 306. Finally, Precursor 208 is transformed to a ligand with a chemical structure of Structure II by Reaction 307. Precursor 260 and Precursor 280 can also be produced by reacting Precursor 240 with Precursor 250 through Reaction 303 or Reaction 304. All reactions 301-307 can be a single step or multi-step reaction.

In one embodiment, Reaction 301 comprises reacting Precursor 210 and Precursor 220 or Precursor 230 and Precursor 240. In one embodiment, Reaction 301 is performed in the presence of excess ammonium acetate and a solvent under a reflux condition. Suitable solvents for Reaction 301 include, but are not limited to, methanol. In one embodiment, Reaction 305 comprises a palladium coupling reaction using bis[2-(diphenylphoshpine)phenyl]ether (DPE-phos) as a ligand, tris(dibenzylideneacetone)dipalladium(0) as the catalyst, potassium tert-butoxide as the base and toluene as the solvent, under an inert nitrogen environment at 80° C.

In one embodiment, Reaction 306 is the same as Reaction 305.

In one embodiment, Reaction 307 comprises reacting pyridine hydrogen chloride with Precursor 280.

In one embodiment, Reaction 307 comprises reacting carbon tetarbromide with Precursor 280.

In another embodiment, the present invention provides a method of preparing the organometallic complex with chemical structure of Structure I, comprising reacting a ligand with chemical structure of Structure II with a platinum(II) salt in the presence of solvent(s). Other chemicals such as based will be added if they are needed in the reaction. In one embodiment, the platinum(II) salt is potassium tetrachloroplatinate. In another embodiment, the solvents are glacial acetic acid and chloroform.

Industrial Applications of Platinum(II) Based Organometallic Complexes

The platinum(II) based organometallic complexes having the chemical structure of Structure I show strong emission with high solution quantum yield.

As the platinum(II) based organometallic complexes of Structure I have a rigid structure which reduces the non-radioactive decay, the emission quantum efficiency of these complexes are high. Therefore, high efficiency organic light emitting diode (OLED) can be fabricated by using these complexes as emitting material.

In one embodiment, the OLED fabricated using the organometallic complex of Structure I shows a high efficiency of greater than 70 cd/A. In another embodiment, the OLED fabricated using the organometallic complex of Structure I shows a high efficiency of greater than 40 cd/A, including, but not limited to, greater than 45 cd/A, 50 cd/A, 55 cd/A, 60 cd/A, 65 cd/A, 70 cd/A, 75 cd/A, 80 cd/A, or 85 cd/A.

In one embodiment, the organometallic complexes with the chemical structure of Structure I have a $X_{15}$—N—$X_{16}$-$R_{11}$ substructure which makes the complexes non-planar; as a result, the self-quenching effect of these complexes are low. In one embodiment, the self-quenching constant for the complexes of Structure I are in the order of $10^7$ or lower, including, but not limited to, lower than in the order of $7\times10^6$, $5\times10^6$, $3\times10^6$, $10^6$, $7\times10^5$, $5\times10^5$, $3\times10^5$, or $10^5$.

The effect of triplet-triplet annihilation in the devices is suppressed. As a result, the efficiency roll-off in the devices fabricated by using these complexes as emitting materials are low.

In one embodiment, the efficiency roll-off of the device at 1000 cd/A is less than 7%. In another embodiment, the efficiency roll-off of the device at 1000 cd/A is less than 20%, or any percentages lower than 20%, including, but not limited to, lower than 17%, 15%, 13%, 10%, 7%, 5%, or 3%.

Furthermore, due to the low self-quenching, higher doping concentration can be used to increase the device efficiency while the CIE can be kept as the excimer emission is avoided, or is substantially avoided.

In one embodiment, a device shows no, or almost no, excimer emission with 10% doping concentration.

As the complexes show emission from green to orange region, green to orange OLED can be fabricated by using the organometallic complex of Structure I as the single emitter. In an embodiment, a blue emitting material (or layer) is added to the orange device, and white OLED can be fabricated.

In one embodiment, the device fabricated using the organometallic complex of Structure I shows green emission with CIE of (0.25±0.05, 0.63±0.05).

In another embodiment, the device fabricated using the organometallic complex of Structure I shows yellow to orange emission with CIE of (0.40±0.1, 0.4±0.1).

Since the organometallic complexes of Structure I do not carry net charge and are soluble in common solvents, various device fabrication methods can be used in OLED fabrication.

The luminescent platinum(II) compounds of the present invention can be formed into thin films by vacuum deposition, spin-coating, inkjet printing or other known fabrication methods. Different multilayer OLEDs have been fabricated using the compounds of the present invention as light-emitting material or as dopant in the emitting layer. In general, the OLEDs consist on an anode and a cathode, between which are the hole transporting layer, light-emitting layer, and electron transporting or injection layer. The present invention makes use of an additional carrier confinement layer to improve the performance of the devices.

In one embodiment, the OLED is fabricated by vacuum deposition.

In another embodiment, the OLED is fabricated by solution process including spin coating and printing.

EXAMPLES

Following are examples that illustrate embodiments for practicing the invention. These examples should not be construed as limiting. All percentages are by weight and all solvent mixture proportions are by volume unless otherwise noted.

Example 1—Preparation of Precursor 261

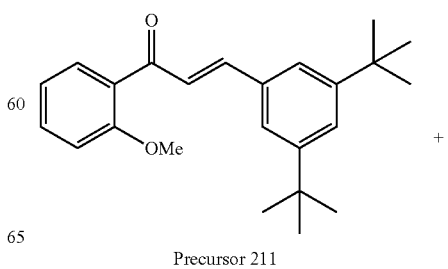

Precursor 211

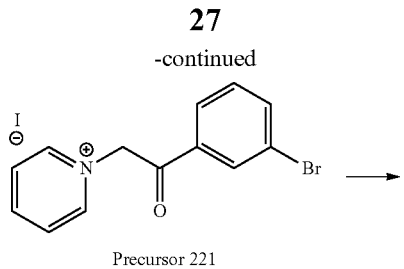

Precursor 221

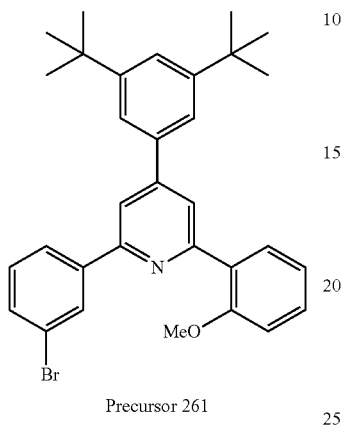

Precursor 261

To a conical flask was charged with Precursor 221 (2.24 g, 5.5 mmol), Precursor 211 (1.95 g, 5.5 mmol), excess ammonium acetate, and methanol. The mixture was refluxed for 24 h.

After cooling to room temperature, the solvent was evaporated. The crude mixture was extracted with dichloromethane and purified by chromatography on silica gel with mixture of hexane and ethyl acetate (v/v=10:1). 2.56 g of off-white solid was obtained. Yield: 88%. $^1$H NMR (CDCl$_3$, 400 MHz): δ 8.31 (s, 1H), 8.05-8.04 (m, 2H), 8.01 (d, J=7.6 Hz, 1H), 7.78 (s, 1H), 7.55-7.53 (m, 2H), 7.52 (s, 2H), 7.42 (t, J=7.3 Hz, 1H), 7.36 (t, J=7.9 Hz, 1H), 7.15 (t, J=7.5 Hz, 1H), 7.05 (d, J=8.2 Hz, 1H), 3.90 (s, 3H), 1.41 (s, 18H).

Example 2—Preparation of Precursor 271

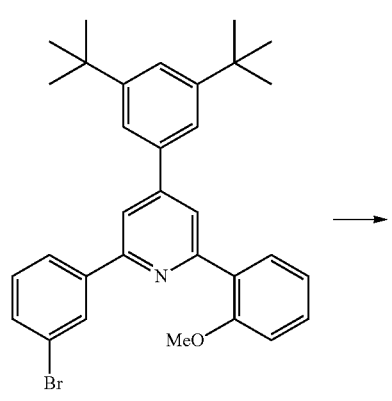

Precursor 261

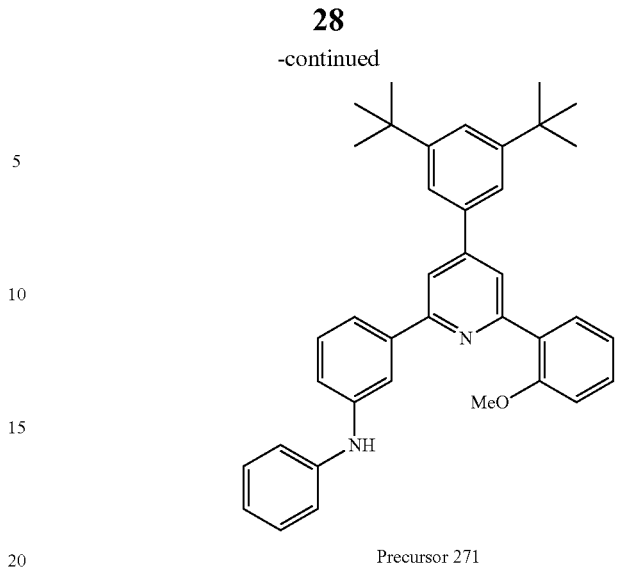

Precursor 271

To a dry, nitrogen-flushed flask was charged with Precursor 261 (1.44 g, 2.7 mmol), potassium tert-butoxide (0.42 g, 3.8 mmol), Pd(dba)$_2$ (0.25 g, 0.27 mmol), DPE-phos(bis[2-(diphenylphosphino)phenyl]ether) (0.29 g, 0.55 mmol), aniline (0.25 g, 2.7 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 1.31 g of yellow solid was obtained. Yield: 90%. $^1$H NMR (CDCl$_3$, 400 MHz): δ 8.03 (s, 2H), 7.88 (s, 1H), 7.79 (s, 1H), 7.62 (m, 1H), 7.53 (s, 3H), 7.42-7.39 (m, 2H), 7.38-7.36 (m, 1H), 7.30-7.28 (m, 2H), 7.13-7.11 (m, 2H), 7.05-7.03 (m, 2H), 6.93 (m, 1H), 5.86 (s, 1H), 3.89 (s, 3H), 1.40 (s, 18H).

Example 3—Preparation of Precursor 281

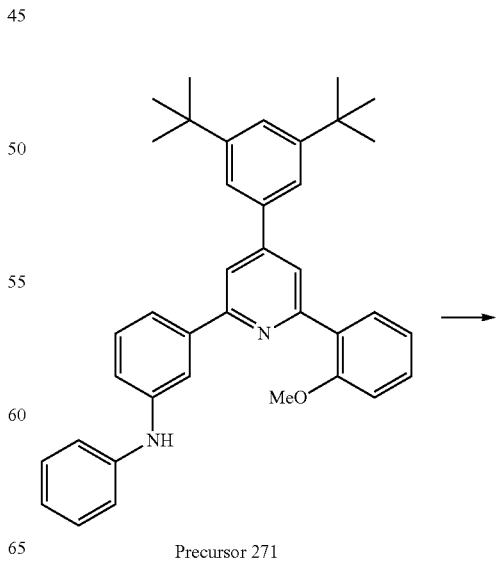

Precursor 271

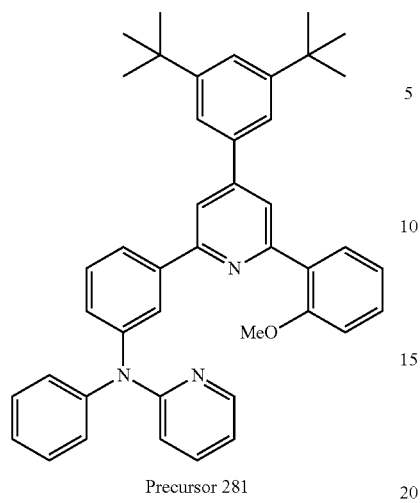

Precursor 281

To a dry, nitrogen-flushed flask was charged with Precursor 271 (1.31 g, 2.4 mmol), potassium tert-butoxide (0.33 g, 2.9 mmol), Pd(dba)$_2$ (0.22 g, 0.24 mmol), DPE-phos, 2-iodopyridine (0.26 g, 0.48 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 1.29 g of yellow solid was obtained. Yield: 87%. $^1$H NMR (CDCl$_3$, 400 MHz): δ 8.26 (d, J=4.92 Hz, 1H), 8.01 (s, 1H), 7.96 (d, J=7.6 Hz, 1H), 7.93-7.89 (m, 2H), 7.70 (s, 1H), 7.52 (t, J=1.97 Hz, 1H), 7.49 (s, 2H), 7.45-7.23 (m, 8H), 7.11 (q, J=7.5 Hz, 2H), 7.03 (d, J=8.2 Hz, 1H), 6.84 (d, J=8.4 Hz, 1H), 6.78-6.80 (m, 1H), 3.86 (s, 3H), 1.38 (s, 18H).

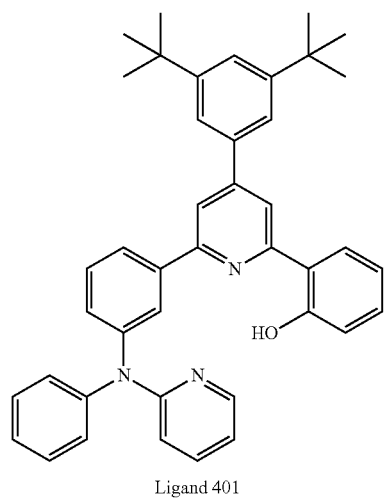

Ligand 401

To a dry, nitrogen-flushed flask was charged with Precursor 281 (1.29 g, 2.1 mmol) and pyridine hydrochloride. The mixture was refluxed for 24 h. After cooling to room temperature, the crude mixture was extracted with dichloromethane and purified by chromatography on silica gel with mixture of hexane and ethyl acetate (v/v=10:1). 1.2 g of yellow solid was obtained. Yield: 95%. $^1$H NMR (CD$_2$Cl$_2$, 500 MHz): δ 14.37 (s, 1H), 8.22 (d, J=4.9 Hz, 1H), 8.05 (s, 1H), 7.96 (d, J=8.1 Hz, 1H), 7.78 (s, 1H), 7.75 (d, J=7.7 Hz, 1H), 7.72 (s, 1H), 7.58 (s, 1H), 7.52-7.48 (m, 4H), 7.38-7.31 (m, 3H), 7.28-7.24 (m, 3H), 7.19 (t, J=5.8 Hz, 1H), 6.99 (d, J=8.3 Hz, 1H), 6.95 (t, J=7.5 Hz, 1H), 6.82-6.86 (m, 2H), 1.39 (s, 18H). MS (FAB): 604.1 (M$^+$)

Example 4—Preparation of Ligand 401

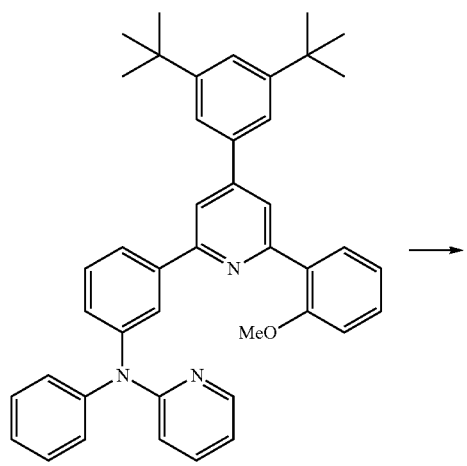

Precursor 281

Example 5—Preparation of Precursor 282

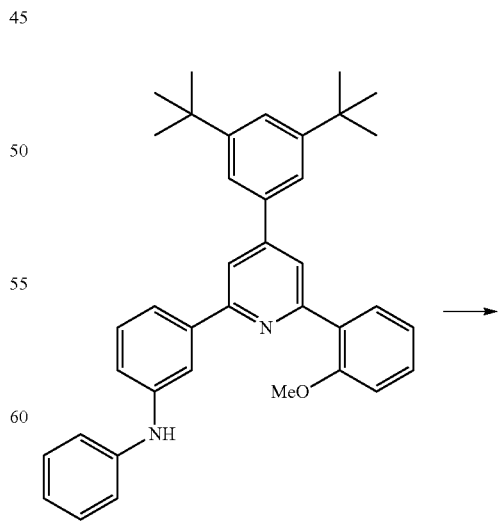

Precursor 271

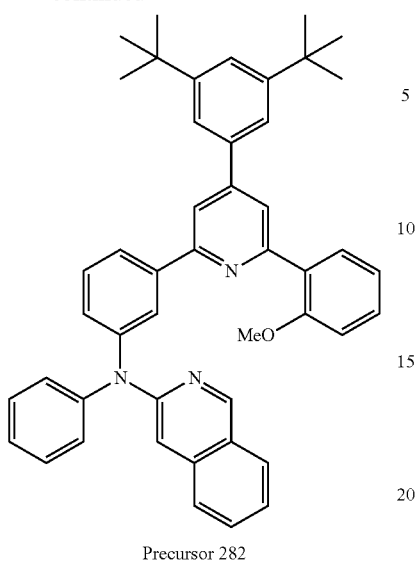

Precursor 282

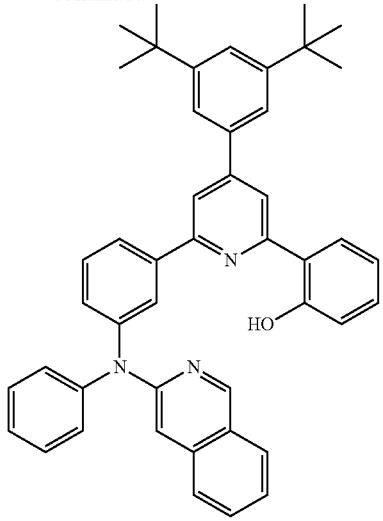

Ligand 402

To a dry, nitrogen-flushed flask was charged with Precursor 271 (0.20 g, 0.37 mmol), potassium tert-butoxide (0.05 g, 0.44 mmol), Pd(dba)$_2$ (0.03 g, 0.03 mmol), DPE-phos (0.04 g, 0.07 mmol), 3-bromoisoquinoline (0.08 g, 0.86 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.17 g of yellow solid was obtained. Yield: 69%. $^1$H NMR (CDCl$_3$, 300 MHz): δ 9.03 (s, 1H), 8.00 (s, 1H), 7.83-7.96 (m, 4H), 7.69 (s, 1H), 7.53-7.45 (m, 6H), 7.39-7.30 (m, 5H), 7.25-7.23 (m, 2H), 7.15-7.02 (m, 4H), 3.85 (s, 3H), 1.37 (s, 18H).

Example 6—Preparation of Ligand 402

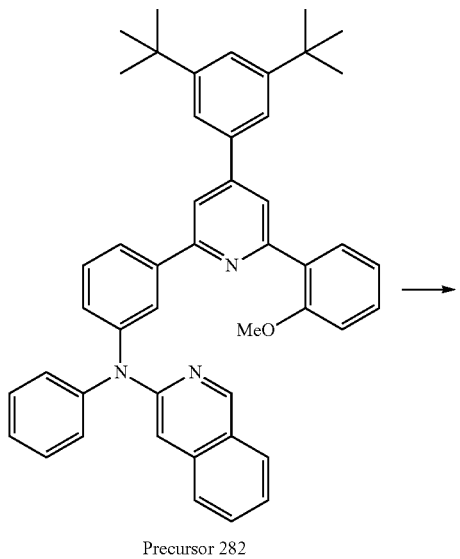

Precursor 282

To a dry, nitrogen-flushed flask was charged with Precursor 282 (0.13 g, 0.19 mmol) and pyridine hydrochloride. The mixture was refluxed for 24 h. After cooling to room temperature, the crude mixture was extracted with dichloromethane and purified by chromatography on silica gel with mixture of hexane and ethyl acetate (v/v=10:1). 0.11 g of yellow solid was obtained. Yield: 90%. $^1$H NMR (CD$_2$Cl$_2$, 400 MHz): δ14.67 (s, 1H), 9.04 (s, 1H), 7.97 (s, 1H), 7.89-7.84 (m, 2H), 7.73-7.71 (m, 2H), 7.63 (s, 1H), 7.55-7.53 (m, 3H), 7.47-7.44 (m, 3H), 7.38-7.26 (m, 7H), 7.17-7.15 (m, 2H), 7.02 (d, J=8.1 Hz, 1H), 6.94 (t, J=8.1 Hz, 1H), 1.38 (s, 18H).

Example 7—Preparation of Precursor 253

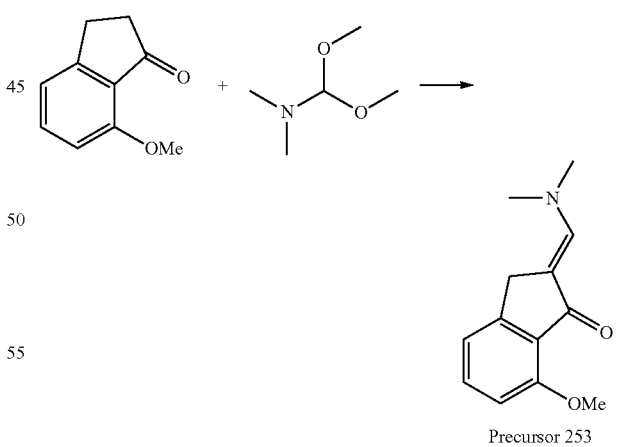

Precursor 253

To a conical flask was charged with 7-methoxy-1-indanone (2.18 g, 13.4 mmol), 1,1-dimethoxy-N,N-dimethylmethanamine. The mixture was refluxed for 24 h. After cooling to room temperature, the solvent was evaporated. The crude mixture was purified by chromatography on silica gel with mixture of hexane and ethyl acetate (v/v=10:1). 2.42 g of brown solid was obtained. Yield: 83%. $^1$H NMR (CDCl$_3$, 300 MHz): δ 7.42-7.37 (m, 2H), 7.00 (d, J=7.5 Hz, 1H), 6.79 (d, J=8.2 Hz, 1H), 3.95 (s, 3H), 3.85 (s, 2H), 3.14 (s, 6H).

Example 8—Preparation of Precursor 263

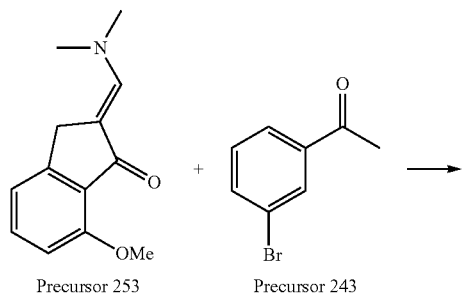

Precursor 253    Precursor 243

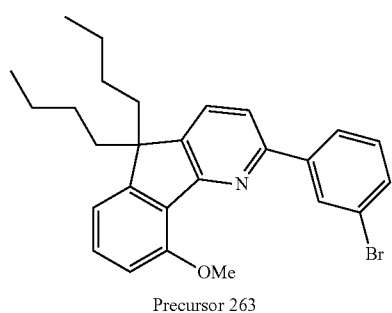

Precursor 263

To a dry, nitrogen-flushed flask was charged with Precursor 253 (2.18 g, 10.0 mmol), Precursor 243 (1.99 g, 10.0 mmol), potassium tert-butoxide (1.35 g, 12.0 mmol), anhydrous THF. The mixture was stirred for 12 h. Excess ammonium acetate, acidic acid was added. The mixture was refluxed for 2 h. After cooling to room temperature, the crude mixture was extracted with ethyl acetate and an intermediate was purified by chromatography on silica gel with mixture of hexane and ethyl acetate (v/v=10:1). To a dry, nitrogen-flushed flask was charged the intermediate prepared above (0.53 g, 1.5 mmol), potassium tert-butoxide (0.37 g, 3.3 mmol), 1-iodobutane (0.38 mL, 3.3 mmol), and anhydrous THF. The mixture was stirred for 24 h. The crude mixture was extracted with ethyl acetate and purified by chromatography on silica gel with mixture of hexane and ethyl acetate (v/v=10:1). 0.60 g of yellow solid was obtained. Yield: 77%. $^1$H NMR (CDCl$_3$, 400 MHz): δ 8.38 (s, 1H), 8.10 (d, J=7.8 Hz, 1H), 7.63 (q, J=7.9 Hz, 2H), 7.51 (d, J=8.0 Hz, 1H), 7.42-7.32 (m, 2H), 7.00 (d, J=7.6 Hz, 1H), 6.93 (d, J=8.0 Hz, 1H), 4.11 (s, 3H), 2.01-1.96 (s, 4H), 1.10-1.02 (m, 4H), 0.67-0.57 (m, 10H).

Example 9—Preparation of Precursor 273

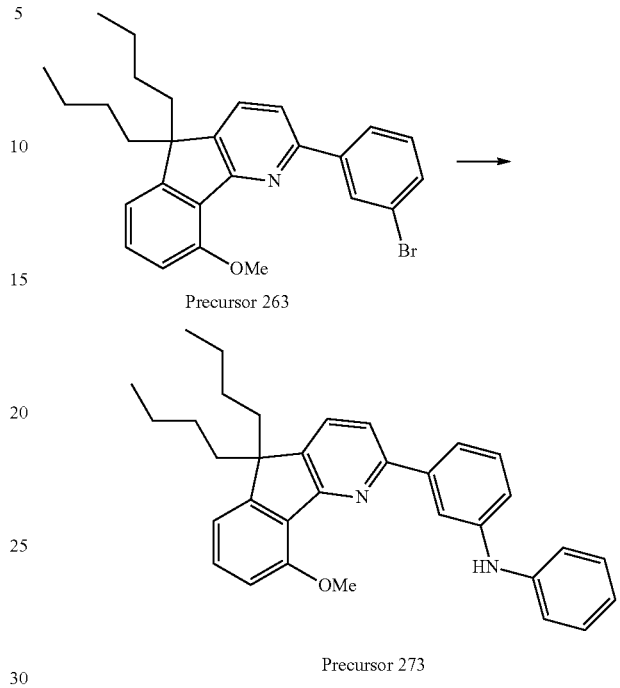

Precursor 263

Precursor 273

To a dry, nitrogen-flushed flask was charged with Precursor 263 (0.54 g, 1.2 mmol), potassium tert-butoxide (0.16 g, 1.4 mmol), Pd(dba)$_2$ (0.11 g, 0.12 mmol), DPE-phos(bis[2-(diphenylphosphino)phenyl]ether) (0.13 g, 0.23 mmol), aniline (0.11 g, 1.2 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.41 g of yellow solid was obtained. Yield: 74%. $^1$H NMR (CDCl$_3$, 300 MHz): δ 8.00 (s, 1H), 7.69 (d, J=7.8 Hz, 1H), 7.62 (s, 2H), 7.41-7.33 (m, 3H), 7.30 (s, 1H), 7.15-7.13 (m, 3H), 7.00-6.90 (m, 3H), 5.82 (s, 1H), 4.05 (s, 3H), 2.00-1.95 (m, 4H), 1.10-1.02 (m, 4H), 0.67-0.57 (m, 10H).

Example 10—Preparation of Precursor 283

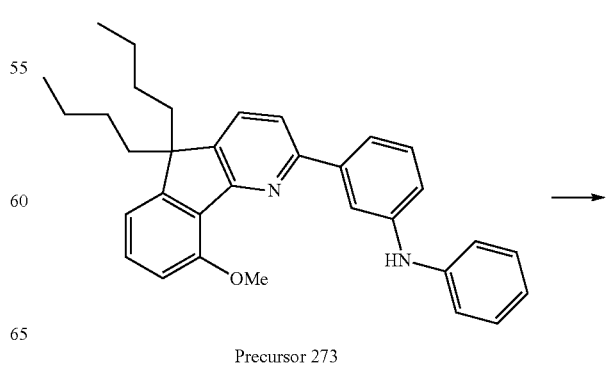

Precursor 273

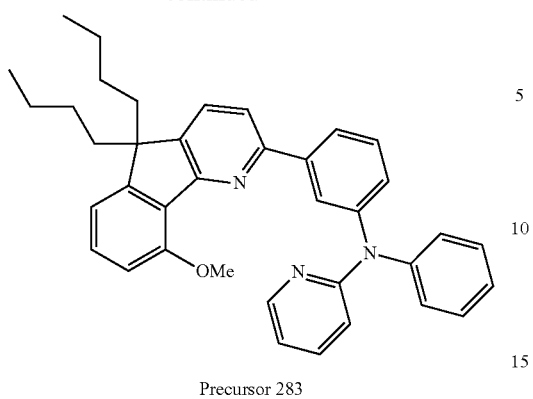

Precursor 283

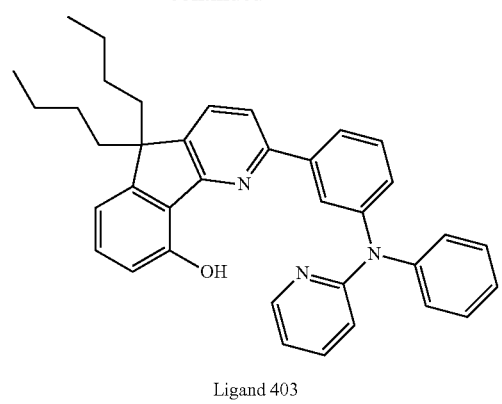

Ligand 403

To a dry, nitrogen-flushed flask was charged with Precursor 273 (0.41 g, 0.86 mmol), potassium tert-butoxide (0.12 g, 1.03 mmol), Pd(dba)$_2$ (0.08 g, 0.086 mmol), DPE-phos (0.09 g, 0.17 mmol), 2-iodopyridine (0.18 g, 0.86 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.43 g of yellow solid was obtained. Yield: 90%. $^1$H NMR (CDCl$_3$, 400 MHz): δ8.26 (d, J=7.7 Hz, 1H), 8.05 (s, 1H), 7.93 (d, J=7.9 Hz, 1H), 7.60 (d, J=7.8 Hz, 2H), 7.55 (d, J=8.0 Hz, 1H), 7.45 (q, J=8.3 Hz, 2H), 7.38-7.30 (m, 4H), 7.23-7.20 (m, 2H), 7.11 (t, J=7.0 Hz, 1H), 6.97 (d, J=7.5 Hz, 1H), 6.85 (d, J=8.0 Hz, 1H), 6.81 (d, J=7.7 Hz, 1H), 6.78 (t, J=6.5 Hz, 1H), 3.95 (s, 3H), 1.97-1.55 (m, 4H), 1.07-1.00 (m, 4H), 0.65-0.53 (m, 10H).

To a dry, nitrogen-flushed flask was charged with Precursor 283 (0.43 g, 0.77 mmol) and pyridine hydrochloride. The mixture was refluxed for 24 h. After cooling to room temperature, the crude mixture was extracted with dichloromethane and purified by chromatography on silica gel with mixture of hexane and ethyl acetate (v/v=10:1). 0.387 g of yellow solid was obtained. Yield: 90%. $^1$H NMR (CD$_2$Cl$_2$, 500 MHz): δ 9.17 (s, 1H), 8.21 (d, J=5.2 Hz, 1H), 7.83 (s, 1H), 7.79 (d, J=8.0 Hz, 1H), 7.68 (d, J=7.9 Hz, 1H), 7.54 (d, J=7.9 Hz, 1H), 7.50 (t, J=7.8 Hz, 1H), 7.45 (t, J=7.9 Hz, 1H), 7.36 (t, J=7.9 Hz, 2H), 7.31 (t, J=7.9 Hz, 1H), 7.25-7.21 (m, 3H), 7.18 (t, J=7.4 Hz, 1H), 6.93 (d, J=7.3 Hz, 1H), 6.84-6.82 (m, 3H), 1.97-1.92 (m, 4H), 1.10-1.06 (m, 4H), 0.71-0.66 (m, 10H). MS(FAB): 540.3 (M$^+$).

Example 11—Preparation of Ligand 403

Example 12—Preparation of Precursor 284

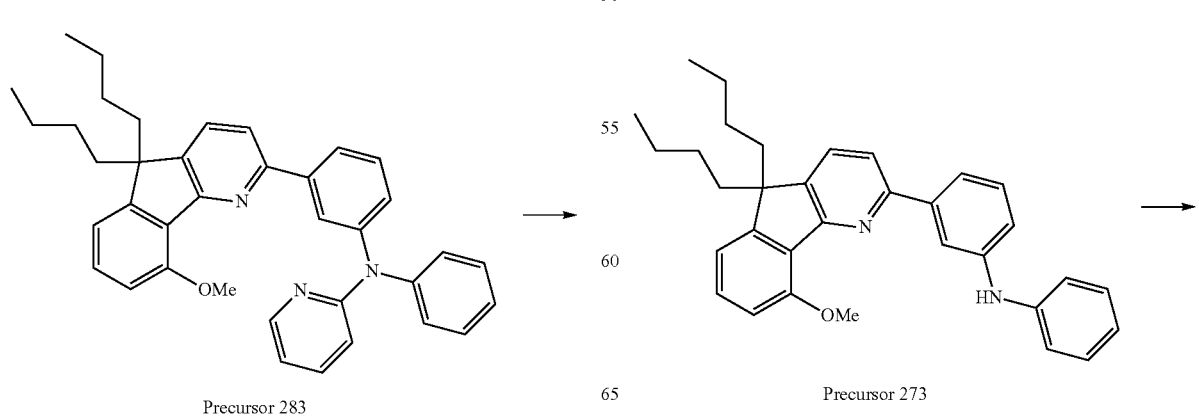

Precursor 283 → Precursor 273 →

37

-continued

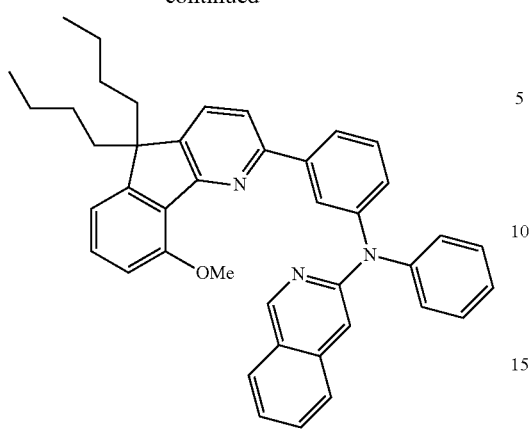

Precursor 284

To a dry, nitrogen-flushed flask was charged with Precursor 273 (0.21 g, 0.44 mmol), potassium tert-butoxide (0.06 g, 0.52 mmol), Pd(dba)$_2$ (0.04 g, 0.04 mmol), DPE-phos (0.05 g, 0.08 mmol), 3-bromoisoquinoline (0.09 g, 0.44 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.17 g of yellow solid was obtained. Yield: 65%. $^1$H NMR (CDCl$_3$, 400 MHz): δ 9.03 (s, 1H), 8.05 (s, 1H), 7.95 (d, J=7.6 Hz, 1H), 7.84 (d, J=8.1 Hz, 1H), 7.60-7.50 (m, 5H), 7.46 (t, J=7.9 Hz, 1H), 7.37-7.31 (m, 5H), 7.25-7.23 (m, 2H), 7.12 (s, 1H), 6.96 (d, J=7.4 Hz, 1H), 6.84 (d, J=8.1 Hz, 1H), 3.84 (s, 3H), 1.97-1.92 (m, 4H), 1.06-1.01 (m, 4H), 0.64-0.57 (m, 10H).

Example 13—Preparation of Ligand 404

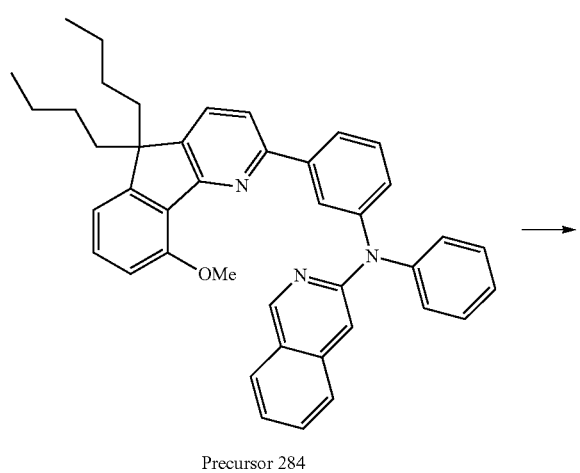

Precursor 284

38

-continued

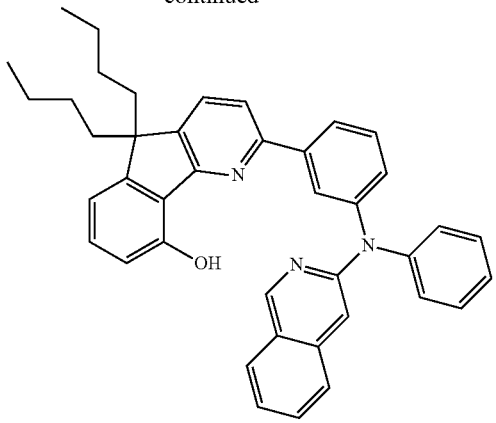

Ligand 404

To a dry, nitrogen-flushed flask was charged with Precursor 284 (0.17 g, 0.28 mmol) and pyridine hydrochloride. The mixture was refluxed for 24 h. After cooling to room temperature, the crude mixture was extracted with dichloromethane and purified by chromatography on silica gel with mixture of hexane and ethyl acetate (v/v=10:1). 0.15 g of yellow solid was obtained. Yield: 90%. $^1$H NMR (CDCl$_3$, 300 MHz): δ 9.31 (s, 1H), 9.04 (s, 1H), 7.86 (d, J=8.5 Hz, 1H), 7.80 (s, 2H), 7.54-7.45 (m, 5H), 7.42-7.31 (m, 3H), 7.29-7.23 (m, 4H), 7.15 (s, 2H), 6.87 (t, J=8.7 Hz, 2H), 1.96-1.91 (m, 4H), 1.05-1.00 (m, 4H), 0.70-0.65 (m, 10H). MS(ESI): 590.3 (M$^+$).

Example 14—Preparation of Precursor 265

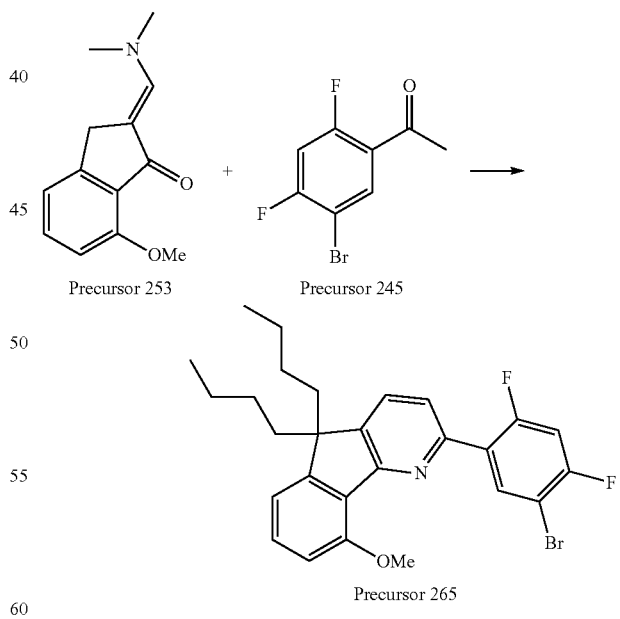

Precursor 265

To a dry, nitrogen-flushed flask was charged with Precursor 253 (0.50 g, 2.3 mmol), Precursor 245 (0.54 g, 2.3 mmol), potassium tert-butoxide (0.31 g, 2.7 mmol), anhydrous THF. The mixture was stirred for 12 h. Excess ammonium acetate, acidic acid was added. The mixture was refluxed for 2 h. After cooling to room temperature, the crude mixture of the intermediate was extracted with ethyl acetate and purified by chromatography on silica gel with mixture of hexane and ethyl acetate (v/v=10:1).

To a dry, nitrogen-flushed flask was the above intermediate (0.90 g, 2.3 mmol), potassium tert-butoxide (0.57 g, 5.1 mmol), 1-iodobutane (0.58 mL, 5.1 mmol), and anhydrous THF. The mixture was stirred for 24 h. The crude mixture was extracted with ethyl acetate and purified by chromatography on silica gel with mixture of hexane and ethyl acetate (v/v=10:1). 1.04 g of yellow solid was obtained. Yield: 81%. $^1$H NMR (CDCl$_3$, 400 MHz): δ 8.65 (t, J=8.1 Hz, 1H), 7.70 (d, J=7.9 Hz, 1H), 7.65 (d, J=7.8 Hz, 1H), 7.41 (t, J=8.0 Hz, 1H), 7.02-6.94 (m, 3H), 4.11 (s, 3H), 2.02-1.96 (m, 4H), 1.10-1.04 (m, 4H), 0.68-0.56 (m, 10H).

Example 15—Preparation of Precursor 275

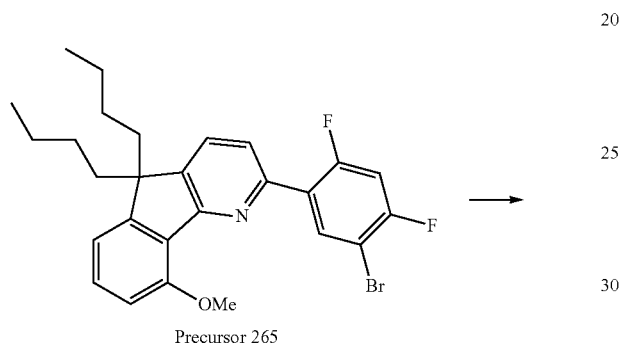

Precursor 265

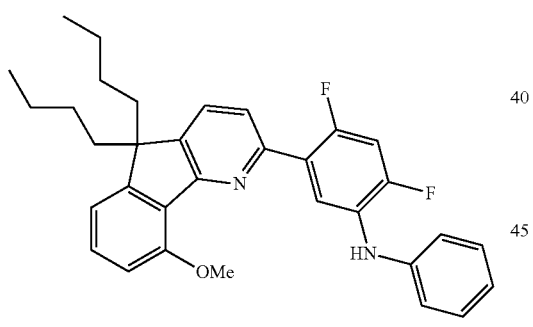

Precursor 275

To a dry, nitrogen-flushed flask was charged with Precursor 265 (1.22 g, 2.4 mmol), potassium phosphate (0.78 g, 3.6 mmol), Pd(dba)$_2$ (0.22 g, 0.2 mmol), DPE-phos(bis[2-(diphenylphosphino)phenyl]ether) (0.26 g, 0.5 mmol), aniline (0.23 g, 2.4 mmol), and toluene/water mixture. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.76 g of yellow solid was obtained. Yield: 61%. $^1$H NMR (CDCl$_3$, 400 MHz): δ 8.39 (t, J=8.1 Hz, 1H), 7.72 (d, J=6.5 Hz, 1H), 7.62 (d, J=7.9 Hz, 1H), 7.39-7.30 (m, 3H), 7.17 (d, J=8.5 Hz, 2H), 7.00-6.96 (m, 3H), 6.88 (d, J=8.1 Hz, 1H), 3.92 (s, 3H), 2.00-1.94 (m, 4H), 1.09-1.03 (m, 4H), 0.67-0.58 (m, 10H).

Example 16—Preparation of Precursor 285

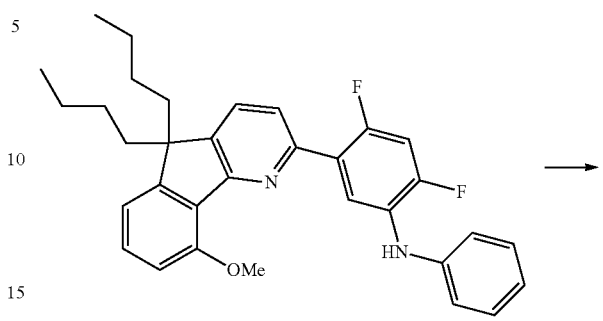

Precursor 275

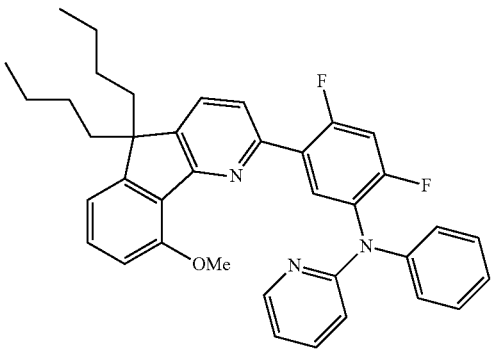

Precursor 285

To a dry, nitrogen-flushed flask was charged with Precursor 275 (0.77 g, 1.5 mmol), potassium tert-butoxide (0.20 g, 1.8 mmol), Pd(dba)$_2$ (0.14 g, 0.2 mmol), DPE-phos (0.16 g, 0.3 mmol), 2-iodopyridine (0.31 g, 1.5 mmol), and anhydrous toluene. The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.49 g of yellow solid was obtained. Yield: 55%. $^1$H NMR (CDCl$_3$, 400 MHz): δ 8.13 (d, J=8.5 Hz, 1H), 8.10 (d, J=8.2 Hz, 1H), 7.62-7.57 (m, 2H), 7.44 (m, 1H), 7.36-7.31 (m, 3H), 7.29-7.25 (m, 2H), 7.16 (t, J=7.2 Hz, 1H), 7.00 (d, J=10.7 Hz, 1H), 6.94 (d, J=7.5 Hz, 1H), 6.81 (d, J=8.0 Hz, 1H), 6.75-6.70 (m, 2H), 3.74 (s, 3H), 1.94-1.88 (m, 4H), 1.03-0.97 (m, 4H), 0.60-0.48 (m, 10H).

Example 17—Preparation of Ligand 405

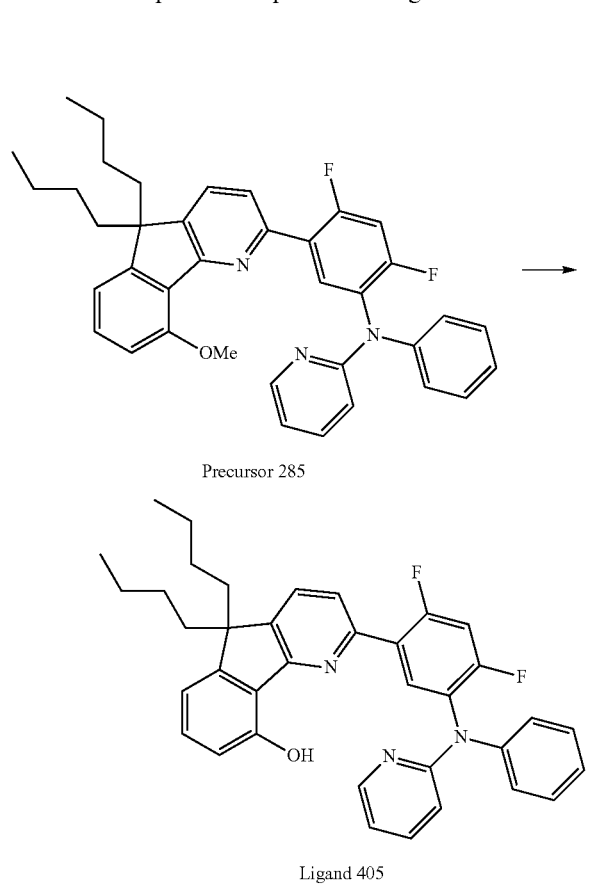

Precursor 285

Ligand 405

To a dry, nitrogen-flushed flask was charged with Precursor 285 (0.22 g, 0.3 mmol) and BBr$_3$ (0.4 mL, 3.0 mmol). The mixture was stirred for 3 h. Water was added to quench the reaction. The crude mixture was extracted with dichloromethane and purified by chromatography on silica gel with mixture of hexane and ethyl acetate (v/v=10:1). 0.18 g of yellow solid was obtained. Yield: 85%. $^1$H NMR (CDCl$_3$, 400 MHz): δ 8.87 (s, 1H), 8.12 (s, 1H), 7.82 (t, J=8.5 Hz, 1H), 7.66 (d, J=7.9 Hz, 1H), 7.56 (d, J=7.6 Hz, 1H), 7.44 (t, J=6.8 Hz, 1H), 7.37-7.15 (m, 5H), 7.03 (t, J=8.5 Hz, 2H), 6.89 (d, J=7.4 Hz, 1H), 7.78-7.72 (m, 3H), 1.98-1.89 (m, 4H), 1.08-1.01 (m, 4H), 0.66-0.58 (m, 10H).

Example 18—Preparation of Precursor 266

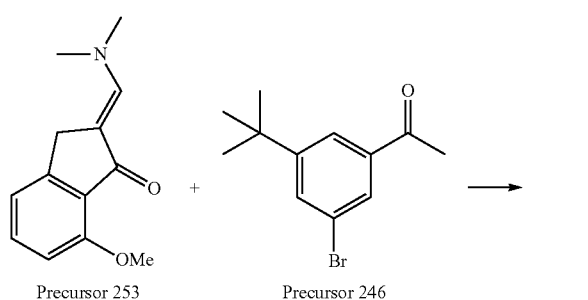

Precursor 253  Precursor 246

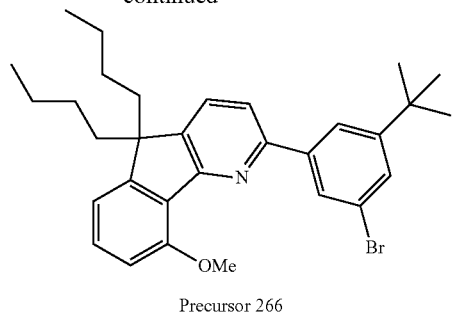

Precursor 266

To a dry, nitrogen-flushed flask was charged with Precursor 253 (1.21 g, 5.6 mmol), Precursor 246 (1.42 g, 5.6 mmol), potassium tert-butoxide (0.75 g, 6.6 mmol), anhydrous THF. The mixture was stirred for 12 h. Excess ammonium acetate, acidic acid was added. The mixture was refluxed for 2 h. After cooling to room temperature, the crude mixture of the intermediate was extracted with ethyl acetate and purified by chromatography on silica gel with mixture of hexane and ethyl acetate (v/v=10:1).

To a dry, nitrogen-flushed flask was charged with the intermediate above (0.67 g, 1.6 mmol), potassium tert-butoxide (0.41 g, 3.6 mmol), 1-iodobutane (0.41 mL, 3.6 mmol), and anhydrous THF (20 mL). The mixture was stirred for 24 h. The crude mixture was extracted with ethyl acetate and purified by chromatography on silica gel with mixture of hexane and ethyl acetate (v/v=10:1). 0.80 g of yellow solid was obtained. Yield: 72%. $^1$H NMR (CDCl$_3$, 400 MHz): δ 8.29 (s, 1H), 8.06 (s, 1H), 7.63 (q, J=6.8 Hz, 2H), 7.53 (s, 1H), 7.39 (t, J=7.8 Hz, 1H), 7.00 (d, J=7.4 Hz, 1H), 6.92 (d, J=8.1 Hz, 1H), 4.10 (s, 3H), 2.00-1.97 (m, 4H), 1.40 (s, 9H), 1.09-1.03 (m, 4H), 0.66-0.57 (m, 10H).

Example 19—Preparation of Precursor 276

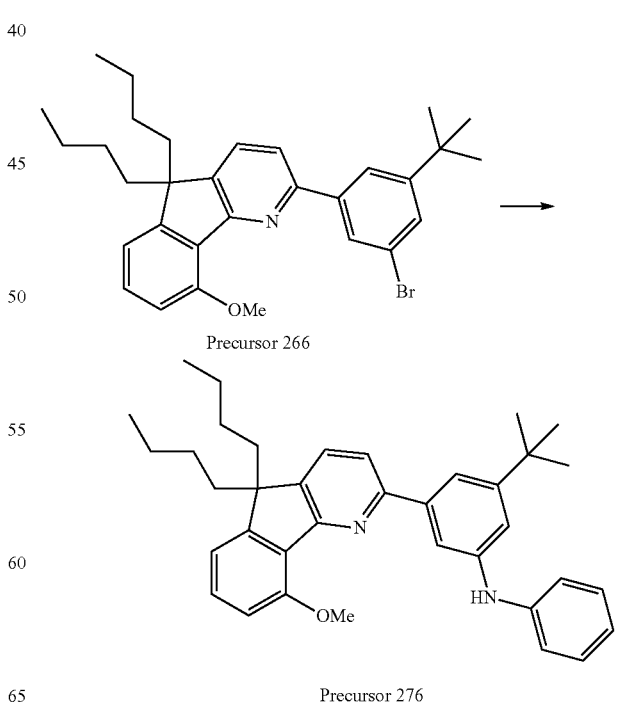

Precursor 266

Precursor 276

To a dry, nitrogen-flushed flask was charged with Precursor 266 (0.80 g, 1.5 mmol), potassium tert-butoxide (0.21 g, 1.8 mmol), Pd(dba)$_2$ (0.14 g, 0.2 mmol), DPE-phos(bis[2-(diphenylphosphino)phenyl]ether) (0.17 g, 0.3 mmol), aniline (0.16 g, 1.5 mmol), and anhydrous toluene (20 mL). The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.66 g of yellow solid was obtained. Yield: 81%. $^1$H NMR (CDCl$_3$, 400 MHz): δ 7.91 (s, 1H), 7.74 (s, 1H), 7.59 (s, 2H), 7.36 (t, J=7.9 Hz, 1H), 7.29-7.27 (m, 2H), 7.13 (t, J=8.6 Hz, 3H), 6.98 (d, J=7.5 Hz, 1H), 6.92-6.90 (m, 2H), 4.06 (s, 3H), 1.99-1.94 (m, 4H), 1.40 (s, 9H), 1.09-1.04 (m, 4H), 0.67-0.62 (m, 10H).

Example 20—Preparation of Precursor 286

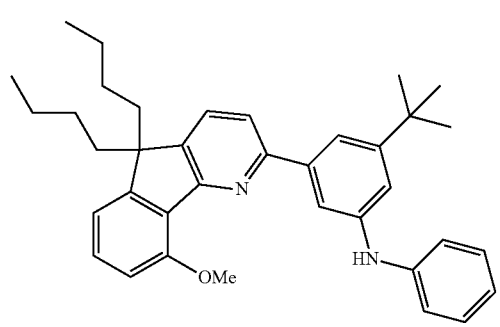

Precursor 276

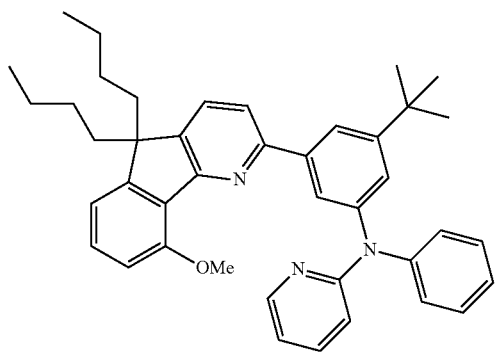

Precursor 286

To a dry, nitrogen-flushed flask was charged with Precursor 276 (0.65 g, 1.2 mmol), potassium tert-butoxide (0.17 g, 1.5 mmol), Pd(dba)$_2$ (0.11 g, 0.1 mmol), DPE-phos (0.13 g, 0.2 mmol), 2-iodopyridine (0.30 g, 1.2 mmol), and anhydrous toluene (20 mL). The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.65 g of yellow solid was obtained. Yield: 86%. $^1$H NMR (CDCl$_3$, 400 MHz): δ 8.24 (d, J=4.5 Hz, 1H), 8.13 (s, 1H), 7.73 (s, 1H), 7.58 (d, J=7.9 Hz, 1H), 7.52 (d, J=7.9 Hz, 1H), 7.44 (t, J=7.0 Hz, 1H), 7.36 (t, J=7.8 Hz, 1H), 7.30 (t, J=8.3 Hz, 2H), 7.25-7.22 (m, 3H), 7.10 (t, J=7.2 Hz, 1H), 6.97 (d, J=7.8 Hz, 1H), 6.88 (d, J=8.1 Hz, 1H), 6.81-6.75 (m, 2H), 3.99 (s, 3H), 1.98-1.93 (m, 4H), 1.36 (s, 9H), 1.07-1.02 (m, 4H), 0.65-0.55 (m, 10H).

Example 21—Preparation of Ligand 406

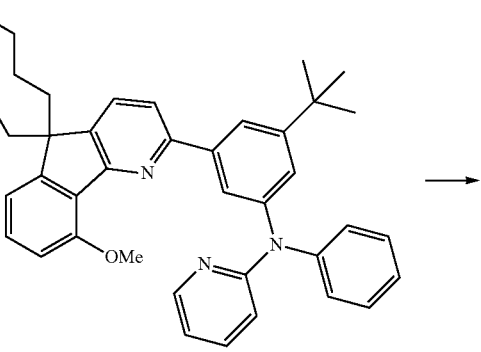

Precursor 286

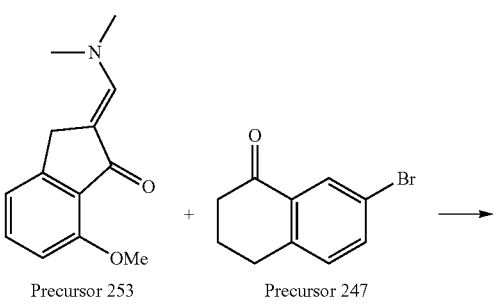

Ligand 406

To a dry, nitrogen-flushed flask was charged with Precursor 286 (0.65 g, 1.1 mmol) and pyridine hydrochloride (5 g). The mixture was refluxed for 24 h. After cooling to room temperature, the crude mixture was extracted with dichloromethane and purified by chromatography on silica gel with mixture of hexane and ethyl acetate (v/v=10:1). 0.59 g of yellow solid was obtained. Yield: 94%. $^1$H NMR (CDCl$_3$, 400 MHz): δ 9.19 (s, 1H), 8.14 (s, 1H), 7.78 (s, 1H), 7.61 (d, J=7.8 Hz, 1H), 7.53 (s, 1H), 7.47-7.42 (m, 2H), 7.30-7.24 (m, 4H), 7.24-7.16 (m, 2H), 7.11-7.09 (m, 1H), 6.87 (d, J=8.0 Hz, 1H), 6.75 (d, J=7.9 Hz, 3H), 1.94-1.89 (m, 4H), 1.29 (s, 9H), 1.06-1.01 (m, 4H), 0.65-0.59 (m, 10H).

Example 22—Preparation of Precursor 267

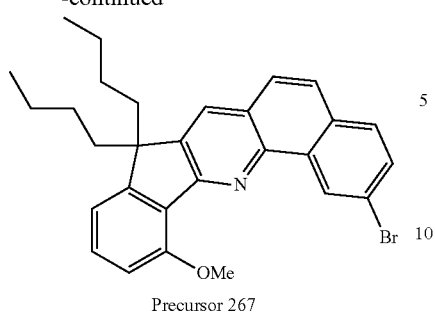

Precursor 267

To a dry, nitrogen-flushed flask was charged with Precursor 253 (1.97 g, 9.0 mmol), Precursor 247 (2.04 g, 9.0 mmol), potassium tert-butoxide (1.22 g, 10.9 mmol), anhydrous THF (40 mL). The mixture was stirred for 12 h. Excess ammonium acetate, acidic acid was added. The mixture was refluxed for 2 h. After cooling to room temperature, the crude mixture of the first intermediate was extracted with ethyl acetate and purified by chromatography on silica gel with mixture of hexane and ethyl acetate (v/v=10:1).

To a dry, nitrogen-flushed flask was charged the first intermediate (0.53 g, 1.4 mmol), potassium tert-butoxide (0.35 g, 3.1 mmol), 1-iodobutane (0.35 mL, 3.1 mmol), and anhydrous THF (20 mL). The mixture was stirred for 24 h. The crude mixture of the second intermediate was extracted with ethyl acetate and purified by chromatography on silica gel with mixture of hexane and ethyl acetate (v/v=10:1).

To a dry, nitrogen-flushed flask was charged with the second intermediate (0.64 g, 1.3 mmol), 4,5-dichloro-3,6-dioxocyclohexa-1,4-diene-1,2-dicarbonitrile(DDQ) (0.42 g, 1.8 mmol), and anhydrous 1,4-dioxane (40 mL). The mixture was refluxed for 24 h. After cooling to room temperature, ethyl acetate was added, and the mixture was stirred for five minutes. The crude mixture was extracted with saturated sodium dicarbonate solution, dichloromethane and purified by chromatography on silica gel with mixture of hexane and ethyl acetate (v/v=10:1). 0.61 g of yellow solid was obtained. Yield: 79.5%. $^1$H NMR (CDCl$_3$, 400 MHz): δ 9.62 (s, 1H), 8.00 (s, 1H), 7.77-7.75 (m, 4H), 7.48 (t, J=7.9 Hz, 1H), 7.06 (d, J=7.5 Hz, 1H), 6.99 (d, J=8.1 Hz, 1H), 4.23 (s, 3H), 2.17-2.00 (m, 4H), 1.08-1.03 (m, 4H), 0.67-0.57 (m, 10H).

Example 23—Preparation of Precursor 277

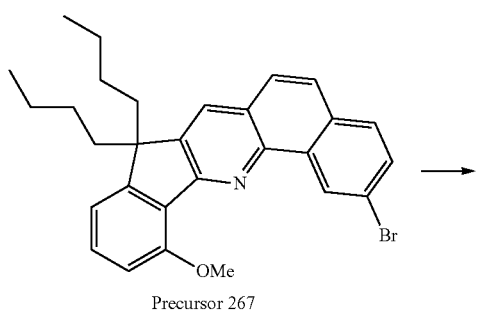

Precursor 267

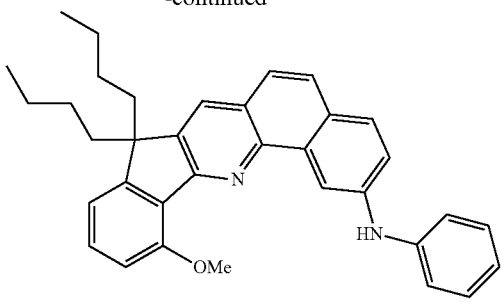

Precursor 277

To a dry, nitrogen-flushed flask was charged with Precursor 267 (0.61 g, 1.2 mmol), potassium tert-butoxide (0.17 g, 1.5 mmol), Pd(dba)$_2$ (0.11 g, 0.1 mmol), DPE-phos(bis[2-(diphenylphosphino)phenyl]ether) (0.13 g, 0.2 mmol), aniline (0.13 g, 1.2 mmol), and anhydrous toluene (20 mL). The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.51 g of yellow solid was obtained. Yield: 83%. $^1$H NMR (CDCl$_3$, 300 MHz): δ 9.15 (s, 1H), 7.96 (s, 1H), 7.80 (d, J=8.5 Hz, 1H), 7.70 (d, J=8.7 Hz, 1H), 7.55 (d, J=8.7 Hz, 1H), 7.46-7.30 (m, 6H), 7.04 (d, J=7.5 Hz, 2H), 6.95 (d, J=8.2 Hz, 1H), 6.09 (s, 1H), 4.09 (s, 3H), 2.08-2.04 (m, 4H), 1.07-1.02 (m, 4H), 0.65-0.58 (m, 10H).

Example 24—Preparation of Precursor 287

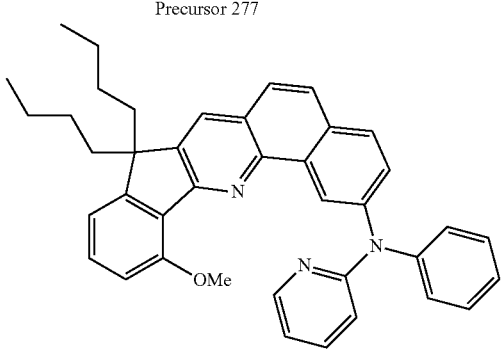

Precursor 277

Precursor 287

To a dry, nitrogen-flushed flask was charged with Precursor 277 (0.51 g, 1.0 mmol), potassium tert-butoxide (0.14 g, 1.2 mmol), Pd(dba)₂ (0.09 g, 0.1 mmol), DPE-phos (0.11 g, 0.2 mmol), 2-iodopyridine (0.23 g, 1.0 mmol), and anhydrous toluene (20 mL). The mixture was refluxed for 24 h. After cooling to room temperature, ethyl acetate was added, and the mixture was stirred for five minutes. The crude mixture was extracted with ethyl acetate and purified by chromatography on silica gel with mixture of hexane and ethyl acetate (v/v=10:1). 0.52 g of yellow solid was obtained. Yield: 89%. ¹H NMR (CDCl₃, 400 MHz): δ 9.24 (s, 1H), 8.30 (s, 1H), 7.95 (s, 1H), 7.85 (d, J=8.5 Hz, 1H), 7.74 (d, J=8.7 Hz, 1H), 7.54 (d, J=8.6 Hz, 1H), 7.51 (t, J=8.3 Hz, 2H), 7.42-7.31 (m, 5H), 7.17 (m, 1H), 7.01 (d, J=7.5 Hz, 1H), 6.91 (t, J=8.3 Hz, 2H), 6.85 (t, J=8.0 Hz, 1H), 3.89 (s, 3H), 2.09-2.04 (m, 4H), 1.08-1.00 (m, 4H), 0.65-0.54 (m, 10H).

Example 25—Preparation of Ligand 407

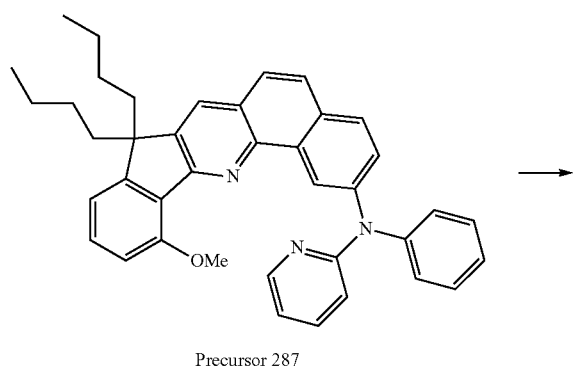

Precursor 287

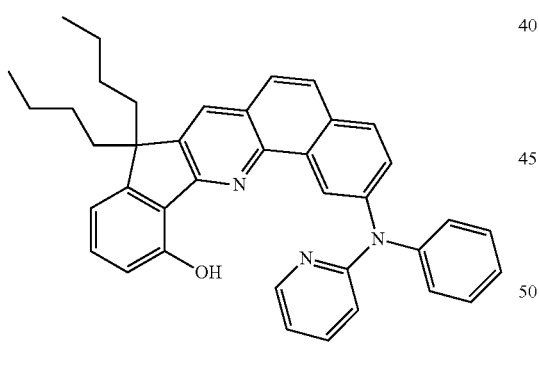

Ligand 407

To a dry, nitrogen-flushed flask was charged with Precursor 287 (0.52 g, 0.9 mmol) and pyridine hydrochloride (5 g). The mixture was refluxed for 24 h. After cooling to room temperature, the crude mixture was extracted with dichloromethane and purified by chromatography on silica gel with mixture of hexane and ethyl acetate (v/v=10:1). 0.48 g of yellow solid was obtained. Yield: 95%. ¹H NMR (CDCl₃, 400 MHz): δ 9.39 (s, 1H), 8.90 (s, 1H), 8.30 (s, 1H), 7.99 (s, 1H), 7.88 (d, J=8.5 Hz, 1H), 7.77 (d, J=8.7 Hz, 1H), 7.67 (d, J=8.6 Hz, 1H), 7.57 (d, J=8.5 Hz, 1H), 7.51 (t, J=7.0 Hz, 1H), 7.42-7.30 (m, 5H), 7.23 (s, 1H), 6.94-6.85 (m, 4H), 2.08-2.01 (m, 4H), 1.12-1.06 (m, 4H), 0.71-0.64 (m, 10H).

Example 26—Preparation of Precursor 228

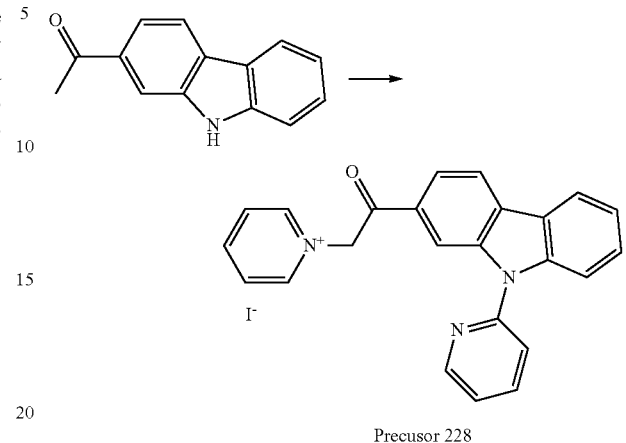

Precusor 228

A mixture of 2-acetylcarbazole, copper powder and potassium carbonate was degassed by three pump-fill cycles. To the solid mixture was added 50 mL DMF and 2-iodopyridine. The mixture was heated to 130° C. overnight. After cooling down to room temperature, dichloromethane was added to the mixture and filtered through celite. The organic solvent was extracted with water and dried with magnesium sulfate. The crude 1-(9-(pyridin-2-yl)carbazol-2-yl)ethanone was then purified by column chromatography using dichloromethane as eluent. The product was obtained as an off-white solid.

To a mixture of 1-(9-(pyridin-2-yl)carbazol-2-yl)ethanone and iodide was added 10 mL pyridine. The mixture was heated at 90° C. overnight. The solution was cooled down to room temperature and the volatiles were removed under vacuum. The solid was filtered and washed with cold acetone. The product was obtained as a yellow solid. Yield: 1.12 g (2.28 mmol, 65%). ¹H NMR (d₆-DMSO, 300 MHz): δ 9.01 (d, J=5.6 Hz, 2H), 8.80-8.72 (m, 2H), 8.55 (d, J=8.2 Hz, 1H), 8.48 (s, 1H), 8.43 (d, J=7.7 Hz, 1H), 8.29 (t, J=7.1 Hz, 2H), 8.20 (t, J=7.8 Hz, 1H), 8.06 (d, J=8.2 Hz, 1H), 7.86 (t, J=8.6 Hz, 2H), 7.65-7.47 (m, 2H), 7.42 (t, J=7.5 Hz, 1H), 6.60 (s, 2H).

Example 27—Preparation of Precursor 288

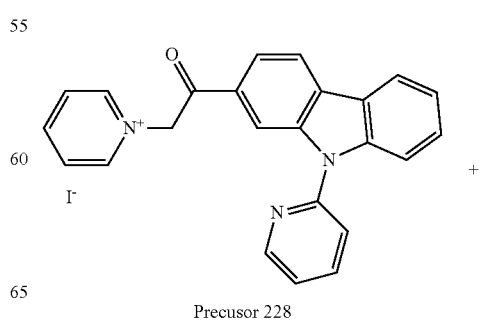

Precursor 228

49

-continued

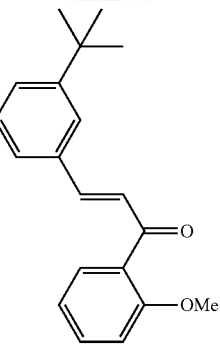

Precusor 218

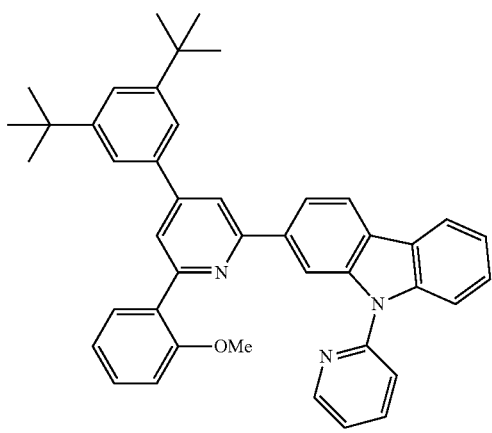

Precusor 288

To a mixture of Precursor 218 (0.80 g, 2.28 mmol) and Precursor 228 (1.12 g, 2.28 mmol) was added 30 g ammonium acetate and 20 mL methanol. The mixture was refluxed overnight. The reaction mixture was partitioned with dichloromethane and water. The organics was dried with magnesium sulfate and evaporated under vacuum. The crude product was purified with column chromatography using dichloromethane as eluent. The product was obtained as a yellow solid. Yield: 0.75 g (1.22 mmol, 53%). $^1$H NMR (CDCl$_3$, 400 MHz): δ8.76-8.75 (m, 1H), 8.63 (s, 1H), 8.23 (d, J=8.2 Hz, 1H), 8.18-8.13 (m, 2H), 8.06-8.02 (m, 2H), 7.95-7.93 (m, 2H), 7.90 (d, J=8.2 Hz, 1H), 7.74 (d, J=8.1 Hz), 7.57-7.56 (m, 3H), 7.47 (t, J=7.7 Hz, 1H), 7.41 (t, J=7.8 Hz, 1H), 7.36-7.32 (m, 2H), 7.14 (t, J=7.1 Hz, 1H), 7.06 (d, J=8.0 Hz, 1H), 3.91 (s, 2H), 1.42 (s, 18H).

50

Example 28—Preparation of Ligand 408

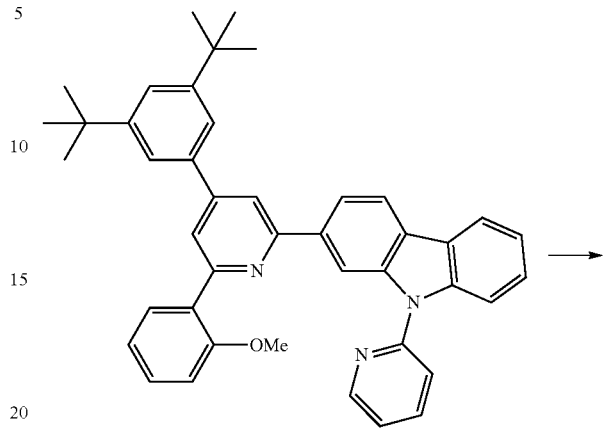

Precusor 288

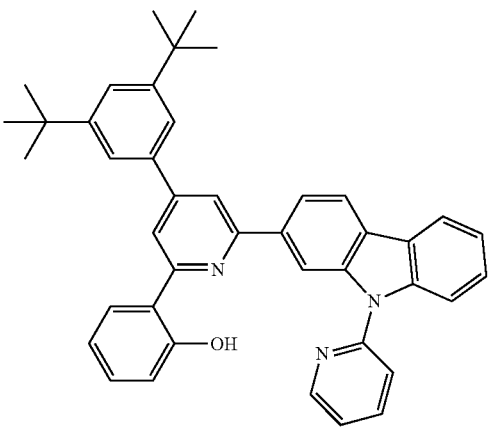

Ligand 408

A mixture of Precursor 288 (0.75 g, 1.22 mmol) and 20 g pyridinum hydrochloride was heated to around 200° C. under nitrogen atmosphere. The reaction progress was monitored by TLC. When all the starting material was consumed, the reaction was quenched with water when hot. The solution was then partitioned with dichloromethane and water. The organic layer was dried with magnesium sulfate and the volatiles were removed under vacuum. The crude product was purified by column chromatography using dichloromethane as eluent. The product was obtained as a yellow solid. Yield: 0.54 g (0.90 mmol, 74%). $^1$H NMR (CDCl$_3$, 500 MHz): δ 14.82 (s, 1H), 8.69 (dd, J=4.9 Hz, 1.3 Hz, 1H), 8.43 (s, 1H), 8.18 (d, J=8.1 Hz, 1H), 8.10 (d, J=7.7 Hz, 1H), 7.95-7.90 (m, 3H), 7.88 (dd, J=8.0 Hz, 1.4 Hz, 1H), 7.84-7.82 (m, 2H), 7.69 (d, J=8.1 Hz, 1H), 7.52 (s, 1H), 7.47 (s, 2H), 7.42 (t, J=7.7 Hz, 1H), 7.30-7.25 (m, 3H), 7.02 (dd, J=8.2 Hz, 1.0 Hz, 1H), 6.89 (t, J=7.5 Hz, 1H), 1.36 (s, 18H).

Example 29—Preparation of Precursor 289

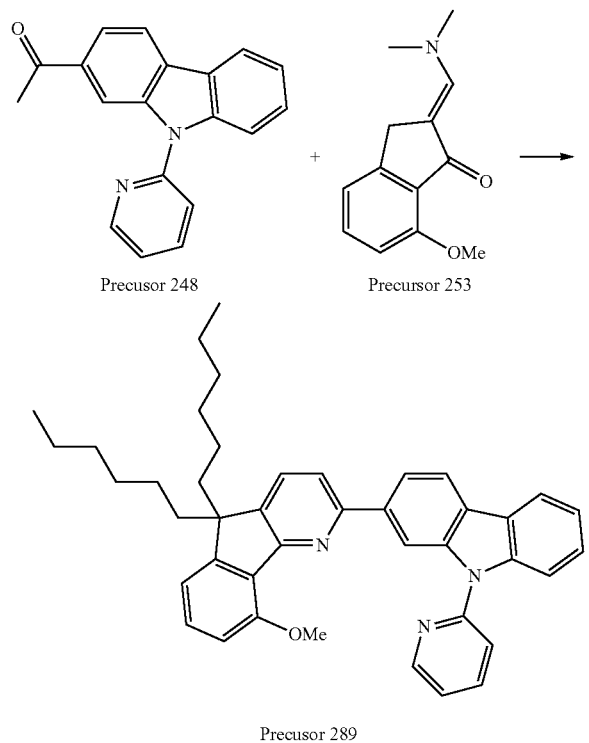

To a degassed 250 mL round-bottom Schlenk flask was added Precursor 248 (1.48 g, 5.16 mmol), potassium tert-butoxide (0.69 g, 6.19 mmol) and 50 mL anhydrous THF. The mixture was stirred at room temperature for 2 hours under nitrogen atmosphere. A solution of Precursor 253 (1.12 g, 5.16 mmol) in 50 mL THF was then added to the above mixture through a cannula. The reaction mixture was stirred overnight at room temperature under nitrogen. To the mixture was then added 50 g ammonium acetate and 25 mL glacial acetic acid. The volatile organics was then removed by distillation at about 100° C. The crude product was then partitioned between dichloromethane and water. The organic layer was dried with magnesium sulfate and the volatiles were removed under vacuum. The crude product of 9-methoxy-2-(9-(pyridin-2-yl)-9H-carbazol-2-yl)-5H-indeno[1,2-b]pyridine was purified by column chromatography using dichloromethane as eluent.

To a degassed round bottom flask with 9-methoxy-2-(9-(pyridin-2-yl)-9H-carbazol-2-yl)-5H-indeno[1,2-b]pyridine (0.45 g, 1.02 mmol), potassium tert-butoxide (0.27 g, 2.45 mmol) dissolved in 50 mL anhydrous THF was added 1-bromohexane (0.50 g, 3.05 mmol). The resulting solution was refluxed for 2 hours and then cooled down to room temperature. The crude product was then partitioned between dichloromethane and water. The organic layer was dried with magnesium sulfate and the volatiles were removed under vacuum. The crude product was purified by column chromatography using dichloromethane as eluent. The product was obtained as yellow oil. Yield: 0.59 g (0.97 mmol, 95%). $^1$H NMR (CDCl$_3$, 400 MHz): δ8.81-8.78 (m, 2H), 8.20 (d, J=8.2 Hz, 1H), 8.14 (d, J=9.5 Hz, 2H), 8.00 (t, J=7.7 Hz, 1H), 7.88 (d, J=8.2 Hz, 1H), 7.83-7.7.78 (m, 2H), 7.65 (d, J=8.0 Hz, 1H), 7.45 (t, J=7.7 Hz, 1H), 7.40-7.31 (m, 3H), 7.00 (d, J=7.4 Hz, 1H), 6.91 (d, J=8.1 Hz, 1H), 4.06 (s, 3H), 2.01-1.94 (m, 4H), 1.11-0.99 (m, 12H), 0.74 (t, J=7.1 Hz, 6H), 0.64-0.60 (m, 4H).

Example 30—Preparation of Ligand 409

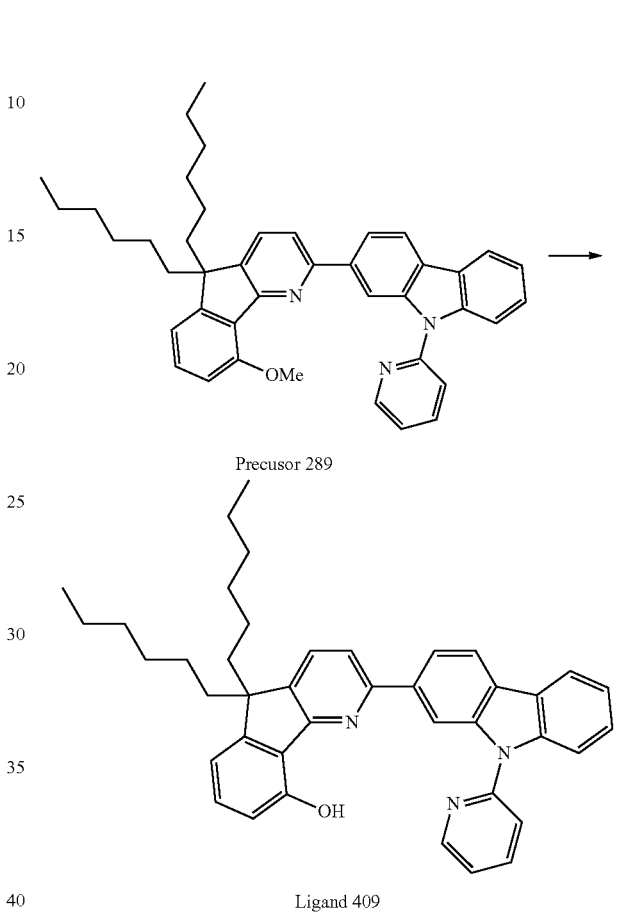

A degassed 100 mL round bottom flask charged with Precursor 289 (0.59 g, 0.97 mmol) and 20 g pyridinum hydrochloride was heated to around 200° C. The reaction was monitored by TLC. When all the starting material was consumed, the reaction was quenched with water when hot. The solution was then partitioned between dichloromethane and water. The organic layer was dried with magnesium sulfate and the volatiles were removed under vacuum. The crude product was purified by column chromatography using dichloromethane as eluent. The product was obtained as yellow oil. Yield: 0.47 g (0.79 mmol, 82%). $^1$H NMR (CDCl$_3$, 500 MHz): δ 9.47 (s, 1H), 8.80 (d, J=4.9 Hz, 1H), 8.60 (s, 1H), 8.21 (d, J=8.1 Hz, 1H), 8.16 (d, J=7.7 Hz, 1H), 8.02-7.98 (m, 2H), 7.88 (d, J=8.3 Hz, 1H), 7.75 (d, J=8.1 Hz, 1H), 7.71-7.67 (m, 2H), 7.48 (t, J=7.7 Hz, 1H), 7.37-7.30 (m, 3H), 6.92-6.89 (m, 2H), 2.02-1.92 (m, 4H), 1.17-1.03 (m, 12H), 0.79-0.71 (m, 10H). $^{13}$C NMR (CDCl$_3$, 126 MHz): δ 161.20, 155.55, 154.47, 152.51, 151.76, 149.81, 141.75, 140.39, 140.11, 138.64, 137.09, 130.96, 130.84, 126.60, 124.95, 124.42, 124.03, 121.49, 121.15, 120.49, 120.40, 119.88, 119.15, 117.90, 114.24, 113.45, 111.30, 109.64, 54.30, 39.72, 31.49, 29.68, 24.04, 22.55, 13.98.

Example 31—Preparation of Complex 101

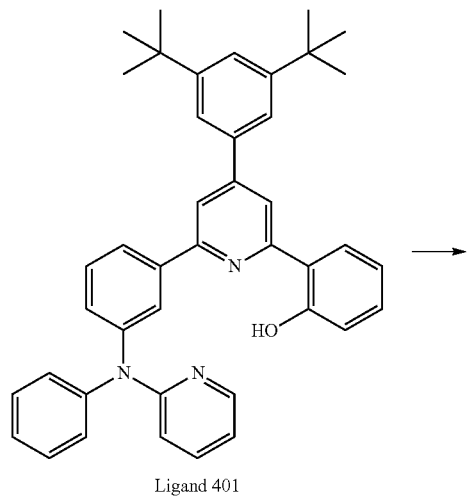

Ligand 401

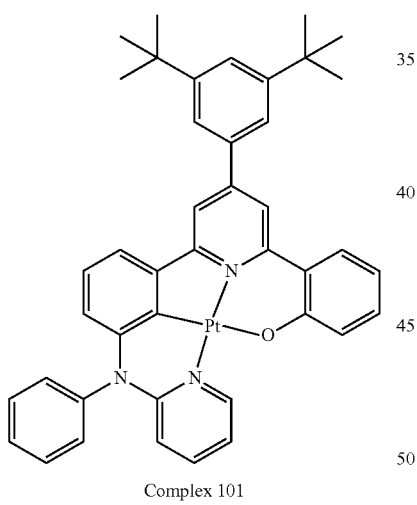

Complex 101

To a round bottom flask was charged with Ligand 401 (0.42 g, 0.69 mmol), K$_2$PtCl$_4$ (0.35 g, 0.83 mmol), and mixture of glacial acetic acid (140 mL) and chloroform (5 mL). The mixture was refluxed under argon for 24 h. After cooling to room temperature, the crude mixture was extracted with dichloromethane and purified by chromatography on alumina with mixture of hexane and ethyl acetate (v/v=10:1). 0.5 g of orange solid was obtained. Yield: 90%. $^1$H NMR (CD$_2$Cl$_2$, 500 MHz): δ 10.18 (d, J=6.3 Hz, 1H), 8.23 (s, 1H), 7.99 (d, J=8.4 Hz, 1H), 7.90 (s, 1H), 7.72-7.69 (m, 2H), 7.64-7.59 (m, 4H), 7.54-7.51 (m, 2H), 7.49-7.34 (m, 3H), 7.25 (d, J=8.4 Hz, 1H), 6.98 (t, J=7.9 Hz, 1H), 6.85 (t, J=6.6 Hz, 1H), 6.72 (t, J=7.5 Hz, 1H), 6.41 (d, J=8.7 Hz, 1H), 6.14 (d, J=8.3 Hz, 1H), 1.43 (s, 18H). MS(FAB): 797.3 (M$^+$)

Example 32—Preparation of Complex 102

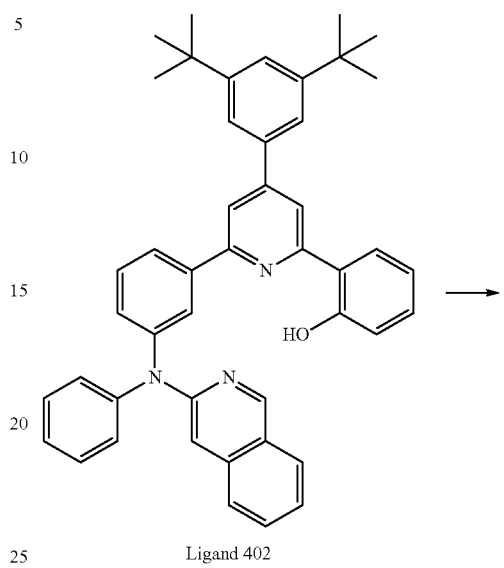

Ligand 402

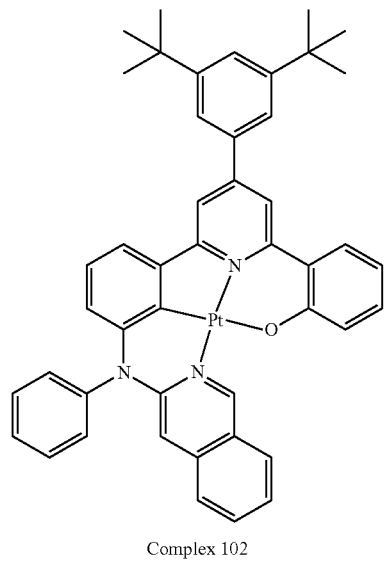

Complex 102

To a round bottom flask were charged with Ligand 402 (0.09 g, 0.13 mmol), K$_2$PtCl$_4$ (0.07 g, 0.16 mmol), and mixture of glacial acetic acid (24 mL) and chloroform (0.9 mL). The mixture was refluxed under nitrogen for 24 h. After cooling to room temperature, the crude mixture was extracted with dichloromethane and purified by chromatography on alumina with mixture of hexane and ethyl acetate (v/v=10:1). 0.10 g of yellow solid was obtained. Yield: 91%. $^1$H NMR (CD$_2$Cl$_2$, 300 MHz): δ 11.05 (s, 1H), 8.16 (s, 1H), 7.98-7.93 (m, 2H), 7.83 (s, 1H), 7.67 (t, J=7.2 Hz, 2H), 7.56-7.54 (m, 4H), 7.50 (t, J=7.4 Hz, 1H), 7.40-7.32 (m, 3H), 7.30-7.25 (m, 4H), 6.90 (t, J=7.9 Hz, 1H), 6.67 (t, J=7.2 Hz, 1H), 6.55 (s, 1H), 6.06 (d, J=8.3 Hz, 1H), 1.36-1.32 (m, 18H). MS(ESI): 847.6 (M$^+$).

Example 33—Preparation of Complex 103

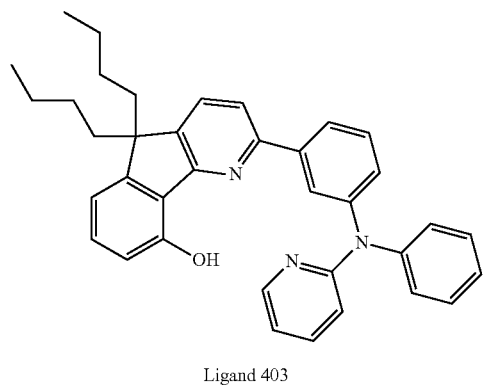

Ligand 403

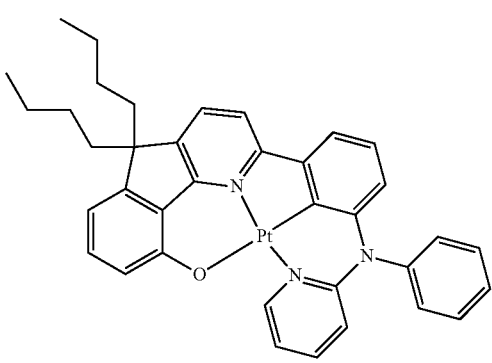

Complex 103

To a round bottom flask was charged with Ligand 403 (0.34 g, 0.63 mmol), K₂PtCl₄ (0.31 g, 0.76 mmol), and mixture of glacial acetic acid (100 mL) and chloroform (5 mL). The mixture was refluxed under argon for 24 h. After cooling to room temperature, the crude mixture was extracted with dichloromethane and purified by chromatography on alumina with mixture of hexane and ethyl acetate (v/v=10:1). 0.42 g of yellow solid was obtained. Yield: 90%. $^1$H NMR (CD$_2$Cl$_2$, 500 MHz): δ 10.28 (d, J=6.1 Hz, 1H), 7.86 (d, J=7.6 Hz, 1H), 7.71 (t, J=7.5 Hz, 2H), 7.61 (t, J=8.7 Hz, 2H), 7.52 (t, J=7.0 Hz, 1H), 7.44-7.47 (m, 2H), 7.38 (d, J=7.2 Hz, 2H), 7.05 (d, J=8.3 Hz, 1H), 6.98 (t, J=8.2 Hz, 1H), 6.86 (t, J=6.8 Hz, 1H), 6.68 (d, J=7.1 Hz, 1H), 6.42 (d, J=8.1 Hz, 1H), 6.12 (d, J=8.3 Hz, 1H), 1.92-1.97 (m, 4H), 1.06-1.10 (m, 4H), 0.66-0.71 (m, 10H).

Example 34—Preparation of Complex 104

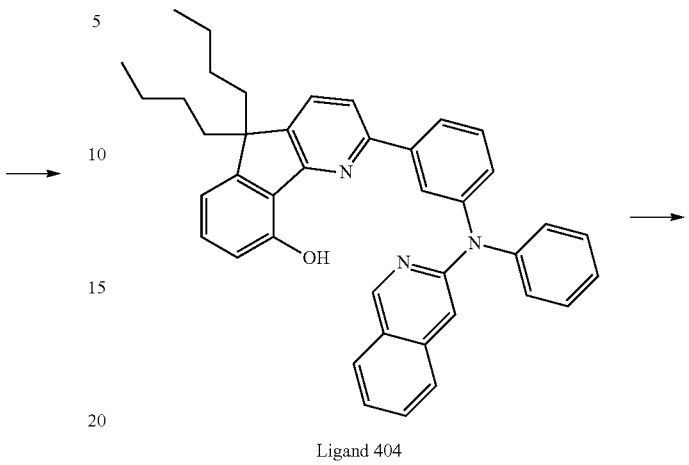

Ligand 404

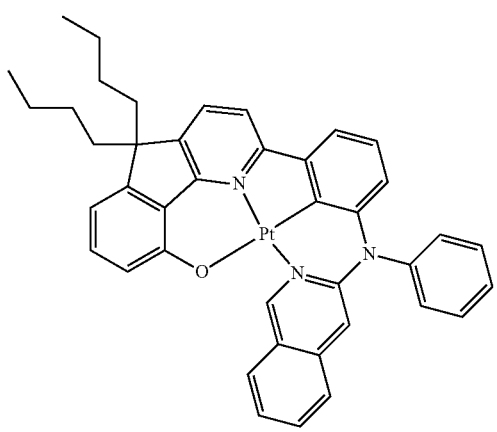

Complex 104

To a round bottom flask were charged with Ligand 404 (0.04 g, 0.06 mmol), K₂PtCl₄ (0.03 g, 0.08 mmol), and mixture of glacial acetic acid (13 mL) and chloroform (0.5 mL). The mixture was refluxed under nitrogen for 24 h. After cooling to room temperature, the crude mixture was extracted with dichloromethane and purified by chromatography on alumina with mixture of hexane and ethyl acetate (v/v=10:1). 0.05 g of yellow solid was obtained. Yield: 95%. $^1$H NMR (CDCl$_3$, 300 MHz): δ 11.16 (s, 1H), 7.98 (d, J=8.2 Hz, 1H), 7.79 (d, J=7.7 Hz, 1H), 7.66 (t, J=7.2 Hz, 2H), 7.58-7.45 (m, 3H), 7.42 (t, J=7.2 Hz, 1H), 7.35 (t, J=8.4 Hz, 3H), 7.27 (q, J=7.2 Hz, 2H), 7.09 (d, J=8.3 Hz, 1H), 6.89 (t, J=7.9 Hz, 1H), 6.63 (d, J=6.9 Hz, 1H), 6.57 (s, 1H), 6.05 (d, J=8.0 Hz, 1H) 2.01-1.95 (m, 4H), 1.12-1.03 (m, 4H), 0.71-0.61 (m, 10H). MS (ESI): 782.5 (M⁺).

Example 35—Preparation of Complex 105

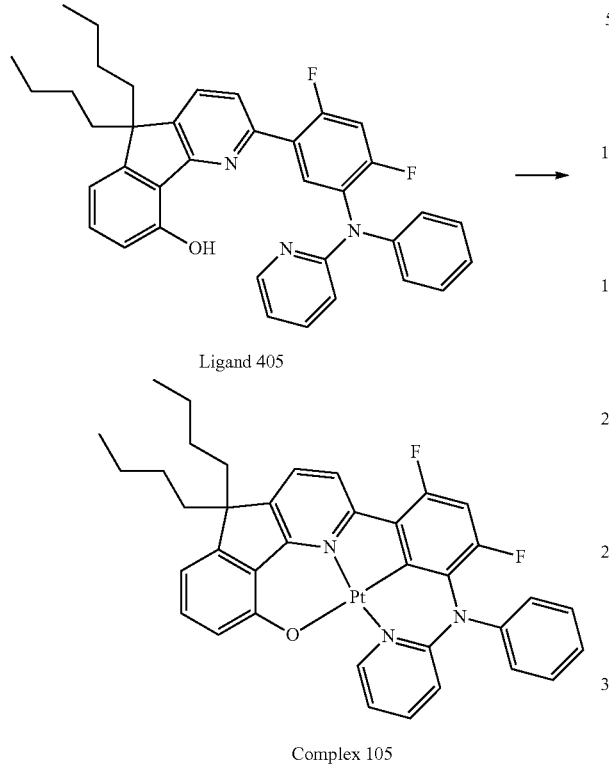

Ligand 405

Complex 105

To a round bottom flask was charged with Ligand 405 (0.09 g, 0.2 mmol), $K_2PtCl_4$ (0.08 g, 0.2 mmol), and mixture of glacial acetic acid (30 mL) and chloroform (1.2 mL). The mixture was refluxed under nitrogen for 24 h. After cooling to room temperature, the crude mixture was extracted with dichloromethane and purified by chromatography on alumina with mixture of hexane and ethyl acetate (v/v=10:1). 0.1 g of yellow solid was obtained. Yield: 90%. $^1$H NMR (CD$_2$Cl$_2$, 400 MHz): δ 9.92 (d, J=6.2 Hz, 1H), 7.87-7.87 (m, 2H), 7.57 (t, J=7.9 Hz, 1H), 7.46-7.25 (m, 7H), 7.03 (d, J=8.2 Hz, 1H), 6.99 (t, J=7.9 Hz, 1H), 6.67 (d, J=7.0 Hz, 1H), 6.55 (t, J=8.5 Hz, 1H), 2.06-1.98 (m, 4H), 1.11-1.04 (m, 4H), 0.71-0.63 (m, 10H). MS(ESI): 769.3 (M$^+$).

Example 36—Preparation of Complex 106

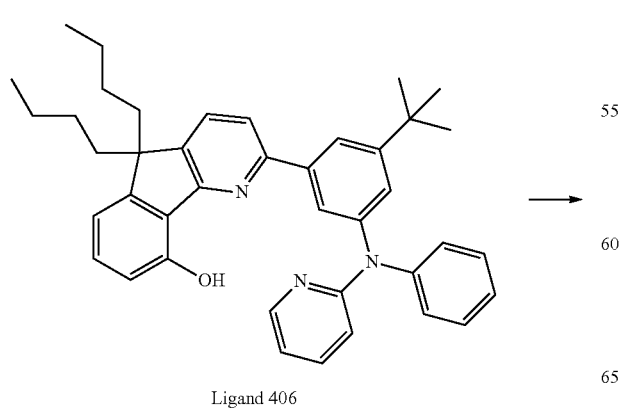

Ligand 406

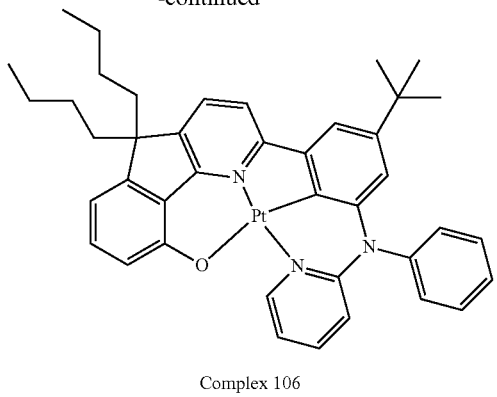

Complex 106

To a round bottom flask were charged with Ligand 406 (0.59 g, 1.0 mmol), $K_2PtCl_4$ (0.50 g, 1.2 mmol), and mixture of glacial acetic acid (180 mL) and chloroform (6.5 mL). The mixture was refluxed under nitrogen for 24 h. After cooling to room temperature, the crude mixture was extracted with dichloromethane and purified by chromatography on alumina with mixture of hexane and ethyl acetate (v/v=10:1). 0.75 g of yellow solid was obtained. Yield: 95%. $^1$H NMR (CD$_2$Cl$_2$, 500 MHz): δ 10.25 (d, J=5.8 Hz, 1H), 7.85 (d, J=7.7 Hz, 1H), 7.72 (t, J=6.9 Hz, 2H), 7.63-7.60 (m, 2H), 7.52 (t, J=7.9 Hz, 1H), 7.49 (s, 1H), 7.45 (t, J=7.7 Hz, 1H), 7.39 (d, J=7.2 Hz, 1H), 7.04 (d, J=8.1 Hz, 1H), 6.84 (t, J=6.5 Hz, 1H), 6.67 (d, J=6.9 Hz, 1H), 6.46 (d, J=8.9 Hz, 1H), 6.17 (s, 1H), 2.10-1.98 (m, 4H), 1.14-1.09 (m, 13H), 0.80-0.68 (m, 10H). MS(ESI): 788.9 (M$^+$).

Example 37—Preparation of Complex 107

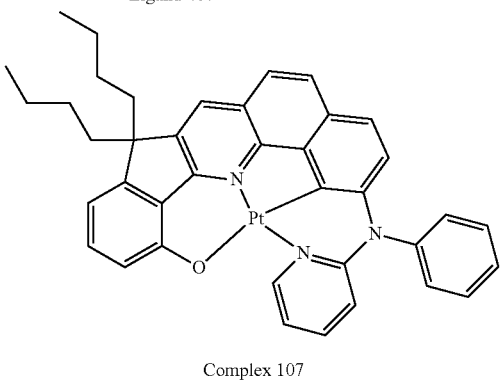

Ligand 407

Complex 107

To a round bottom flask were charged with Ligand 407 (0.25 g, 0.4 mmol), K$_2$PtCl$_4$ (0.22 g, 0.5 mmol), and mixture of glacial acetic acid (80 mL) and chloroform (3 mL). The mixture was refluxed under nitrogen for 24 h. After cooling to room temperature, the crude mixture was extracted with dichloromethane and purified by chromatography on alumina with mixture of hexane and ethyl acetate (v/v=10:1). 0.32 g of yellow solid was obtained. Yield: 96%. $^1$H NMR (CD$_2$Cl$_2$, 500 MHz): δ10.32 (d, J=6.0 Hz, 1H), 8.26 (s, 1H), 7.77-7.72 (m, 4H), 7.66 (t, J=7.6 Hz, 1H), 7.64-7.51 (m, 3H), 7.45 (d, J=8.1 Hz, 2H), 7.16 (d, J=8.4 Hz, 1H), 6.88 (t, J=6.9 Hz, 1H), 6.76 (d, J=7.1 Hz, 1H), 6.56-6.51 (m, 2H), 2.23-2.09 (m, 4H), 1.18-1.11 (m, 4H), 0.89-0.66 (m, 10H). MS(ESI): 756.8 (M$^+$).

Example 38—Preparation of Complex 108

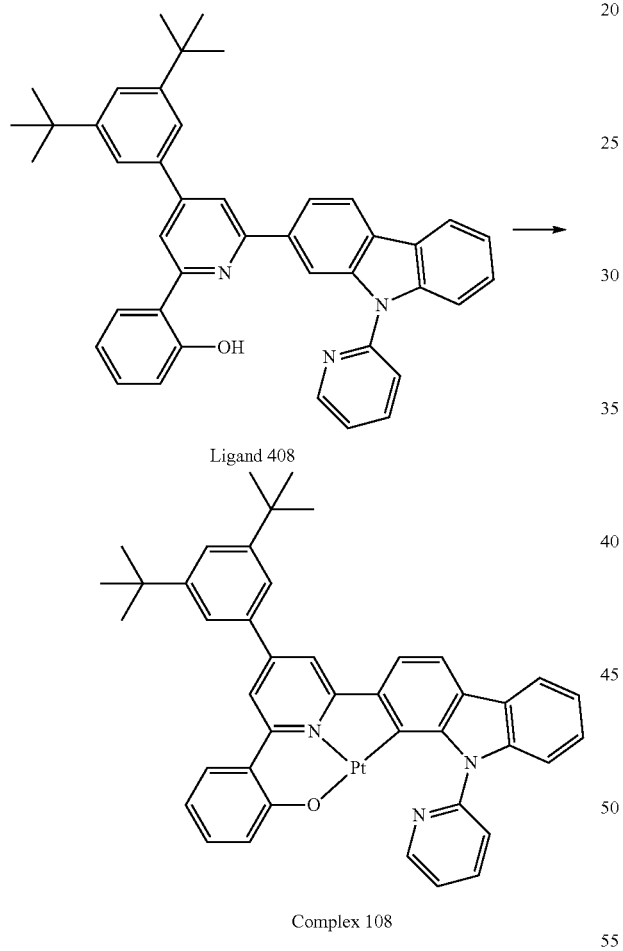

Ligand 408

Complex 108

A mixture of Ligand 408 (0.54 g, 0.90 mmol), potassium tetrachloroplatinate (0.45 g, 1.08 mmol) in 50 mL glacial acetic acid and 10 mL chloroform was refluxed for 2 days. The solution was cooled down to room temperature and was partitioned between dichloromethane and water. The organic layer was dried with magnesium sulfate and the volatiles were removed under vacuum. The crude product was purified by column chromatography using dichloromethane as eluent. The product was obtained as an orange solid. Yield: 0.44 g (62%). $^1$H NMR (CDCl$_3$, 500 MHz): δ9.97 (dd, J=6.0 Hz, 1.3 Hz, 1H), 8.07 (s, 1H), 7.97-7.94 (m, 2H), 7.90 (d, J=8.4 Hz, 1H), 7.87 (d, J=7.4 Hz, 1H), 7.76 (t, J=7.8 Hz, 1H), 7.64 (s, 1H), 7.59 (s, 2H), 7.51 (s, 1H), 7.45 (d, J=8.0 Hz, 1H), 7.39 (t, J=7.4 Hz, 1H), 7.36-7.31 (m, 2H), 7.26 (t, J=7.4 Hz, 1H), 7.20 (dd, J=8.3 Hz, 1.1 Hz, 1H), 6.83 (t, J=6.2 Hz, 1H), 6.74 (t, J=7.4 Hz, 1H), 1.49 (s, 18H). $^{13}$C NMR (CDCl$_3$, 126 MHz): δ 164.76, 164.27, 153.13, 151.87, 150.21, 149.45, 149.39, 147.04, 142.74, 139.64, 138.29, 137.41, 136.85, 131.07, 130.09, 128.50, 126.17, 124.64, 124.23, 123.56, 122.78, 122.09, 121.47, 121.45, 118.75, 118.24, 117.58, 115.14, 114.55, 114.15, 113.62, 113.47, 35.18, 31.63

Example 39—Preparation of Complex 109

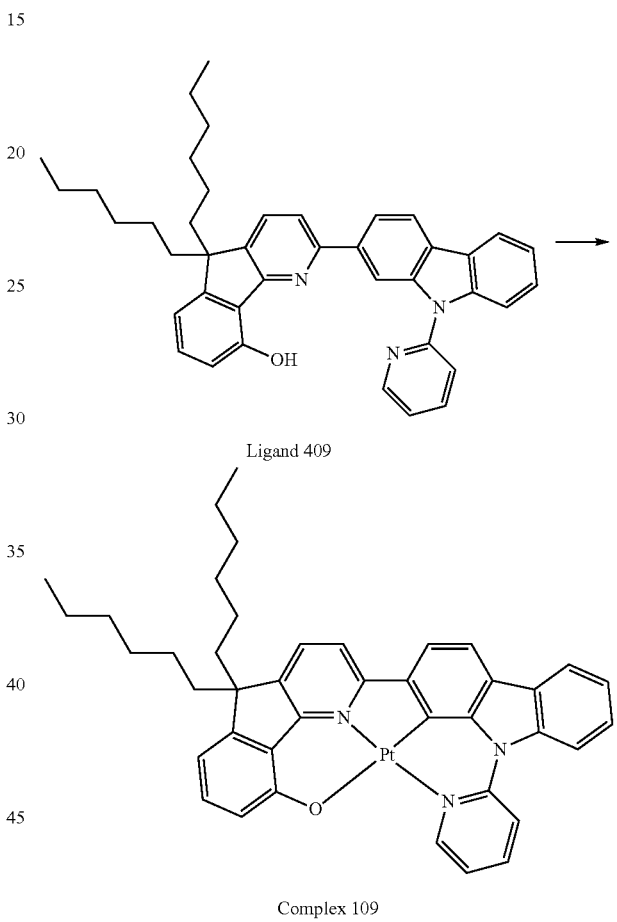

Ligand 409

Complex 109

A mixture of Ligand 409 (0.47 g, 0.79 mmol), potassium tetrachloroplatinate (0.39 g, 0.95 mmol) in 50 mL glacial acetic acid and 10 mL chloroform was refluxed for 2 days. The solution was cooled down to room temperature and was partitioned between dichloromethane and water. The organic layer was dried with magnesium sulfate and the volatiles were removed under vacuum. The crude product was purified by column chromatography using dichloromethane as eluent. The product was obtained as an orange solid. Yield: 0.32 g (51%). $^1$H NMR (CD$_2$Cl$_2$, 500 MHz): δ 10.31 (d, J=6.0 Hz, 1H), 8.18 (d, J=8.6 Hz, 1H), 8.08 (d, J=7.5 Hz, 1H), 8.03 (d, J=8.3 Hz, 1H), 8.01-8.97 (m, 1H), 7.84 (d, J=7.6 Hz, 1H), 7.70 (d, J=7.9 Hz, 1H), 7.61 (d, J=8.0 Hz, 1H), 7.53 (d, J=7.6 Hz, 1H), 7.50-7.46 (m, 2H), 7.39 (t, J=7.4 Hz, 1H), 7.18-7.15 (m, 1H), 7.08 (d, J=8.3 Hz, 1H), 6.71 (d, J=6.7 Hz, 1H), 2.11-1.99 (m, 4H), 1.16-1.05 (m, 12H), 0.83-0.75 (m, 10H). $^{13}$C NMR (CD$_2$Cl$_2$, 126 MHz):

δ 161.73, 160.24, 154.76, 153.50, 150.23, 147.53, 142.79, 142.19, 139.79, 138.15, 137.63, 132.43, 129.54, 128.37, 126.47, 126.04, 123.09, 122.79, 121.53, 121.10, 118.78, 118.36, 118.13, 115.80, 114.18, 114.12, 113.11, 108.18, 55.38, 39.91, 31.50, 29.68, 24.03, 22.53, 13.71.

Example 40—Preparation of Complex 110

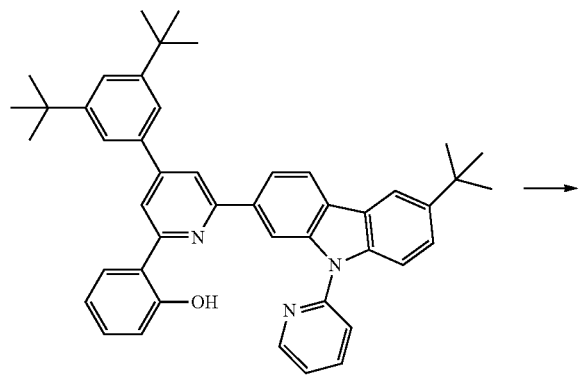

Ligand 410

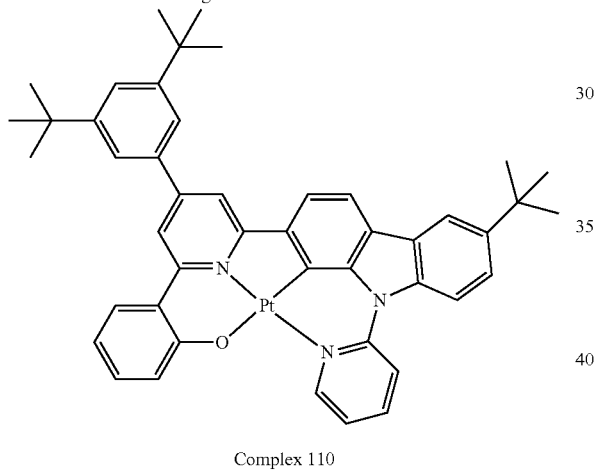

Complex 110

A mixture of Ligand 410 (0.12 g, 0.18 mmol), potassium tetrachloroplatinate (0.08 g, 0.20 mmol) in 50 mL glacial acetic acid and 10 mL chloroform was refluxed for 2 days. The solution was cooled down to room temperature and was partitioned between dichloromethane and water. The organic layer was dried with magnesium sulfate and the volatiles were removed under vacuum. The crude product was purified by column chromatography using dichloromethane as eluent. The product was obtained as an orange-red solid. Yield: 0.11 g (72%). $^1$H NMR (CD$_2$Cl$_2$, 500 MHz): δ 10.06 (dd, J=6.1 Hz, 1.5 Hz, 1H), 8.11 (s, 1H), 8.05 (d, J=8.7 Hz, 1H), 8.00-7.97 (m, 2H), 7.91-7.88 (m, 2H), 7.67 (s, 1H), 7.65 (s, 3H), 7.61 (d, J=8.0 Hz, 1H), 7.53-7.50 (m, 2H), 7.33 (t, J=7.5 Hz, 1H), 7.19 (d, J=8.4 Hz, 1H), 6.97 (t, J=6.6 Hz, 1H), 6.72 (t, J=7.5 Hz, 1H), 1.47 (s, 18H), 1.43 (s, 9H). $^{13}$C NMR (CD$_2$Cl$_2$, 126 MHz): δ 165.49, 164.82, 153.62, 152.55, 150.96, 149.74, 147.84, 146.84, 143.06, 138.76, 138.41, 138.29, 137.62,* 131.68, 130.70, 128.69, 125.04, 124.92, 124.84, 124.31, 123.77, 122.42, 122.05, 119.42, 118.76, 118.47, 118.14, 115.81, 115.07, 114.38, 114.14, 114.09, 35.63. 35.19. 31.99. 31.89.

Example 41—Preparation of Complex 129

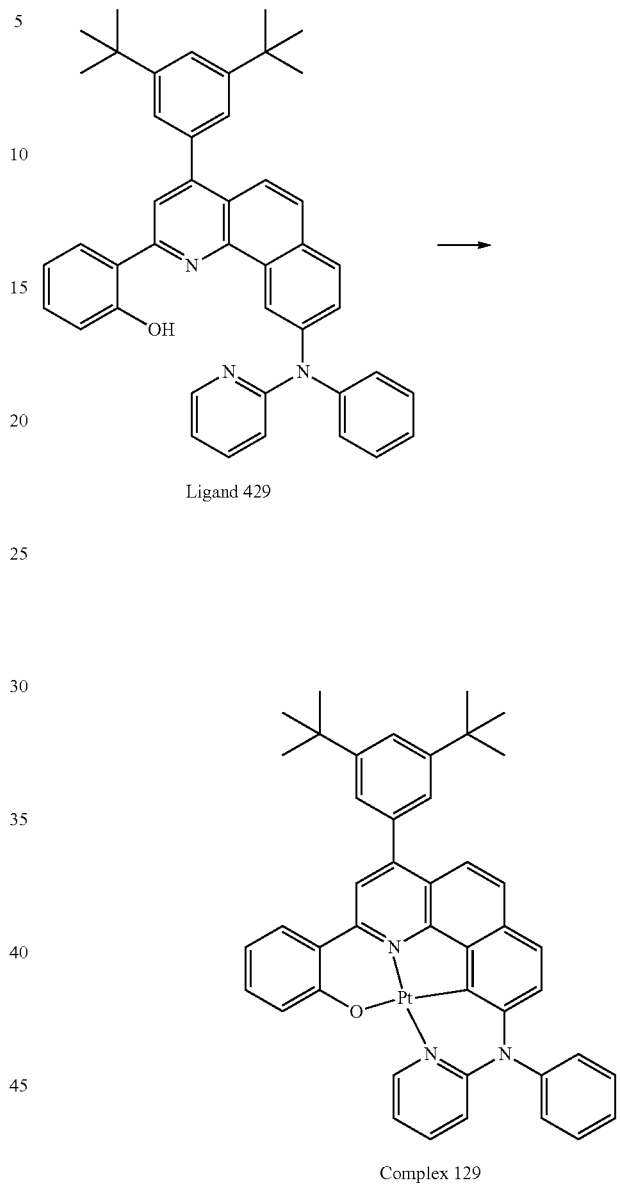

Ligand 429

Complex 129

A mixture of Ligand ONCN09 (0.038 g, 0.06 mmol), potassium tetrachloroplatinate (0.03 g, 0.07 mmol) in 10.4 mL glacial acetic acid and 0.4 mL chloroform was refluxed for 12 hours. The solution was cooled down to room temperature and was partitioned between dichloromethane and water. The organic layer was dried with magnesium sulfate and the volatiles were removed under vacuum. The crude product was purified by column chromatography using hexane and ethyl acetate (v/v=10:1) as eluent. The product was obtained as an orange solid. Yield: 0.046 g (94%). $^1$H NMR (600 MHz, CD$_2$Cl$_2$) δ 10.36 (d, J=6.2 Hz, 1H), 8.47 (s, 1H), 8.30 (d, J=8.4 Hz, 1H), 7.77 (d, J=7.9 Hz, 2H), 7.73 (d, J=11.9 Hz, 1H), 7.66 (s, 2H), 7.59 (d, J=8.8 Hz, 1H), 7.54 (t, J=5.3 Hz, 3H), 7.47 (d, J=7.3 Hz, 2H), 7.42 (s, 2H), 6.92 (t, J=6.5 Hz, 1H), 6.79 (d, J=8.2 Hz, 1H), 6.59 (d, J=8.8 Hz, 1H), 6.56 (d, J=8.9 Hz, 1H), 1.44 (s, 18H).

Example 42—Preparation of Complex 130

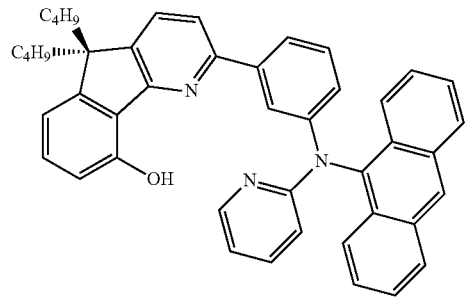

Ligand 430

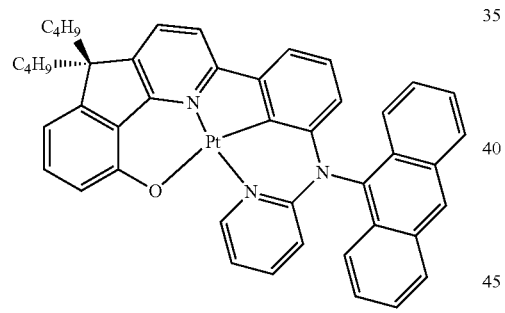

Complex 130

A mixture of Ligand ONCN12 (0.044 g, 0.07 mmol), potassium tetrachloroplatinate (0.03 g, 0.08 mmol) in 12.5 mL glacial acetic acid and 0.4 mL chloroform was refluxed for 12 hours. The solution was cooled down to room temperature and was partitioned between dichloromethane and water. The organic layer was dried with magnesium sulfate and the volatiles were removed under vacuum. The crude product was purified by column chromatography using hexane and ethyl acetate (v/v=10:1) as eluent. The product was obtained as an orange solid. Yield: 0.054 g (95%). $^1$H NMR (600 MHz, CD$_2$Cl$_2$) δ 10.40 (d, J=4.9 Hz, 1H), 8.76 (s, 1H), 8.21 (d, J=8.6 Hz, 2H), 7.88 (d, J=7.6 Hz, 1H), 7.84 (d, J=8.6 Hz, 2H), 7.62 (d, J=7.6 Hz, 1H), 7.54 (d, J=7.8 Hz, 2H), 7.49 (s, 1H), 7.47-7.39 (m, 3H), 7.35-7.27 (m, 1H), 7.10 (d, J=8.2 Hz, 1H), 6.87 (t, J=6.6 Hz, 1H), 6.72 (d, J=7.1 Hz, 2H), 6.02 (d, J=8.9 Hz, 1H), 5.71 (d, J=8.2 Hz, 1H), 2.07 (m, 4H), 1.15 (m, 5H), 0.72 (m, 10H).

Example 43—Preparation of Complex 13

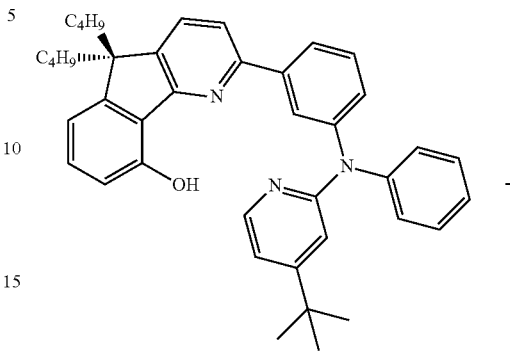

Ligand 431

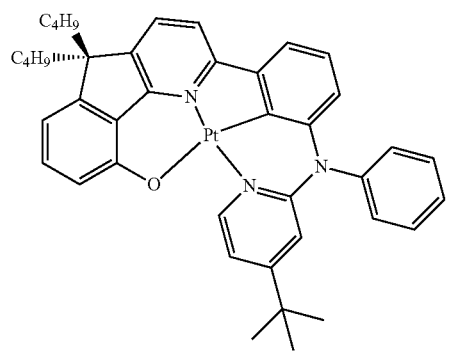

Complex 131

A mixture of Ligand ONCN14 (0.086 g, 0.14 mmol), potassium tetrachloroplatinate (0.03 g, 0.16 mmol) in 25.5 mL glacial acetic acid and 1 mL chloroform was refluxed for 12 hours. The solution was cooled down to room temperature and was partitioned between dichloromethane and water. The organic layer was dried with magnesium sulfate and the volatiles were removed under vacuum. The crude product was purified by column chromatography using hexane and ethyl acetate (v/v=10:1) as eluent. The product was obtained as an orange solid. Yield: 0.107 g (93%). $^1$H NMR (600 MHz, CD$_2$Cl$_2$) δ 10.10 (d, J=6.6 Hz, 1H), 7.86 (d, J=7.6 Hz, 1H), 7.72 (t, J=7.8 Hz, 2H), 7.65-7.54 (m, 2H), 7.46 (t, J=7.6 Hz, 2H), 7.41-7.35 (m, 2H), 7.04 (d, J=8.2 Hz, 1H), 7.01-6.95 (m, 1H), 6.90 (d, J=6.7 Hz, 1H), 6.68 (d, J=7.1 Hz, 1H), 6.35 (s, 1H), 6.15 (d, J=8.2 Hz, 1H), 2.04 (m, 4H), 1.27 (m, 3H), 1.19-1.04 (m, 10H), 0.82-0.63 (m, 9H).

Example 44—Photophysical Properties for
Complexes 101, 102, 103, 105, 106, 107, 108, 109
and 129

|  | Absorption $\lambda_{max}$/nm (molar extinction coefficient/$10^4$ mol$^{-1}$dm$^3$ cm$^{-1}$) | Emission (dichloromethane solution) | | | |
| --- | --- | --- | --- | --- | --- |
|  |  | $\lambda_{max}$/nm | φ | τ/μs | $K_q$/mol$^{-1}$dm$^3$s$^{-1}$ |
| Complex 101 | 330 (2.16), 370 (1.13), 450 (0.27), 481 (0.21) | 551 | 0.91 | 4.31 | $2 \times 10^7$ |
| Complex 102 | 342 (1.96), 370 (0.99), 432 (0.21), 492 (0.14) | 540, 605, 659 | 0.092 | 12.5 | $2 \times 10^7$ |
| Complex 103 | 321 (1.87), 337 (1.31), 365 (1.17), 393 (0.79), 434 (0.44), 458 (0.38) | 511, 540 | 0.92 | 13.0 | $2 \times 10^8$ |
| Complex 105 | 336 (0.85), 355 (0.97), 386 (0.56), 416 (0.42), 438 (0.34), 469 (0.04) | 505, 530, 574 | 0.54 | 31.6 | $2 \times 10^6$ |
| Complex 106 | 325 (2.30), 368 (1.44), 396 (1.03), 438 (0.54), 464 (0.46) | 515, 552, 596 | 0.97 | 10.9 | $4 \times 10^7$ |
| Complex 107 | 334 (1.99), 355 (1.40), 375 (1.02), 433 (0.98), 474 (0.36) | 531, 573 | 0.44 | 26.5 | $7 \times 10^6$ |
| Complex 108 | 264 (43213); 274 (45223); 324 (26577); 353 (18914); 369 (16897); 414 (13880); 442 (5902); 471 (4463) | 540, 583, 625 | 0.41 |  |  |
| Complex 109 | 278 (5218); 298 (47859); 334 (40668); 355 (23675); 385 (15888); 413 (9370); 461 (4078); 488 (3516); | 553, 587 | 0.86 |  |  |
| Complex 129 | 343 (2.09), 364 (1.51), 439 (0.66), 472 (0.37), 501 (0.31) | 573 | 0.21 | 12.6 | $5 \times 10^7$ |

Example 45—General Procedures for Vacuum Deposition

In one embodiment, OLEDs were fabricated on glass substrates with pre-patterned ITO electrodes. The substrates were cleaned in an ultrasonic bath of detergent and deionized water, rinsed with deionized water, and then cleaned in sequential ultrasonic baths of dionized water, acetone, and isopropanol, and subsequently dried in an oven for 1 h. The substrates were then transferred into a vacuum chamber, in which functional layers were in sequence deposited by thermal evaporation at a pressure of $10^{-6}$-$10^{-7}$ torr. The thickness of the deposited material was monitored in situ using an oscillating quartz thickness monitor. Finally a LiF buffer layer and Al cathode were vapor deposited onto the organic films. EL spectra, luminance, and CIE coordination were measured by a Photo Research Inc PR-655. Voltage-current characteristics were measured by using a Keithley 2400 source measurement unit. All devices were characterized at room temperature in the atmosphere without encapsulation.

Example 46—OLED 1

A device was fabricated according to Example 45 wherein four functional layers including MoO$_3$ (5 nm), CzSiCz (40 nm), CsPO$_3$: Complex 101 (4%, 30 nm) and DPOSi (30 nm), which were used as hole-injection layer, hole-transporting layer, emissive layer and electron-transporting layer respectively, were deposited in sequence. This device showed yellow emission with CIE coordinate of (0.42, 0.56), maximum current efficiency of 62.4 cd/A and efficiency roll-off of 11.9% at 1000 cd/m$^{-2}$.

Example 47—OLED 2

A device was fabricated according to Example 45 wherein four functional layers including MoO$_3$ (2 nm), DczSi (40 nm), CsPO1: Complex 101 (2%, 30 nm) and DPOSi (30 nm), which were used as hole-injection layer, hole-transporting layer, emissive layer and electron-transporting layer respectively, were deposited in sequence. This device showed yellow emission with CIE coordinate of (0.39, 0.59), maximum current efficiency of 77.0 cd/A and efficiency roll-off of 5.2% at 1000 cd/m$^{-2}$.

Example 48—OLED 3

A device was fabricated with according to 45 wherein four functional layers including MoO$_3$ (5 nm), CzSiCz (40 nm), CsPO3: Complex 103 (2%, 30 nm) and DPOSi (30 nm), which were used as hole-injection layer, hole-transporting layer, emissive layer and electron-transporting layer respectively, were deposited in sequence. This device showed green emission with CIE coordinate of (0.28, 0.61), maximum current efficiency of 43.6 cd/A and efficiency roll-off of 12.8% at 1000 cd/m$^{-2}$.

Example 49—OLED 4

A device was fabricated according to Example 45 wherein six functional layers including MoO$_3$ (5 nm), NPB (30 nm), TCTA (10 nm), TCTA: Complex 103 (10%, 15 nm), 1,3,5-tri(phenyl-2-benzimidazolyl)-benzene (TPBi): Complex 103 (10%, 15 nm) and TPBi (30 nm) which were used as hole-injection layer, hole-transporting layer, electron-blocking layer, emissive layer 1, emissive layer 2 and electron-transporting layer respectively, were deposited in sequence. This device showed green emission with CIE coordinate of (0.27, 0.60), maximum current efficiency of 60.0 cd/A and efficiency roll-off of 33.3% at 1000 cd/m$^{-2}$.

Example 50—OLED 5

A device was fabricated according to Example 45 wherein six functional layers including MoO$_3$ (5 nm), NPB (30 nm), TCTA (10 nm), CBP: Complex 103 (7%, 15 nm), TAZ: Complex 103 (7%, 15 nm) and TAZ (30 nm) which were used as hole-injection layer, hole-transporting layer, electron-blocking layer, emissive layer 1, emissive layer 2 and electron-transporting layer respectively, were deposited in sequence. This device showed green emission with CIE coordinate of (0.27, 0.60), maximum current efficiency of 78.0 cd/A and efficiency roll-off of 38.5% at 1000 cd/m$^{-2}$.

Example 51—General Procedures for Solution Process Fabrication

In one embodiment, OLEDs were fabricated on glass substrates with pre-patterned indium tin oxide (ITO) electrodes. The substrates were cleaned in an ultrasonic bath of detergent and deionized water, rinsed with deionized water, and then cleaned in sequential ultrasonic baths of dionized water, acetone, and isopropanol, and subsequently dried in an oven for 1 h. The solution processable functional layers were deposition in sequence by spin coating. The samples were then transferred into a vacuum chamber, in which the rest functional layers were in sequence deposited by thermal evaporation at a pressure of 10$^{-6}$-10$^{-7}$ torr. The thickness of the deposited material was monitored in situ using an oscillating quartz thickness monitor. Finally a LiF buffer layer and Al cathode were vapor deposited onto the organic films. EL spectra, luminance, and CIE coordination were measured by a Photo Research Inc PR-655. Voltage-current characteristics were measured by using a Keithley 2400 source measurement unit. All devices were characterized at room temperature in the atmosphere without encapsulation.

Example 52—OLED 6

A device was fabricated according to Example 51 wherein two solution processable functional layers including PEDOT: PPS and POSC1: Complex 101 (10%), which were used as hole-injection and hole-transporting layer and emissive layer respectively, were deposited by spin coated in sequenced. Afterward, a layer of TPBi (30 nm) was deposition by vacuum deposition as electron-transporting layer. This device showed yellow emission with CIE coordinate of (0.46, 0.54), maximum current efficiency of 35.0 cd/A and efficiency roll-off of 5.7% at 1000 cd/m$^{-2}$.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

What is claimed is:

1. A compound having a chemical structure of Structure II:

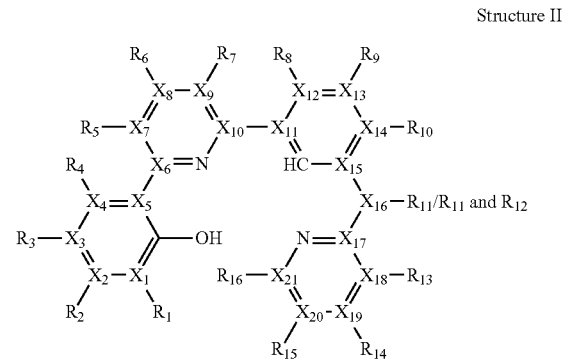

Structure II wherein $R_1$-$R_{16}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;

wherein each pair of adjacent R groups of $R_1$-$R_{16}$ can be independently two separate groups or one group, and form one or more 5-8 member rings with 2 to 4 X groups; and wherein $X_1$-$X_{21}$ are independently carbon, nitrogen, silicon, germanium, or phosphorous.

2. The compound of claim 1, wherein $R_{11}$ is aryl or substituted aryl group, and $R_{10}$ can be one of the carbon atoms on $R_{11}$ thereby forming a 6-5-6 fused ring system with the adjacent aryl ring.

3. The compound of claim 1, wherein the compound is selected from a group consisting of Ligand 401 to Ligand 431:

Ligand 401
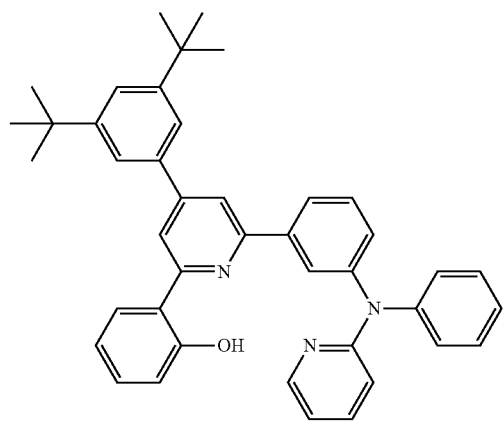
Ligand 402
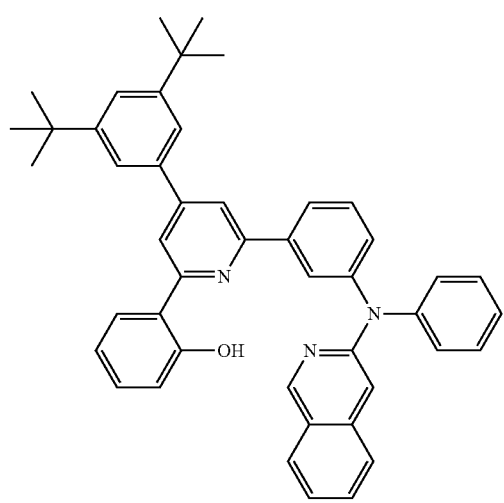
Ligand 403
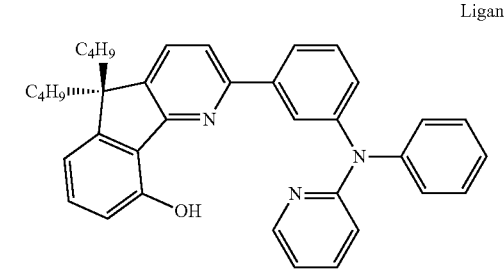
Ligand 404
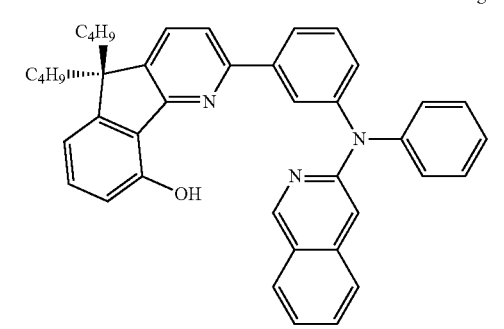
Ligand 405
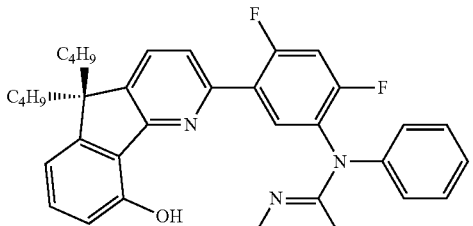
Ligand 406
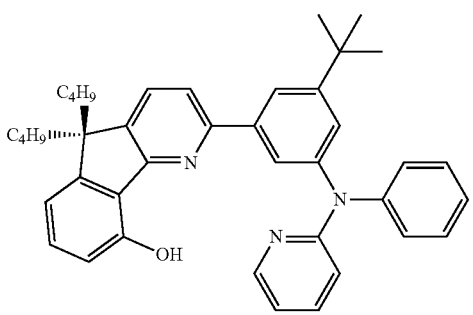
Ligand 407
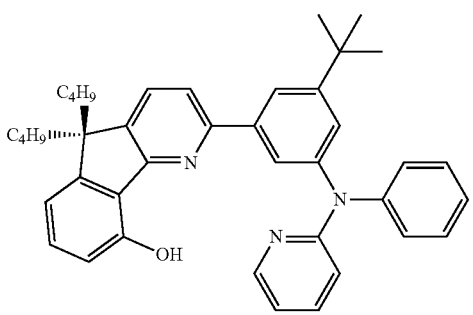
Ligand 408
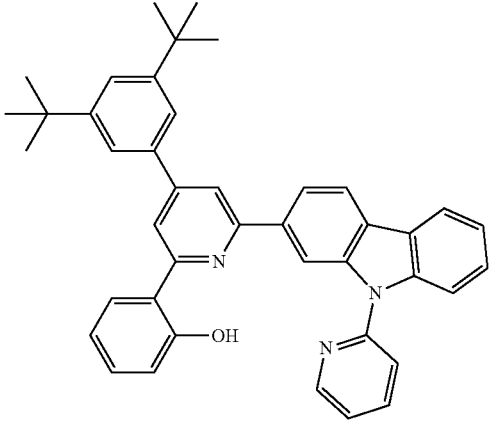
Ligand 409
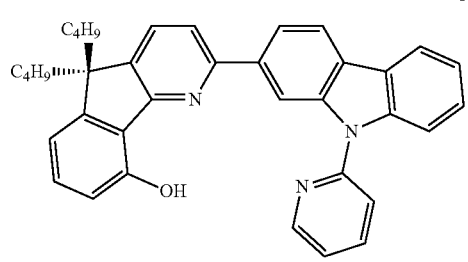

Ligand 410
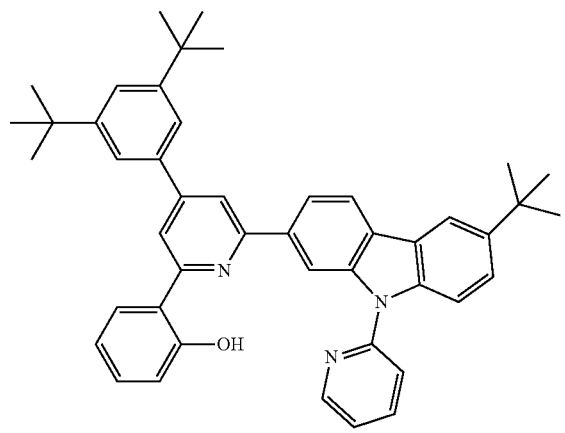
Ligand 411
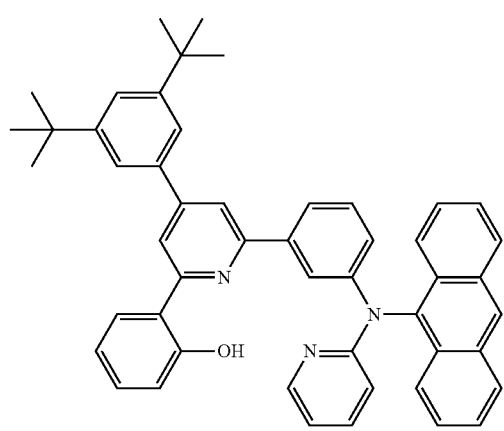
Ligand 412
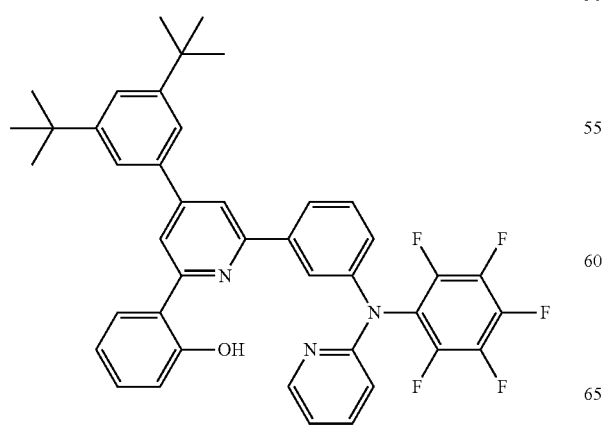
Ligand 413
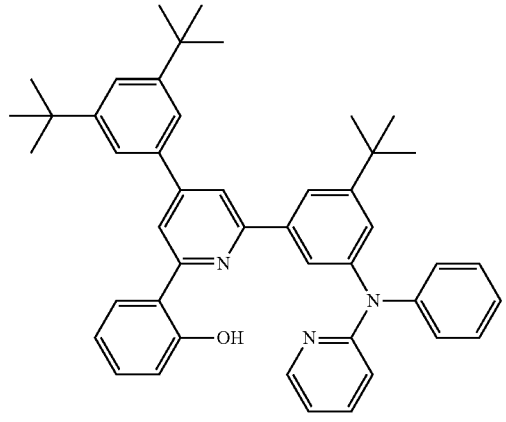
Ligand 414
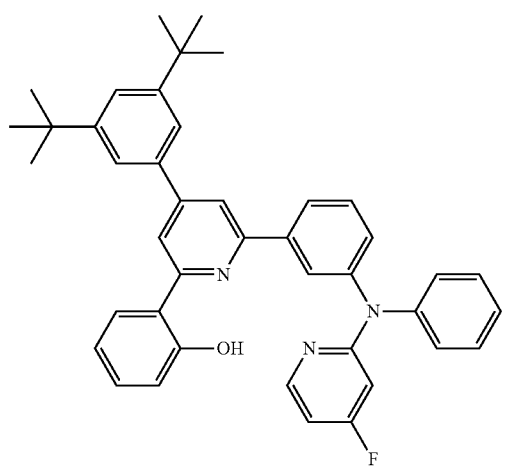
Ligand 415
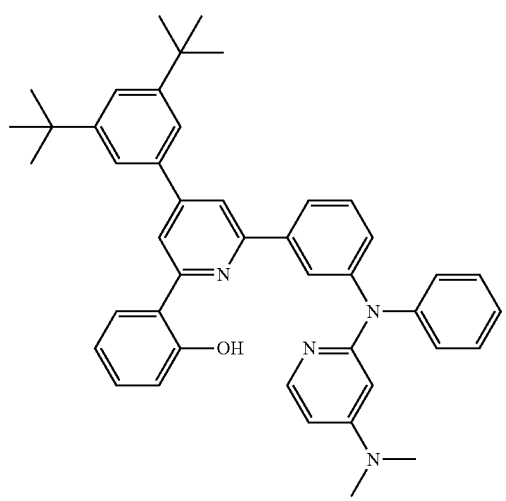

Ligand 416
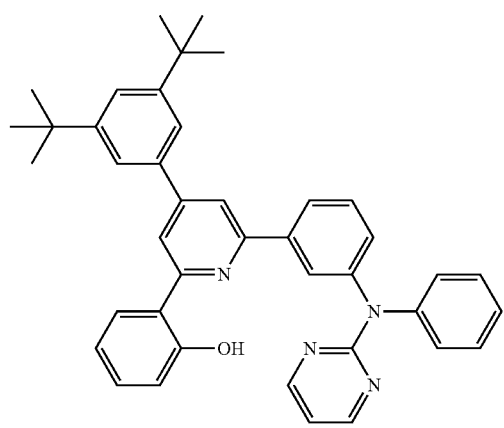
Ligand 417
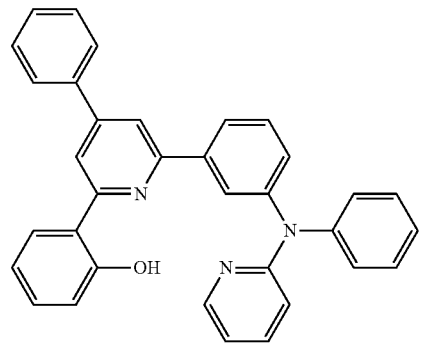
Ligand 418
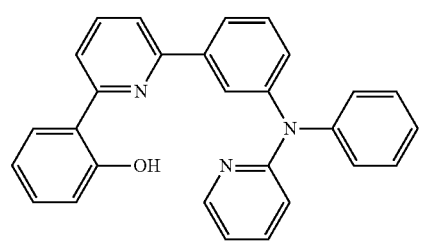
Ligand 419
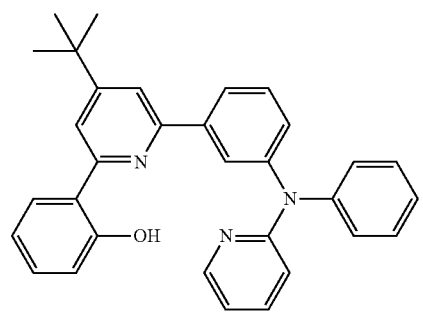
Ligand 420
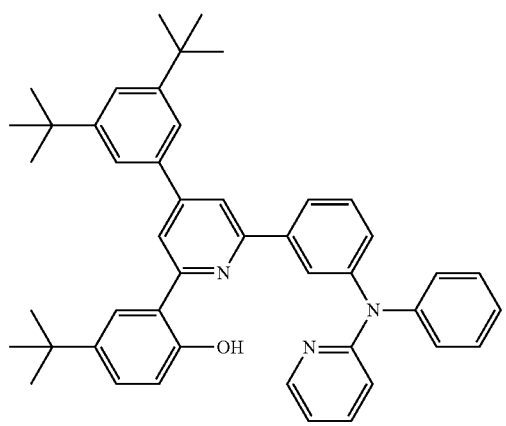
Ligand 421
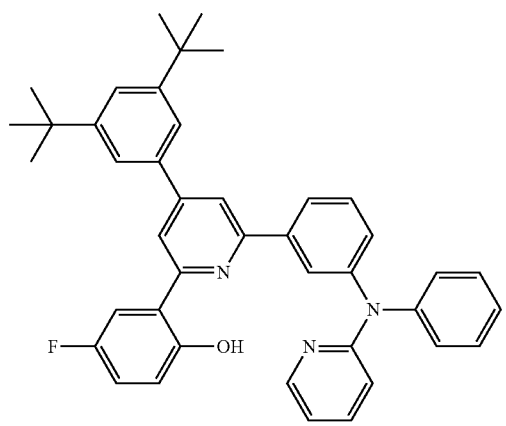
Ligand 422
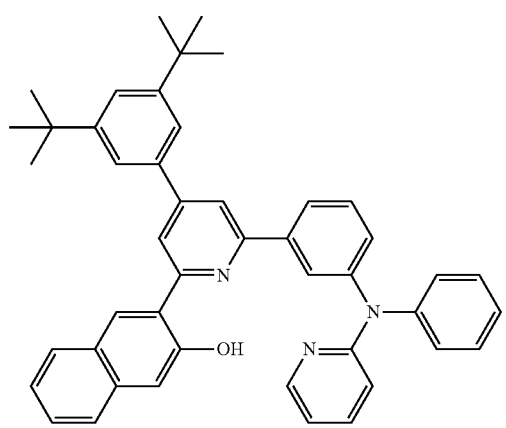

Ligand 423
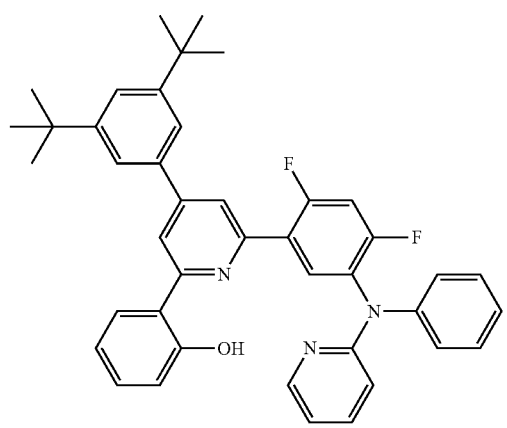
Ligand 426
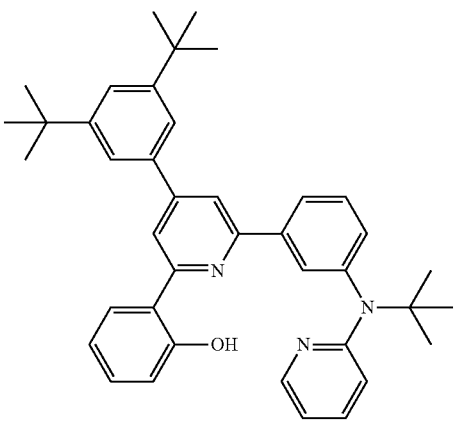
Ligand 424
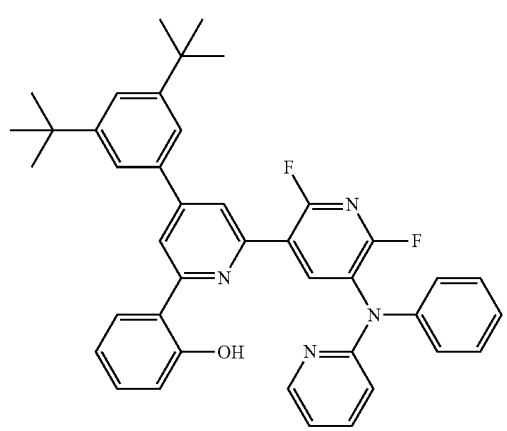
Ligand 427
Ligand 425
Ligand 428
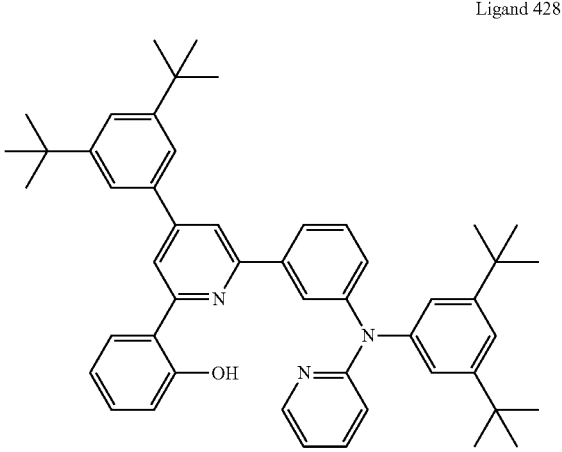

Ligand 429

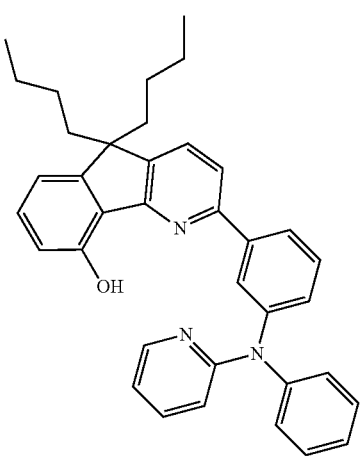

Ligand 430

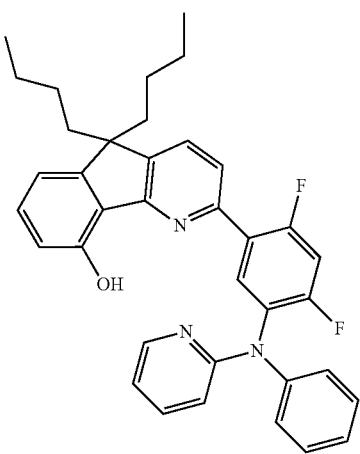

Ligand 431

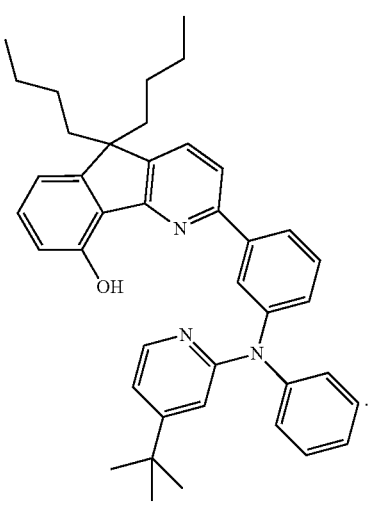

4. A method of preparing a compound of claim 1 comprising reacting Precursor 280 with carbon tetrabromide or pyridine hydrogen chloride to obtain the ligand compound of Structure II, wherein the Precursor 280 has the following structure:

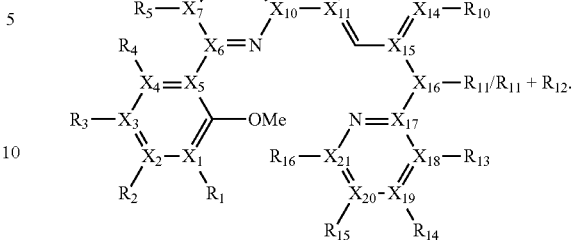

wherein $R_1$-$R_{15}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;

wherein each pair of adjacent R groups of $R_1$-$R_{16}$ can be independently two separate groups or one group, and form one or more 5-8 member rings with 2 or 4 X groups; and wherein $X_1$-$X_{21}$ are independently carbon, nitrogen, silicon, germanium, or phosphorous.

5. The method of claim 4, further comprising reacting Precursor 270 via a palladium coupling reaction to obtain the Precursor 280, wherein the Precursor 270 has the following structure:

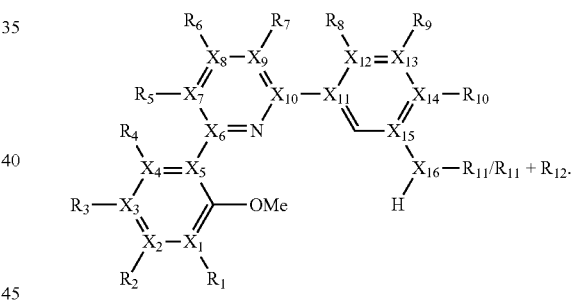

6. The method of claim 5, further comprising reacting precursor 260 via a palladium coupling reaction to obtain the Precursor 270, wherein the Precursor 260 has the following structure:

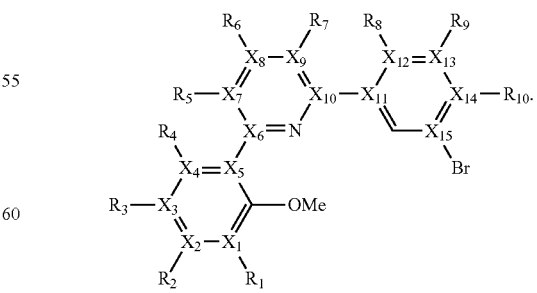

7. The method of claim 6, further comprising reacting Precursor 210 with Precursor 220 or reacting Precursor 230 with Precursor 240 to obtain the Precursor 260; wherein the Precursor 210 has the following structure:
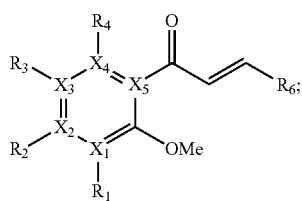
the Precursor 220 has the following structure:
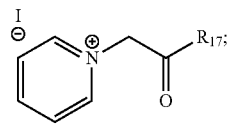
the Precursor 230 has the following structure:
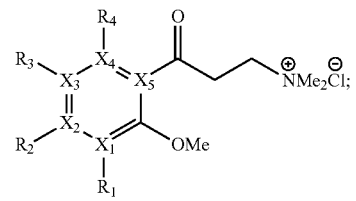
and
the Precursor 240 has the following structure:
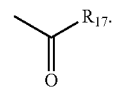
* * * * *